United States Patent
Kwak et al.

(10) Patent No.: US 9,649,080 B2
(45) Date of Patent: *May 16, 2017

(54) X-RAY IMAGING APPARATUS AND METHOD FOR CONTROLLING THE SAME

(71) Applicant: SAMSUNG ELECTRONICS CO., LTD., Suwon-si (KR)

(72) Inventors: Ho Seong Kwak, Seoul (KR); Choong Hwan Choi, Suwon-si (KR); Do Kwan Oh, Suwon-si (KR); Woo Sup Han, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

This patent is subject to a terminal disclaimer.

(21) Appl. No.: 14/694,161

(22) Filed: Apr. 23, 2015

(65) Prior Publication Data

US 2015/0223764 A1 Aug. 13, 2015

Related U.S. Application Data

(63) Continuation-in-part of application No. 13/919,496, filed on Jun. 17, 2013, now Pat. No. 9,028,144.

(30) Foreign Application Priority Data

Dec. 5, 2012 (KR) .................... 10-2012-0140002

(51) Int. Cl.
*A61B 6/04* (2006.01)
*A61B 6/08* (2006.01)
(Continued)

(52) U.S. Cl.
CPC ............ *A61B 6/469* (2013.01); *A61B 6/04* (2013.01); *A61B 6/0457* (2013.01); *A61B 6/08* (2013.01);
(Continued)

(58) Field of Classification Search
CPC .... A61B 6/00; A61B 6/02; A61B 6/04; A61B 6/0407; A61B 6/0457; A61B 6/0464;
(Continued)

(56) References Cited

U.S. PATENT DOCUMENTS 4,118,631 A 10/1978 Froggatt
6,219,403 B1 4/2001 Nishihara
(Continued)

FOREIGN PATENT DOCUMENTS

DE 195 08 715 A1 9/1996
DE 103 35 037 A1 3/2005
(Continued)

OTHER PUBLICATIONS

Communication dated Oct. 31, 2013 issued by the European Patent Office in counterpart European Patent Application No. 13172001.3.
(Continued)

*Primary Examiner* — Anastasia Midkiff
(74) *Attorney, Agent, or Firm* — Sughrue Mion, PLLC

(57) ABSTRACT

Disclosed herein are an X-ray imaging apparatus which recognizes a marker located at a part to be subjected to X-ray imaging from an image of a subject imaged by a camera and which controls a respective movement of each of an X-ray tube and an X-ray detector to a respective position which corresponds to the recognized marker, and a method for controlling the same. An X-ray imaging apparatus includes an X-ray tube which radiates X-rays toward a subject, an X-ray detector which detects X-rays which propagate through the subject, an imaging unit which generates an image of the subject, a recognizes which recognizes a part to be subjected to X-ray imaging from the image of the subject, and a position controller which controls a movement of the X-ray tube and the X-ray detector to a position corresponding to the part to be subjected to X-ray imaging.

28 Claims, 52 Drawing Sheets

(51) Int. Cl.
*H01J 37/20* (2006.01)
*A61B 6/00* (2006.01)
*A61B 6/03* (2006.01)

(52) U.S. Cl.
CPC ............ *A61B 6/4429* (2013.01); *A61B 6/467* (2013.01); *A61B 6/488* (2013.01); *A61B 6/547* (2013.01); *H01J 37/20* (2013.01); *A61B 6/032* (2013.01); *A61B 6/0407* (2013.01); *A61B 6/4233* (2013.01); *A61B 6/4464* (2013.01)

(58) Field of Classification Search
CPC .... A61B 6/08; A61B 6/40; A61B 6/42; A61B 6/4283; A61B 6/44; A61B 6/4415; A61B 6/4411; A61B 6/4429; A61B 6/4439; A61B 6/4441; A61B 6/4452; A61B 6/4464; A61B 6/4475; A61B 6/467; A61B 6/469; A61B 6/48; A61B 6/488; A61B 6/52; A61B 6/5223; A61B 6/5247; A61B 6/5294; A61B 6/54; A61B 6/545; A61B 6/547; A61B 6/58; A61B 6/582; A61B 6/587; A61B 6/588; A61B 6/589; G01N 23/00; G01N 23/02; G01N 23/04; G01N 23/043; H05G 1/00; H05G 1/02; H05G 1/26; H01J 37/00; H01J 37/02; H01J 37/023; H01J 37/20; A61N 5/10; A61N 5/1077–5/1084; G03B 42/00; G03B 42/02; G03B 42/08
USPC ......... 378/51–56, 62, 63, 91, 162–166, 189, 378/190, 193–198, 204–206, 210; 250/252.1, 491.1, 522.1, 526
See application file for complete search history.

(56) References Cited

U.S. PATENT DOCUMENTS

| | | |
|---|---|---|
| 6,259,942 B1 | 7/2001 | Westermann et al. |
| 6,585,412 B2 | 7/2003 | Mitschke |
| 6,714,629 B2 | 3/2004 | Vilsmeier |
| 6,859,521 B2 | 2/2005 | Spahn |
| 7,386,090 B2 * | 6/2008 | Schroeder ............... A61B 6/032 378/20 |
| 7,401,977 B2 | 7/2008 | Graumann et al. |
| 7,433,503 B2 | 10/2008 | Cherek et al. |
| 7,572,057 B2 * | 8/2009 | Takekoshi ............... A61B 6/588 378/205 |
| 7,581,884 B1 * | 9/2009 | Barnes ...................... A61B 6/06 378/164 |
| 9,028,144 B2 * | 5/2015 | Choi ....................... A61B 6/032 378/205 |
| 2005/0025706 A1 * | 2/2005 | Kagermeier ............. A61B 6/00 424/9.3 |
| 2008/0144776 A1 * | 6/2008 | Main .................... A61N 5/1048 378/163 |
| 2009/0046906 A1 | 2/2009 | Wohlgemuth et al. |
| 2009/0080598 A1 * | 3/2009 | Tashman ............... A61B 5/1038 378/11 |
| 2010/0135467 A1 | 6/2010 | King et al. |
| 2011/0069818 A1 * | 3/2011 | Muller ................. A61B 6/4464 378/197 |
| 2011/0164721 A1 * | 7/2011 | Jank ..................... A61B 6/4441 378/4 |
| 2012/0116374 A1 | 5/2012 | Jia et al. |
| 2013/0211419 A1 * | 8/2013 | Jensen ................. A61B 6/4405 606/130 |
| 2014/0078517 A1 * | 3/2014 | Ben-Yishai .......... A61B 8/4254 356/614 |

FOREIGN PATENT DOCUMENTS

| | | | | |
|---|---|---|---|---|
| DE | WO 2014033614 A1 * | 3/2014 | .............. | A61B 6/08 |
| WO | 2012129474 A1 | 9/2012 | | |

OTHER PUBLICATIONS

Communication dated Nov. 10, 2016, issued by the European Patent Office in counterpart European application No. 13172001.3.

* cited by examiner

FIG. 24A
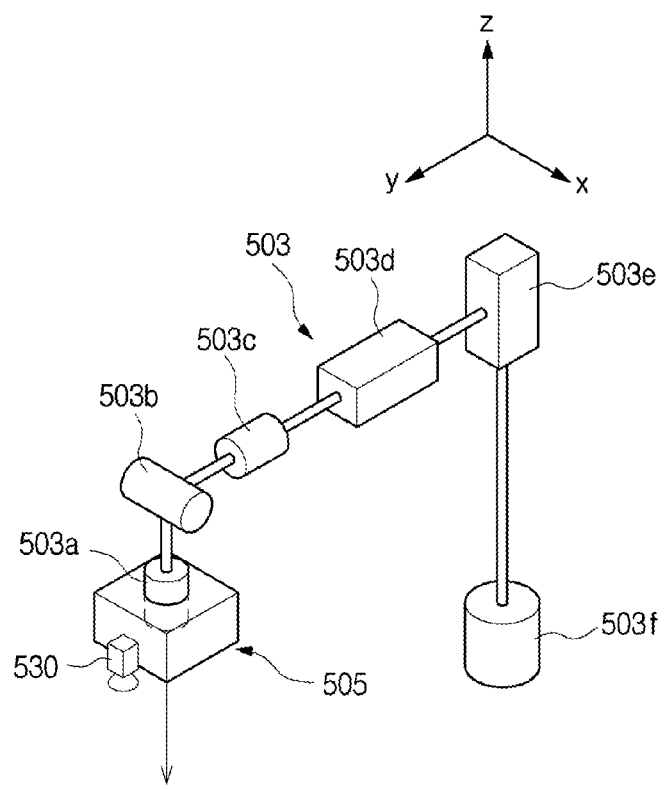
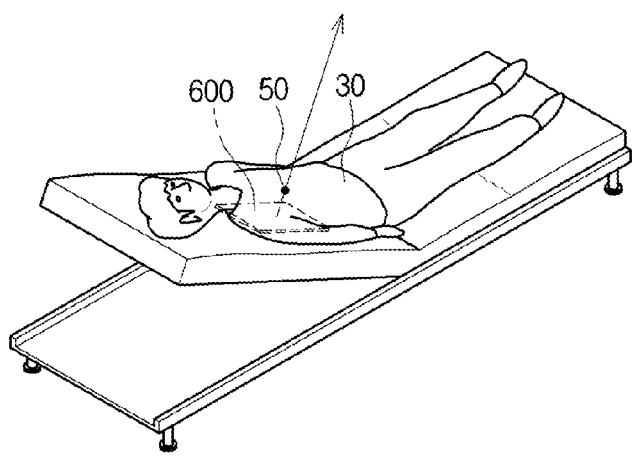

X-RAY IMAGING APPARATUS AND METHOD FOR CONTROLLING THE SAME

CROSS-REFERENCE TO RELATED APPLICATION

This application is a continuation-in-part of U.S. patent application Ser. No. 13/919,496, filed on Jun. 17, 2013, which claims priority from Korean Patent Application No. 10-2012-0140002, filed on Dec. 5, 2012 in the Korean Intellectual Property Office, the disclosure of which is incorporated herein by reference in its entirety.

BACKGROUND

1. Field

Exemplary embodiments relate to an X-ray imaging apparatus which may be used to control positions of an X-ray tub and an X-ray detector, radiate X-rays toward a subject, and detect X-rays which propagate through the subject, and a method for controlling the same.

2. Description of the Related Art

An X-ray imaging apparatus radiates X-rays toward a subject, analyzes X-rays which propagate through the subject, and checks an internal structure of the subject. Because propagation of X-rays varies based on tissue type, an internal structure of the subject may be imaged by using an attenuation coefficient obtained by digitizing the propagation of the X-rays.

Upon X-ray imaging, an X-ray tub and an X-ray detector are moved based on an imaged part of a subject. Therefore, before X-ray imaging, a user directly controls an X-ray generator and an X-ray detector.

This increases user fatigue and increases an imaging time. Because it is difficult to precisely control the position of the X-ray tube which has a large volume, X-ray imaging is repeated and a patient is exposed to a greater amount of X-ray radiation.

SUMMARY

Therefore, exemplary embodiments disclosed herein provide an X-ray imaging apparatus which recognizes a marker located at a part to be subjected to X-ray imaging from an image of a subject imaged by a camera and which controls a respective movement of each of an X-ray tube and an X-ray detector to a respective position which corresponds to the recognized marker in order to prevent an inconvenience, such as a direct movement of the X-ray tube and the X-ray detector, and in order to reduce an X-ray imaging time and the amount of X-rays to which a patient is exposed, and a method for controlling the same.

Additional aspects will be set forth in part in the description which follows and, in part, will be obvious from the description, or may be learned by practice of the exemplary embodiments.

In accordance with one aspect of one or more exemplary embodiments, there is provided an X-ray imaging apparatus which includes an X-ray tube which radiates X-rays toward a subject, an X-ray detector which detects X-rays which propagate through the subject, an imaging unit which generates an image of the subject, a recognizer which recognizes a part to be subjected to X-ray imaging from the generated image of the subject, and a position controller which controls a respective movement of each of the X-ray tube and the X-ray detector to a respective position which corresponds to the part to be subjected to X-ray imaging.

The recognizer may include a marker recognizer which recognizes a marker from the generated image of the subject in order to recognize the part to be subjected to X-ray imaging of the subject, and the marker may be located at the part to be subjected to X-ray imaging of the subject.

The position controller may control each of a center of an X-ray radiation region of the X-ray tube and a center of an X-ray detection region of the X-ray detector to match with a position of the marker.

The position controller may include a position calculator which calculates the position of the marker, and a control amount calculator which pre-stores information relating to a relative position between the generated image of the subject and at least one of the X-ray tube and the X-ray detector, and which calculates a control amount for causing respective positions of each of the X-ray tube and the X-ray detector to respectively correspond to the calculated position of the marker based on the relative position.

The marker recognizer may recognize at least one of a shape, a color, a material and a size of the marker.

The marker may include an object having a recognizable feature and may include a user's hand having a specific shape.

The marker recognizer may recognize an object having the at least one of the shape, the color, the material, and the size of the marker from the generated image of the subject.

The imaging unit may include a wide-angle camera having an angle of view such that the image of the subject is generated in a single stage.

The imaging unit may be mounted in the X-ray tube, and the position calculator may update a position calculation result of the part to be subjected to X-ray imaging while the X-ray tube moves to the respective position which corresponds to the part to be subjected X-ray imaging.

The recognizer may include an imaged-part recognizer which pre-stores information relating to a feature of the part to be subjected to X-ray imaging and which recognizes the feature from the generated image of the subject.

In accordance with another aspect of one or more exemplary embodiments, there is provided an X-ray imaging apparatus which includes a gantry which includes an X-ray tube which radiates X-rays toward a subject and an X-ray detector which detects X-rays which propagate through the subject, a slider which moves the subject to a bore of the gantry, an imaging unit which generates an image of the subject, a recognizer which recognizes a part to be subjected to X-ray imaging from the generated image of the subject, and a position controller which controls a movement of the slider such that a position of the part to be subjected to X-ray imaging corresponds to a respective position of at least one of the X-ray tube and the X-ray detector.

The recognizer may include a marker recognizer which recognizes a marker from the generated image of the subject in order to recognize the part to be subjected to X-ray imaging, and the marker may be located at the part to be subjected to X-ray imaging.

The position controller may include a position calculator which calculates a position of the marker, and a control amount calculator which pre-stores information relating to a relative position between the generated image of the subject and at least one of the X-ray tube and the X-ray detector, and which calculates a control amount for causing the slider to move based on the pre-stored information relating to the relative position.

The recognizer may include an imaged-part recognizer which pre-stores information relating to a feature of the part to be subjected to X-ray imaging and which recognizes the feature from the generated image of the subject.

In accordance with another aspect of one or more exemplary embodiments, there is provided a method for controlling an X-ray imaging apparatus which includes an X-ray tube which radiates X-rays toward a subject and an X-ray detector which detects X-rays which propagate through the subject, the method including generating an image of the subject, recognizing a part to be subjected to X-ray imaging from the generated image of the subject, and controlling a respective movement of each of the X-ray tube and the X-ray detector to a respective position which corresponds to the part to be subjected to X-ray imaging.

The recognizing the part to be subjected to X-ray imaging may include recognizing a marker from the generated image of the subject in order to recognize the part to be subjected to X-ray imaging of the subject.

The controlling the respective movement of each of the X-ray tube and the X-ray detector to the position which corresponds to the part to be subjected to X-ray imaging may include controlling each of a center of an X-ray radiation region of the X-ray tube and a center of an X-ray detection region of the X-ray detector to match with a position of the marker.

The controlling the respective movement of each of the X-ray tube and the X-ray detector to the position which corresponds to the part to be subjected to X-ray imaging may include pre-storing information relating to a relative position between the generated image of the subject and at least one of the X-ray tube and the X-ray detector, calculating a position of the marker, and calculating a control amount for causing respective positions of each of the X-ray tube and the X-ray detector to respectively correspond to the calculated position of the marker based on the relative position.

The method may further include pre-storing information relating to a feature which includes information relating to at least one of a shape, a color, a material and a size of the marker.

The marker may include an object having a recognizable feature and may include a user's hand having a specific shape.

The recognizing the part to be subjected to X-ray imaging of the subject may include recognizing an object having the feature which includes the information relating to at least one of the shape, the color, the material, and the size of the marker from the generated image of the subject.

The image of the subject may be generated by using a wide-angle camera having an angle of view such that the image of the subject is generated in a single stage.

An imaging unit may be mounted in the X-ray tube, and the calculating the position of the marker may include updating a position calculation result of the part to be subjected to X-ray imaging while the X-ray tube moves to the respective position which corresponds to the part to be subjected X-ray imaging.

The method may further include pre-storing information relating to a feature of the part to be subjected to X-ray imaging, and the recognizing the part to be subjected to X-ray imaging may include recognizing the feature from the generated image of the subject.

In accordance with a further aspect of one or more exemplary embodiments, there is provided a method for controlling an X-ray imaging apparatus which includes a gantry which includes an X-ray tube which radiates X-rays toward a subject and an X-ray detector which detects X-rays which propagate through the subject, the method including moving a slider, on which the subject is located, to a bore of the gantry, generating an image of the subject, recognizing a part to be subjected to X-ray imaging from the generated image of the subject, and controlling a movement of the slider such that the part to be subjected to X-ray imaging corresponds to a respective position of at least one of the X-ray tube and the X-ray detector.

The recognizing the part to be subjected to X-ray imaging from the generated image of the object may include recognizing a marker which is located at the part to be subjected to X-ray imaging from the generated image of the subject.

The controlling the movement of the slider may include pre-storing information relating to a relative position between the generated image of the subject and at least one of the X-ray tube and the X-ray detector and calculating a control amount for causing the slider to move based on the pre-stored information relating to the relative position.

The calculating the control amount for causing the slider to move may include calculating a control amount for causing the slider to move such that a position of the marker corresponds to at least one of the X-ray tube and the X-ray detector.

The recognizing the part to be X-ray imaging of the object may include pre-storing information relating to a feature of the part to be subjected to X-ray imaging and recognizing the feature from the generated image of the subject.

BRIEF DESCRIPTION OF THE DRAWINGS

These and/or other aspects will become apparent and more readily appreciated from the following description of the exemplary embodiments, taken in conjunction with the accompanying drawings of which:

FIGS. 10A, 10B, and 100 are diagrams which illustrate a recognition of a marker from an image of a subject which is generated by using the method illustrated in FIG. 9;

FIGS. 24A, 24B and 24C are diagrams schematically illustrating a process in which an orientation and a position of an X-ray tube are aligned;

DETAILED DESCRIPTION

Hereinafter, an X-ray imaging apparatus according to an exemplary embodiment will be described with reference to the accompanying drawings.

Figure 1:
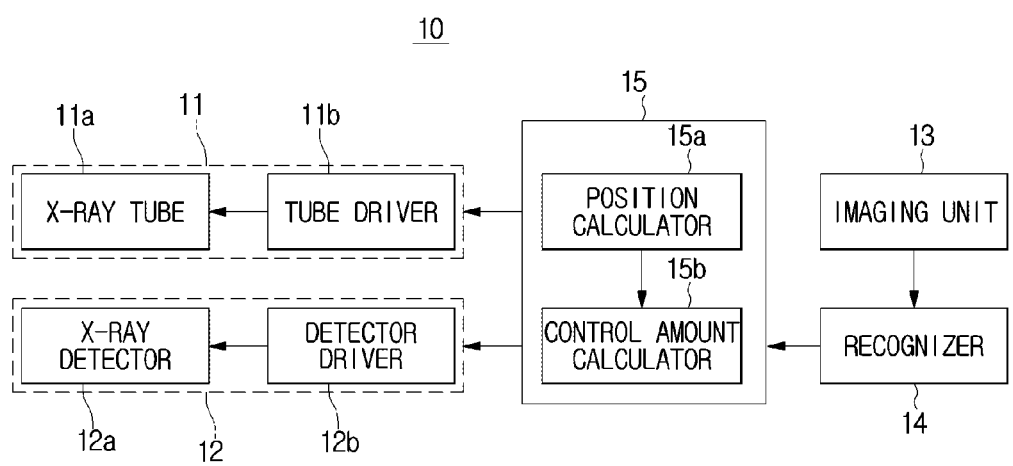
FIG. 1 is a block diagram which illustrates an X-ray imaging apparatus, according to an exemplary embodiment.

FIG. 1 is a block diagram which illustrates an X-ray imaging apparatus, according to an exemplary embodiment.

Referring to FIG. 1, the X-ray imaging apparatus includes an X-ray tube unit 11 which generates and radiates X-rays toward a subject, an X-ray detection unit 12 which detects X-rays which propagate through the subject, an imaging unit 13 which generates an image of the subject, a recognizer 14 which analyzes the image of the subject which is generated by the imaging unit 13 and which recognizes a part to be subjected to X-ray imaging, and a position controller 15 which includes a position calculator 15a and a control amount calculator 15b which match the respective positions of an X-ray tube 11a and an X-ray detector 12a with the position of the part to be subjected to the X-ray imaging.

If the imaging unit 13 generates an image of the subject and transmits the image of the subject to the recognizer 14, the recognizer 14 recognizes the part to be subjected to X-ray imaging from the image of the subject. In recognition of the part to be subjected to X-ray imaging, the part to be subjected to X-ray imaging or a marker located at the part to be subjected to X-ray imaging may be recognized. If the recognizer 14 transmits a result of the recognizing to the position controller 15, the position calculator 15a of the position controller 15 calculates the position of the recognized marker or the part to be subjected to X-ray imaging, and the control amount calculator 15b calculates a control amount to match the respective positions of each of the X-ray tube 11a and an X-ray detector 12a with the position of the part to be subjected to X-ray imaging. The control amount is transmitted to a tube driver 11b and a detector driver 12b, both of which are driven by a driving device, such as, for example, a motor.

Hereinafter, an exemplary embodiment of an X-ray imaging apparatus for recognizing a marker and an exemplary embodiment of an X-ray imaging apparatus for recognizing a part to be subjected to X-ray imaging will be described.

Figure 2:
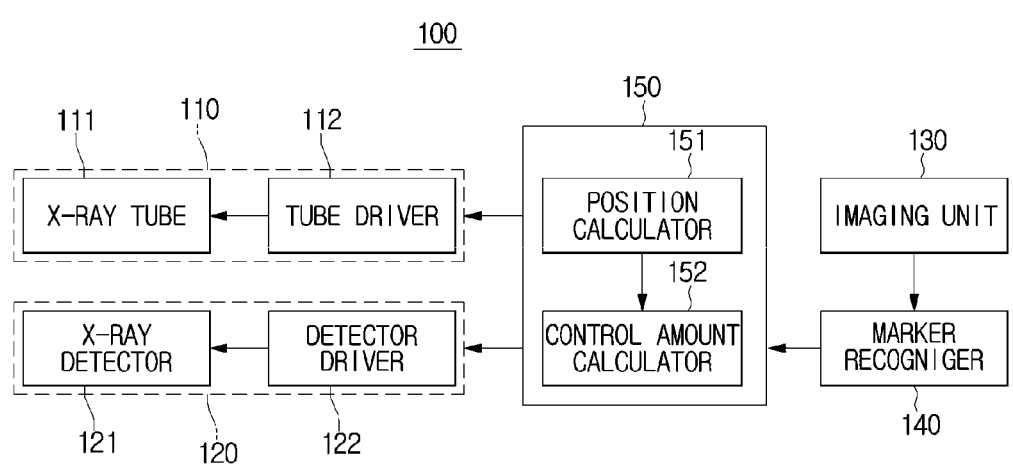
FIGS. 2 and 3 are block diagrams which illustrate an X-ray imaging apparatus which recognizes a marker, according to an exemplary embodiment.
Figure 3:
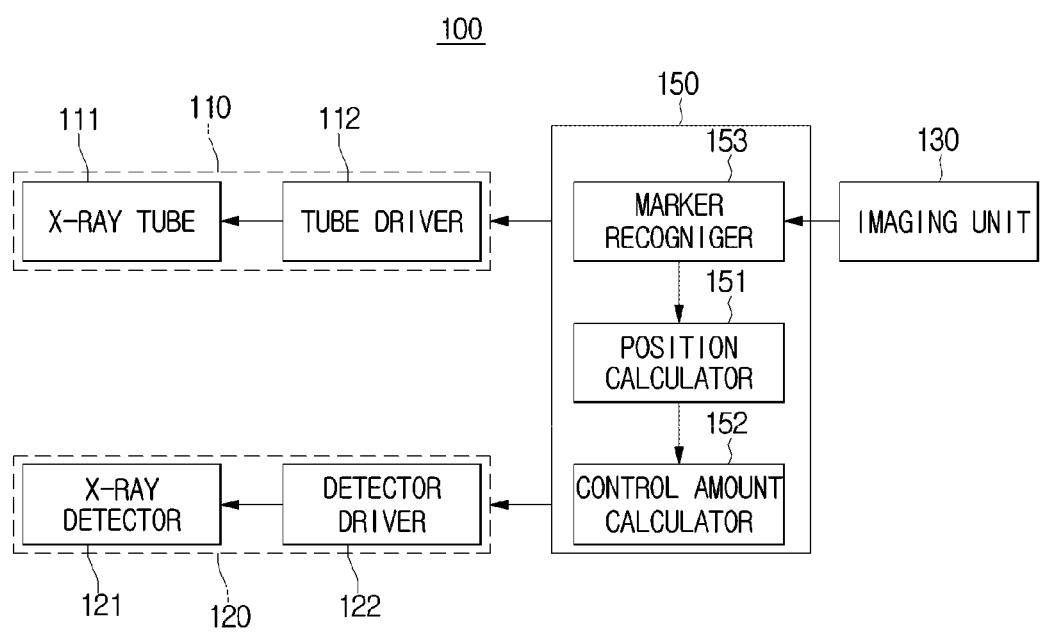
Figure 4A:
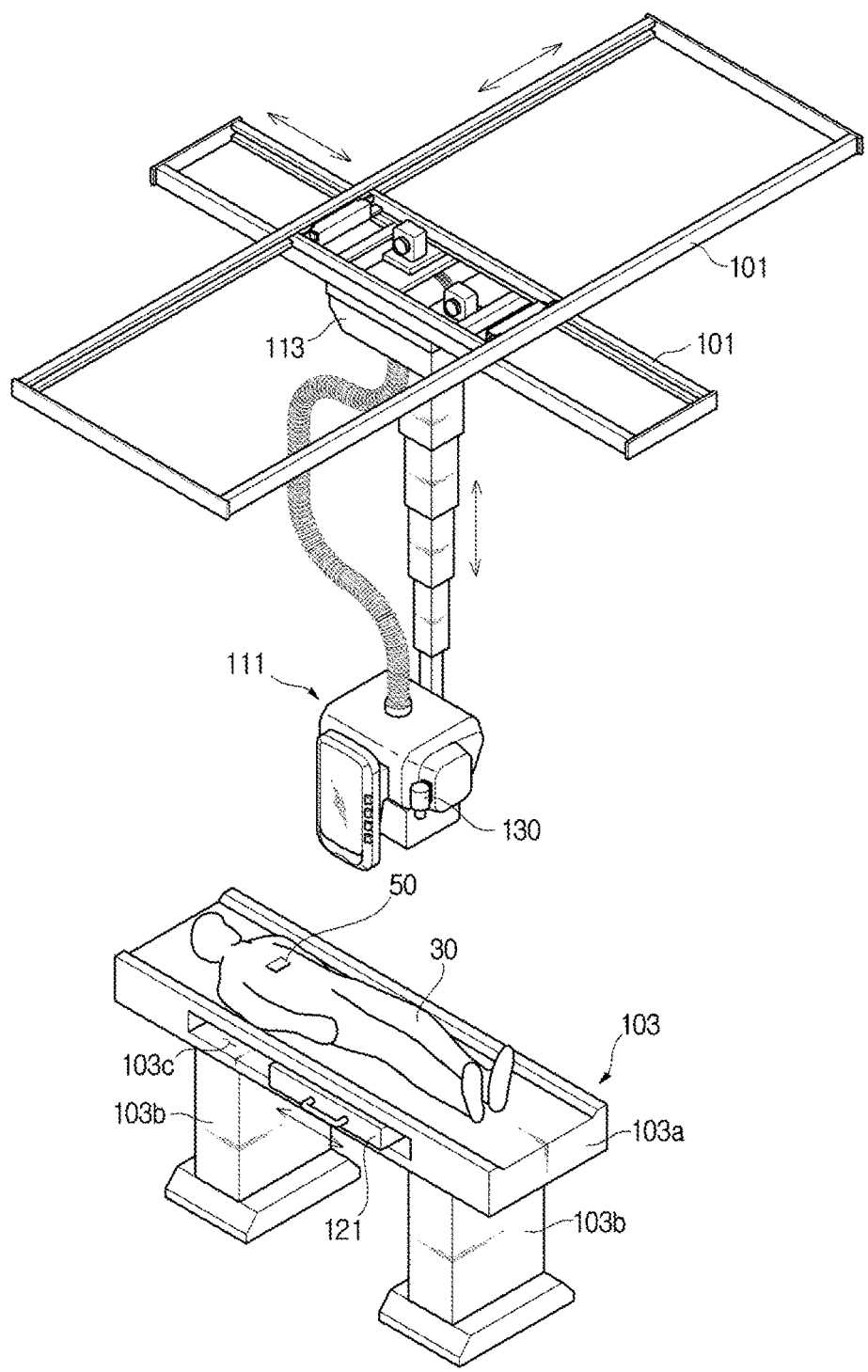
FIGS. 4A and 4B are diagrams which illustrate an appearance of an X-ray imaging apparatus, according to an exemplary embodiment.
Figure 4B:
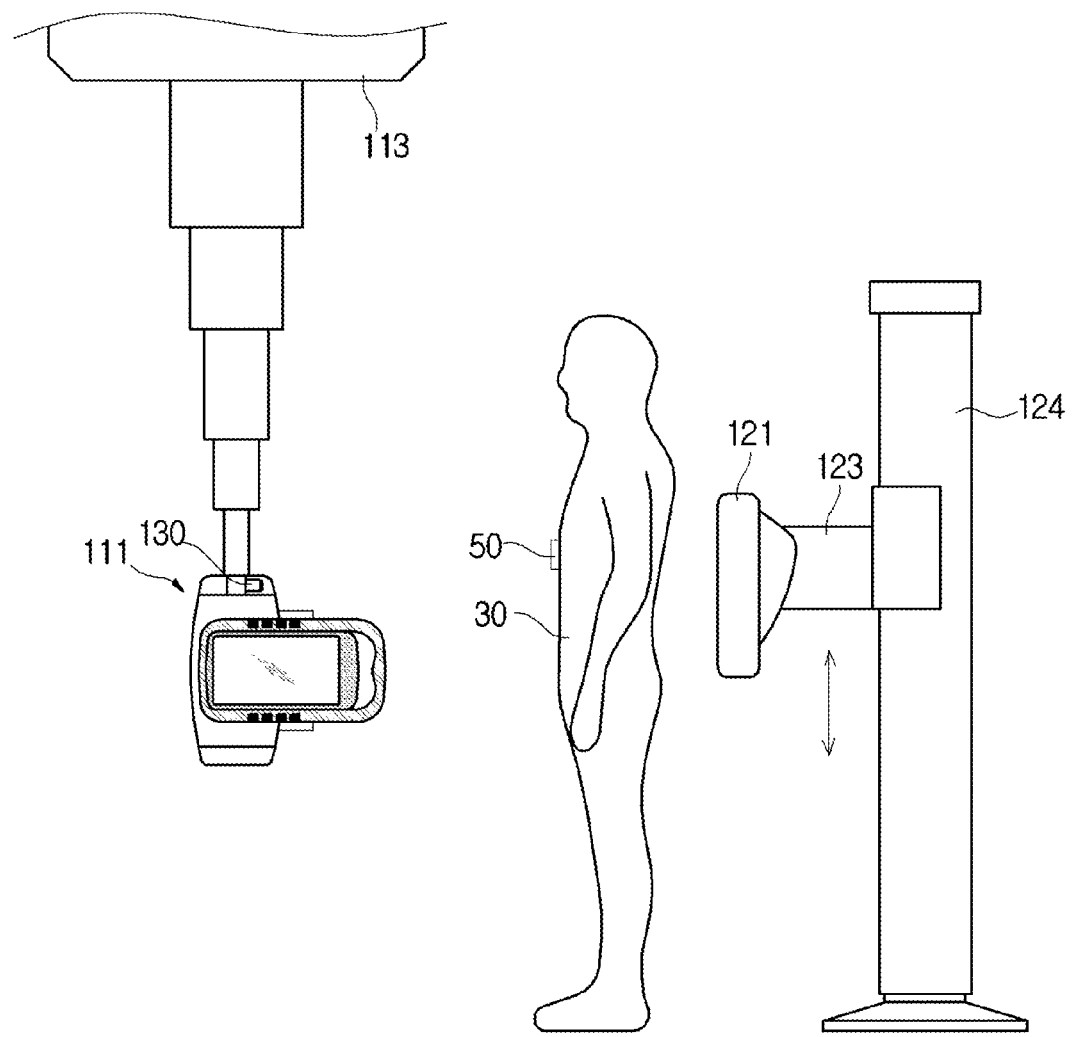

FIGS. 2 and 3 are block diagrams which illustrate an X-ray imaging apparatus which recognizes a marker, according to an exemplary embodiment, and FIGS. 4A and 4B are diagrams which illustrate an appearance of an X-ray imaging apparatus, according to an exemplary embodiment. Hereinafter, an operation of the X-ray imaging apparatus according to the exemplary embodiment will be described with reference to FIGS. 2, 3, 4A, and 4B.

The X-ray imaging apparatus 100 according to the exemplary embodiment includes an X-ray tube unit 110 which generates and radiates X-rays toward a subject, an X-ray detection unit 120 which detects X-rays which propagate through the subject, an imaging unit 130 which generates an image of the subject, a marker recognizer 140 which analyzes the image of the subject which is generated by the imaging unit 13 and which recognizes a marker, and a position controller 150 which includes a position calculator 151 and a control amount calculator 152 and which moves each of an X-ray tube 111 and an X-ray detector 121 to a respective position which corresponds to the recognized marker.

The X-ray tube unit 110 includes an X-ray tube 111 which generates and radiates X-rays toward the subject and a first tube driver 112 which moves the X-ray tube 111.

Energy of X-rays to be generated by the X-ray tube 111 may be set based on the part of the subject 30 to be subjected to X-ray imaging or based on the purpose of the X-ray imaging. The X-ray tube 111 receives power from a power supply (not shown) and generates X-rays. Energy of X-rays may be controlled by a tube voltage, and the X-ray intensity or dose may be controlled by a tube voltage and an X-ray exposure time.

The X-ray tube 111 may radiate monochromatic X-rays or polychromatic X-rays. If the X-ray tube 111 radiates polychromatic X-rays, the energy band of the radiated X-rays may be defined by an upper limit and a lower limit.

The upper limit of the energy band, that is, a maximum energy of the radiated X-rays is controlled by the level of the tube voltage and the lower limit of the energy band, and a minimum energy of the radiated X-rays may be controlled by a filter provided inside or outside of the X-ray tube 111. If X-rays of a low energy band are filtered by the filter, an average energy of the radiated X-rays may be increased.

As shown in FIGS. 4A and 4B, the X-ray tube 111 is connected to a movement cartridge 113, and the movement cartridge 113 may be moved along a rail 101 which is mounted on the ceiling of an inspecting room in a horizontal direction or a vertical direction. Accordingly, if the first tube driver 112 drives the movement cartridge 113, the X-ray tube 111 connected to the movement cartridge 113 is also moved. In particular, the X-ray tube 111 may be moved by movement of the movement cartridge 113 connected to the X-ray tube 111, and the first tube driver 112 drives the X-ray tube 111 through the movement cartridge 113. The vertical direction corresponds to the longitudinal direction of a patient table 103, and the horizontal direction is perpendicular to the longitudinal direction of the patient table.

The X-ray detection unit 120 includes an X-ray detector 121 which detects X-rays which propagate through the subject and a second detector driver 122 which drives the X-ray detector 121 in the vertical direction.

The X-ray detector 121 detects X-rays which propagate through the subject, converts the detected X-rays into an electrical signal, and acquires X-ray data. In an exemplary embodiment, the X-ray detector 121 may include a light receiving element which generates charges when an X-ray photon is absorbed and a reading circuit which reads and processes an electrical signal from the generated charges. Examples of a material used in the light receiving element may include one of or more a-Si, a-Se, CdZnTe, $HgI_2$, $PbI_2$, and/or any other suitable material.

The operation of the X-ray detector 121 may be divided into a charge integration mode for storing charges for a predetermined time based on a method for acquiring an electrical signal and then acquiring a signal therefrom, and a photon counting mode for performing counting when a signal is generated by a single X-ray photon. Any of the above-described methods may be applied to the X-ray detector 121, according to the exemplary embodiment.

The X-ray imaging apparatus may use a first mode for performing X-ray imaging in a state in which a subject is located on the patient table 103 and a second mode for performing X-ray imaging in a state in which a subject stands between an X-ray tube and an X-ray detector. As shown in FIGS. 3A and 3B, the above-described two modes may be applied to the X-ray imaging apparatus 100 according to the exemplary embodiment.

In the first mode for performing X-ray imaging in a state in which a subject 30 is located on the patient table 103, as shown in FIG. 3A, an upper plate 103a is supported by a support 103b, and a space 103c into which the X-ray detector 121 is inserted and moved in the vertical direction is provided under the upper plate 103a. The X-ray detector 121 is inserted into the space 103c provided under the upper plate 103a to be moved by the second detector driver 122 in the vertical direction.

In the second mode for performing X-ray imaging in a state in which the subject 30 stands between the X-ray tube 111 and the X-ray detector 121, as shown in FIG. 3B, the X-ray detector 121 is connected to a slider 123, and the slider 123 is mounted on a support 124 to be moved by the second detector driver 122 upward or downward.

As described above, the X-ray tube 111 and the X-ray detector 121 may be moved, and the X-ray tube 111 and the X-ray detector 121 should be moved to a position which corresponds to the part to be subjected to X-ray imaging before commencing the X-ray imaging. If a user directly moves the X-ray tube 111 and the X-ray detector 121, user fatigue and the likelihood of having to repeat the X-ray imaging are increased. The X-ray imaging apparatus 100 according to the exemplary embodiment may generate an image of a marker 50 when the user locates the marker 50 on the part of the subject to be subjected to X-ray imaging, and then move each of the X-ray tube 111 and the X-ray detector 121 to a respective position which corresponds to the position of the marker 50. Hereinafter, generating an image of the marker and moving the X-ray tube 111 and the X-ray detector 121 will be described in detail.

Before commencing X-ray imaging, a user, such as, for example, a radiologist or doctor, may locate the marker 50 on the part of the subject to be subjected to X-ray imaging. Any one of the color, material, size, and shape of the marker 50 is not limited, provided that the marker recognizer 140 can recognize the marker from the image which is generated by the imaging unit 130.

For example, the marker 50 may have a polygonal shape, as shown in FIGS. 4A and 4B, or any one of other shapes so long as the marker can be recognized by using a pre-stored recognition algorithm.

The color of the marker 50 is not limited so long as the marker can be recognized by using a color recognition algorithm.

The material of the marker 50 may include, but is not limited to, any one or more of fiber, metal, plastic, rubber, a part of a human body, such as a finger, and/or any other suitable material. If the material of the marker 50 influences the propagation of X-rays, the marker 50 may be removed from the subject 30 after the X-ray tube 111 and the X-ray detector 121 are moved to target positions. Also, the marker 50 may be light radiated from a light source.

The size of the marker is not limited, and the position of the marker and a control amount may be easily calculated if the size of the marker is not greater than the size of the part to be subjected to X-ray imaging or an X-ray radiation region.

If the subject 30 lies as shown in FIG. 4A, the marker 50 may be placed on the subject 30 and, if the subject 30 stands as shown in FIG. 4B, the user or the subject 30 may hold the marker 50, or the marker 50 may be fixed to the part to be subjected to X-ray imaging by using a fixing member, such as, for example, an adhesive or a string.

If the marker 50 is located on the part to be subjected to X-ray imaging, the imaging unit 130 generates an image of the subject. The imaging unit 130 may be implemented by a camera which is a general imaging apparatus. For example, the imaging unit may include, but is not limited to, at least one of a charge-coupled device (CCD) camera, a complementary metal-oxide-semiconductor (CMOS) camera, and/or any other suitable type of device which can be used to generate an image, in the exemplary embodiment.

As shown in FIGS. 4A and 4B, the imaging unit 130 may be mounted on the X-ray tube 111 and the exemplary embodiment is not limited thereto. The imaging unit 130 may be mounted on the ceiling of an inspecting room in order to generate an image of the subject 30, or may be supported by a support at a position adjacent to the subject 30 in order to generate an image of the subject 30. The position of the imaging unit 130 is not limited, provided that the subject 30 located between the X-ray tube 111 and the X-ray detector 121 can be imaged.

The marker recognizer 140 and the controller 150 may include a memory in which a program capable of performing respective operations and data necessary for executing the program are stored and a processor configured to execute the stored program. The marker recognizer 140 and the controller 150 may use a separate processor or memory. Alternatively, as illustrated in FIG. 3, the marker recognizer 153 may be included as a component of the controller 150. In this case, the position calculator 151, the control amount calculator 152 and the marker recognizer 153, which are components of the controller 150, may also use a separate processor or memory, and share the processor and the memory.

Figure 5:
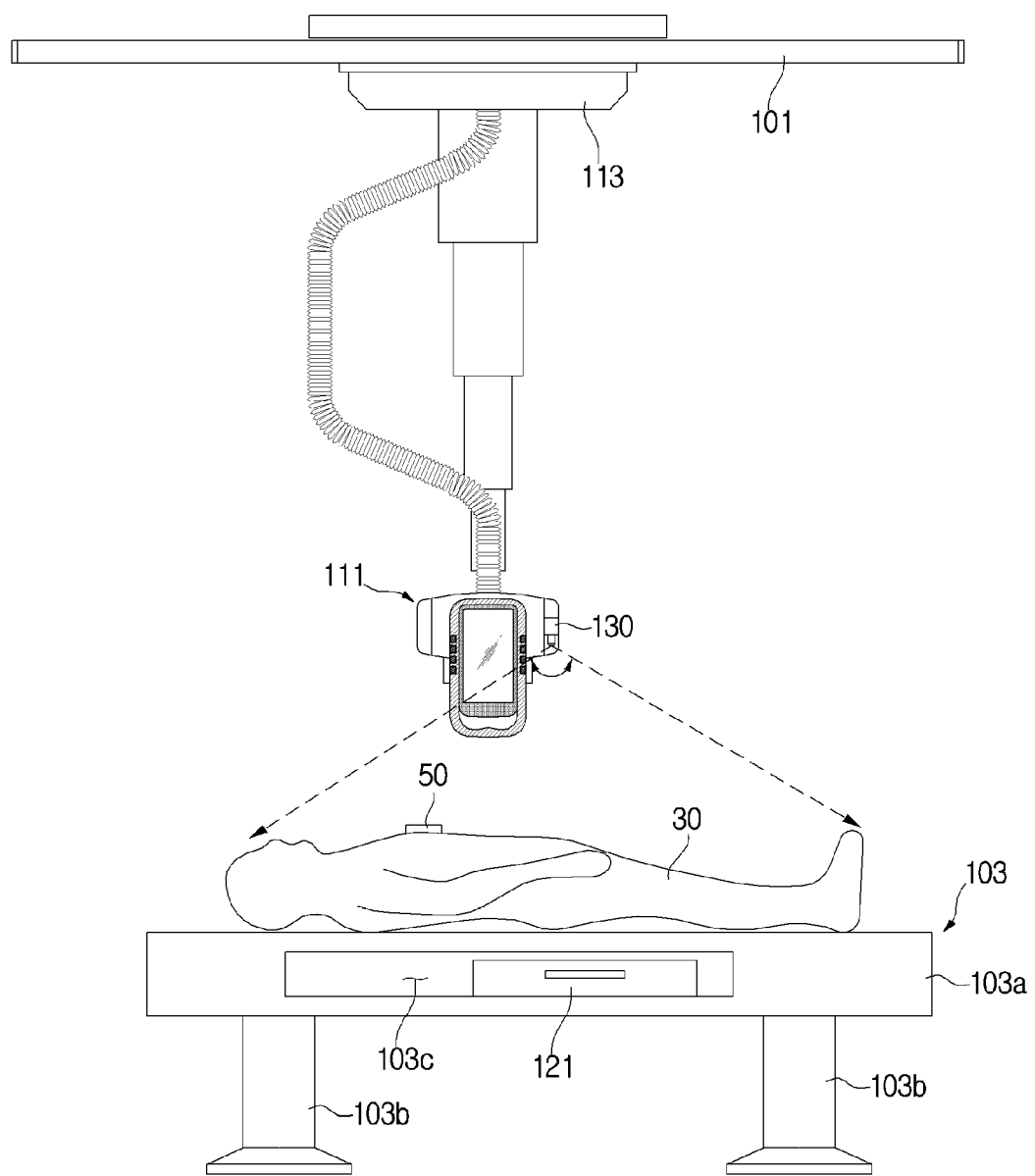
FIG. 5 is a diagram which illustrates an appearance of an X-ray imaging apparatus in a case in which a wide-angle lens is used as an imaging unit.

FIG. 5 is a diagram which illustrates n appearance of an X-ray imaging apparatus in a case in which a wide-angle lens is used as an imaging unit. For convenience of description, in the below-described exemplary embodiment, as shown in FIG. 4A, X-ray imaging is performed in a state in which the subject 30 lies on the patient table 103 and the imaging unit 130 is mounted in the X-ray tube 111.

As an example of the imaging unit 130, a wide-angle camera may be used. The wide-angle camera refers to a camera in which a wide-angle lens having a focal length which is shorter than that of a normal lens is mounted. The shorter the focal length is, the wider is an angle of view. Accordingly, the imaging range of the wide-angle camera is wider that of a corresponding camera having the normal lens. If a wide-angle camera having an angle of view which may cover the length of the patient table 103 is used, as shown in FIG. 5, imaging may be performed over the whole range of the patient table 103 in a single stage.

Because the marker 50 indicates the part of the subject 30 to be subjected to X-ray imaging, only the subject 30 may appear in the image of the subject. However, because patients have different heights, the imaging unit 130 may have an angle of view which covers the length of the upper plate 103a of the patient table 103.

Figure 6A:
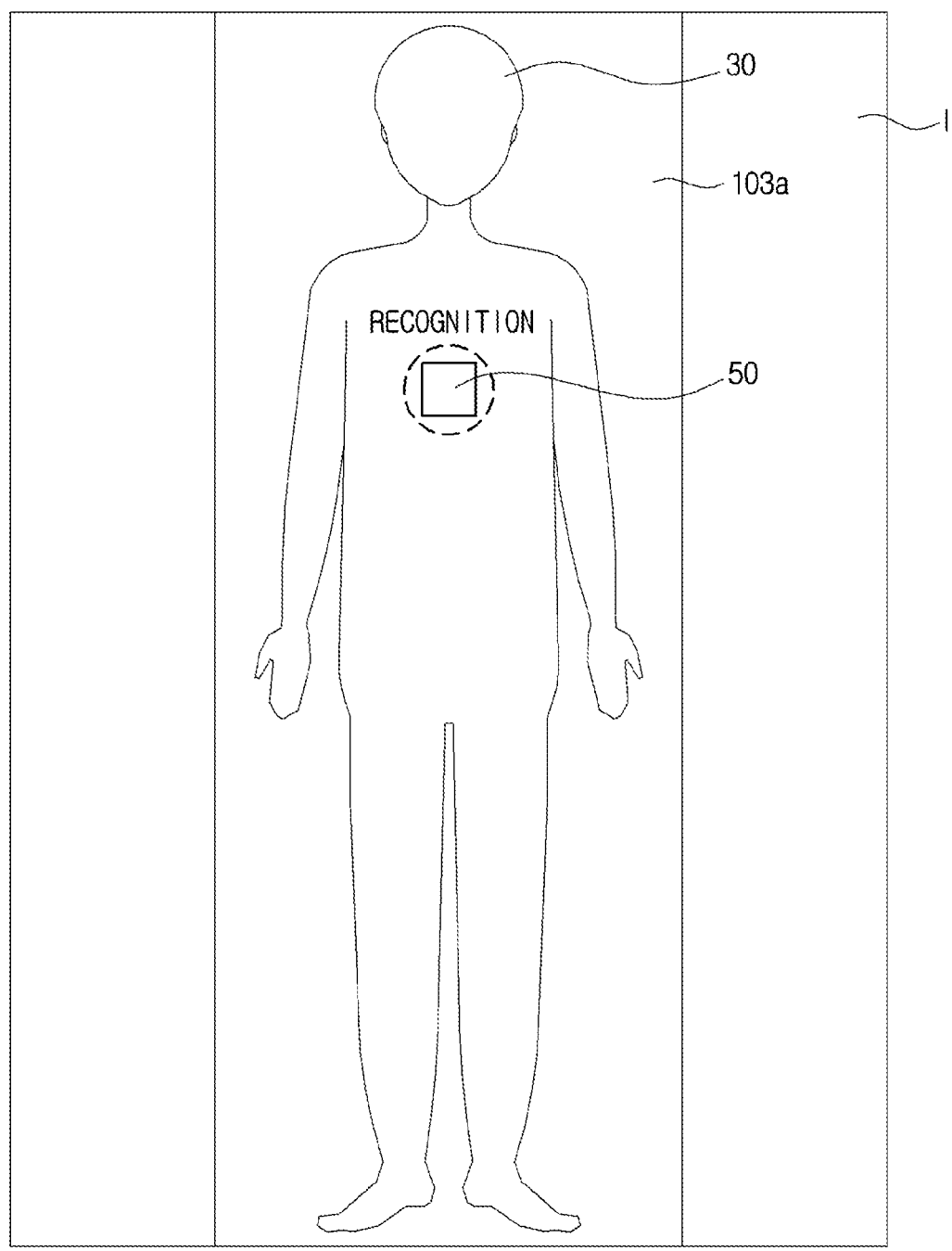
FIGS. 6A and 6B are diagrams which illustrate a recognition of a marker from an image of a subject by a marker recognizer.
Figure 6B:
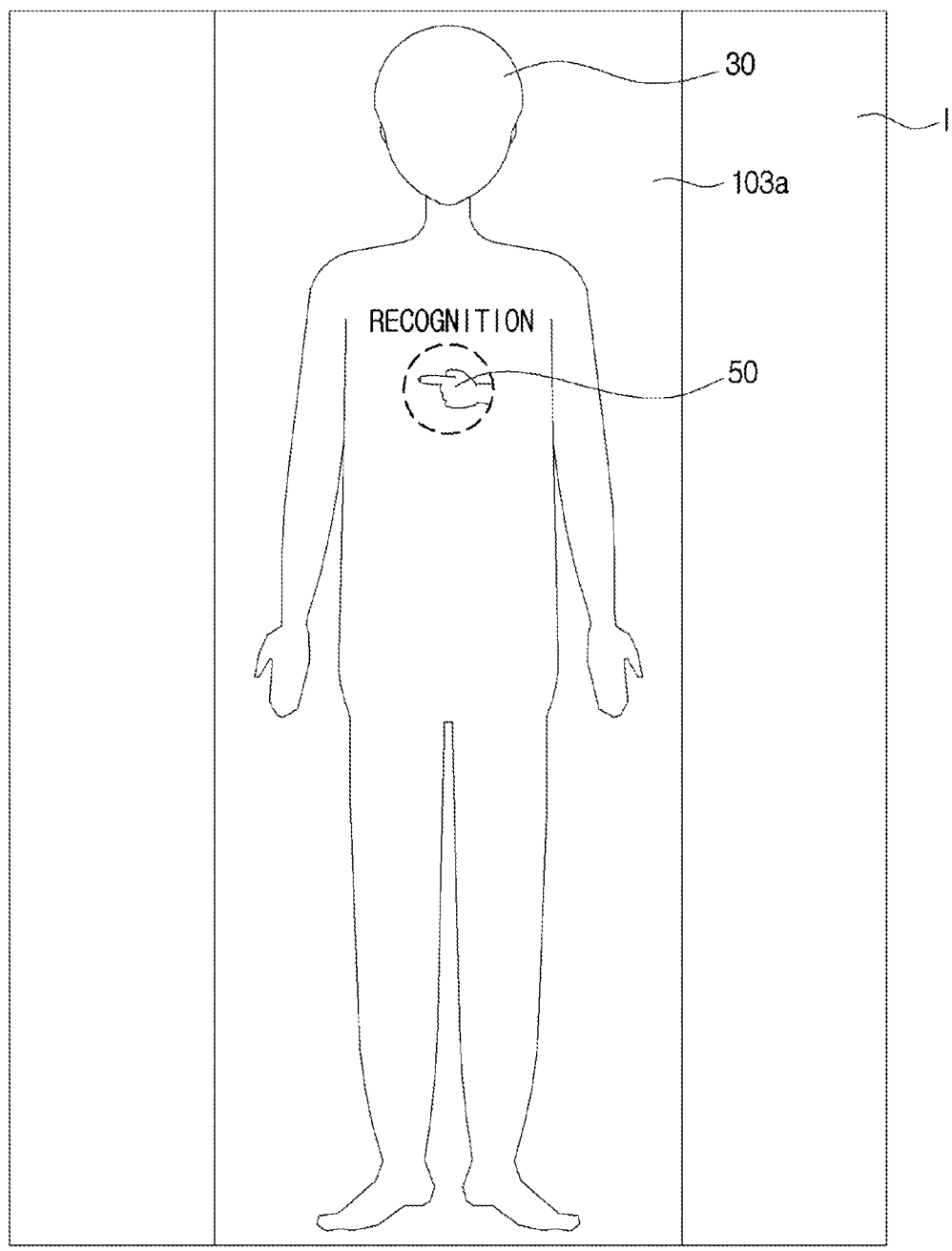

FIGS. 6A and 6B are diagrams which illustrate a recognition of a marker from an image of a subject by a marker recognizer.

The imaging unit 130 transmits the image of the subject to the marker recognizer 140, and the marker recognizer 140 recognizes the marker from the image of the subject. When the marker recognizer 140 recognizes the marker, any of various object recognition algorithms, including a hidden Markov model, may be applicable. Information relating to a feature of the used marker may be pre-stored, and a corresponding feature of the subject which appears in the image of the subject may be extracted and compared with the pre-stored information relating to the feature of the marker, thereby enabling recognition of the marker. The feature used to recognize the marker may include at least one of a shape, a color, a material and a size.

As an example, as shown in FIG. 6A, if information relating to the feature of a rectangle having a predetermined size and shape is pre-stored, the marker recognizer 140 finds a rectangular object having the predetermined size and shape from the image I of the subject. If the rectangular marker 50 having the predetermined size and shape is present in the image I of the subject, the rectangular marker is recognized and the result of the recognition is transmitted to the position controller 150.

As described above, a part of a human body may be used as the marker 50 and, in this case, the user may point to a part to be subjected to X-ray imaging with a finger. In this case, information relating to the finger having a specific shape, as shown in FIG. 6B, may be pre-stored as corresponding to the marker 50. The marker recognizer 140 finds an object having the specific finger shape which corresponds to the pre-stored information in the image I of the subject, recognizes the marker 50 having the specific finger shape if the marker 50 having the specific finger shape is present, and outputs the result of the recognition to the position controller 150.

Figure 7A:
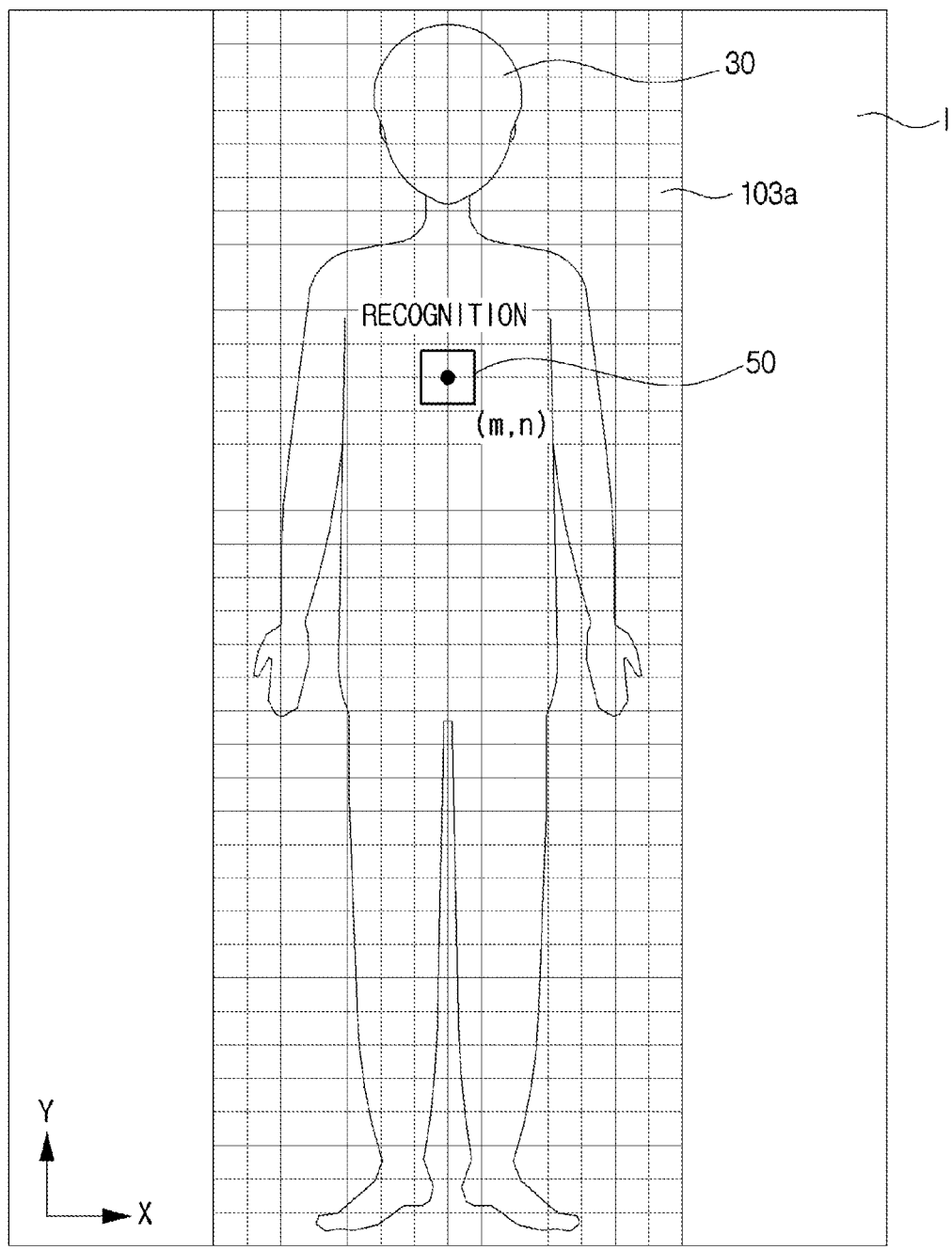
FIG. 7A is a diagram which illustrates a calculation of a position of a marker from an image of a subject by a position controller.
Figure 7B:
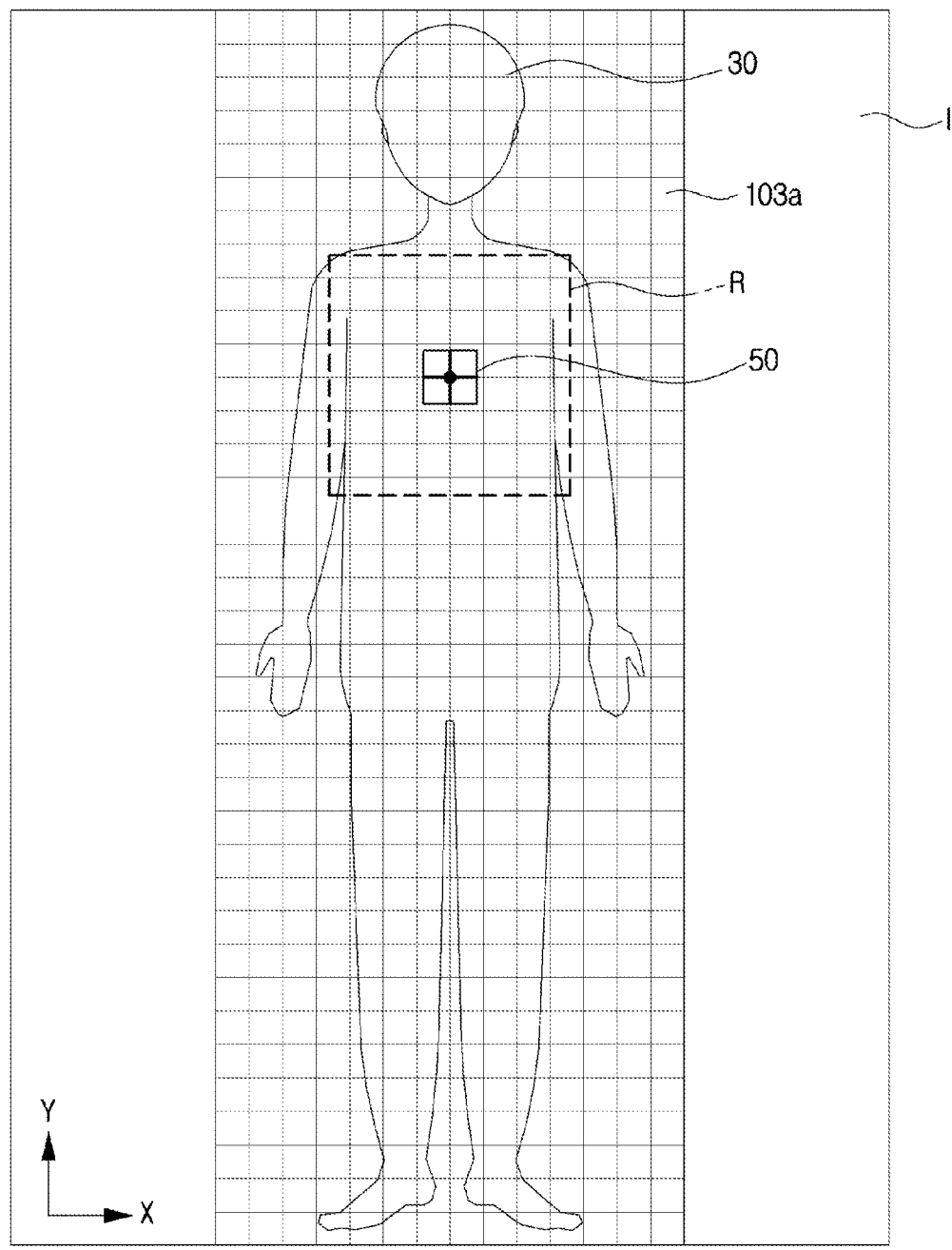
FIG. 7B is a diagram which illustrates an X-ray radiation region which is controlled by a position controller.

FIG. 7A is a diagram which illustrates a calculation of the position of a marker in an image of a subject by the position controller, and FIG. 7B is a diagram which illustrates an X-ray radiation region controlled by the position controller.

As shown in FIG. 2, the position controller 150 includes the position calculator 151 and the control amount calculator 152.

Referring to FIG. 7A, the position calculator 151 calculates the position of the marker 50 which has been recognized by the marker recognizer 140. As an example, the position of the marker 50 may be calculated as coordinates (m, n) of a two-dimensional coordinate system. The image I of the subject may be represented by a two-dimensional coordinate system and, because the marker 50 may be located only in the upper plate 103a, only the internal space of the upper plate 103a may be represented by a two-dimensional coordinate system as shown in FIG. 7A.

The position calculator 151 may complete the calculation of the position of the marker 50 before the X-ray tube 111 and the X-ray detector 121 are moved, or may calculate the position of the marker during a predetermined period or in real time while the X-ray tube 111 and the X-ray detector 121 are being moved to a target position, thereby updating the result.

The latter case is possible if the imaging unit 130 may be mounted in any one of the X-ray tube 111, the movement cartridge 113 or a movable support. While the imaging unit is being moved, the subject is imaged, the marker is recognized and the target position is calculated during a predetermined period or in real time. Because the target position corresponds to the marker 50 and the X-ray tube 111, as the X-ray tube 111 is moved, the imaging unit 130 and the marker 50 may move closer to each other and, as the imaging unit 130 and the marker 50 may move closer to each other, an accuracy of a recognition and a corresponding position calculation with respect to the marker 50 may be improved.

The control amount calculator 152 calculates a control amount for causing the respective positions of each of the X-ray tube 111 and the X-ray detector 121 to correspond with the position of the marker 50. For the calculation of the control amount, the control amount calculator 152 may pre-store information relating to a relative position between the X-ray tube 111 and the subject image I and information relating to a relative position between the X-ray detector 121 and the subject image I. In particular, the actual positions of the X-ray tube 111 and the X-ray detector 121 as expressed by using the coordinate system of the image I of the subject may be pre-stored.

Accordingly, the control amount calculator 152 may acquire the target positions of the X-ray tube 111 and the X-ray detector 121 based on the stored relative position information, and then calculate the required control amount for causing to move the X-ray tube 111 and the X-ray detector 121 to respective target positions. The target positions of the X-ray tube 111 and the X-ray detector 121, more particularly, the positions corresponding to the marker 50, are positions where each of the center of the X-ray radiation region R of the X-ray tube 111 and the center of the detection region of the X-ray detector 121 match the marker 50 or the center of the marker 50 in a two-dimensional space.

The exemplary embodiment is not limited thereto, and the part to be subjected to X-ray imaging as indicated by the marker 50 may be included in the X-ray radiation region in a state in which the center of the marker 50 does not match the radiation region and detection region. More specifically, if the size of the marker 50 exceeds a predetermined size, a portion of the part to be subjected to X-ray imaging may not be imaged when the center of the marker 50 does not match the X-ray radiation region and the X-ray detection region. Accordingly, if the size of the marker 50 is less than the predetermined size, the position of any portion of the region of the marker 50 may be calculated, but, if the size of the marker 50 is greater than the predetermined size, the position of the center of the marker 50 may be calculated.

In order to move the X-ray tube 111 to the target position, the position of the X-ray tube 11 is controlled in each of the vertical direction and the horizontal direction, and each of a vertical-direction control amount and a horizontal-direction control amount for causing the X-ray tube to be moved from a current position to a target position may be calculated. Because the X-ray detector 121 is generally moved only in the vertical direction in the space 130c provided under the upper plate 103a, the control amount calculator 152 may calculate the vertical-direction control amount relating to the X-ray detector 121 in consideration of only the vertical-direction factor of the position of the marker calculated by the position calculator 151. However, this is only an exemplary embodiment, and the horizontal-direction control amount may be calculated if the X-ray detector 121 is movable in the horizontal direction.

If the X-ray imaging apparatus 100 has the structure shown in FIG. 3A, because the X-ray detector 121 is moved upward or downward, the control amount calculator 152 calculates the upward/downward control amount which relates to the X-ray detector 121.

The control amount calculator 152 transmits a driving command which corresponds to the calculated control amount to the tube driver 112 and the detector driver 122. When the tube driver 112 moves the X-ray tube 111 to the target position based on the driving command, as shown in FIG. 7B, the center of the X-ray radiation region R which is displayed by light radiated from the X-ray tube 111 matches the center of the marker 50.

Figure 8:
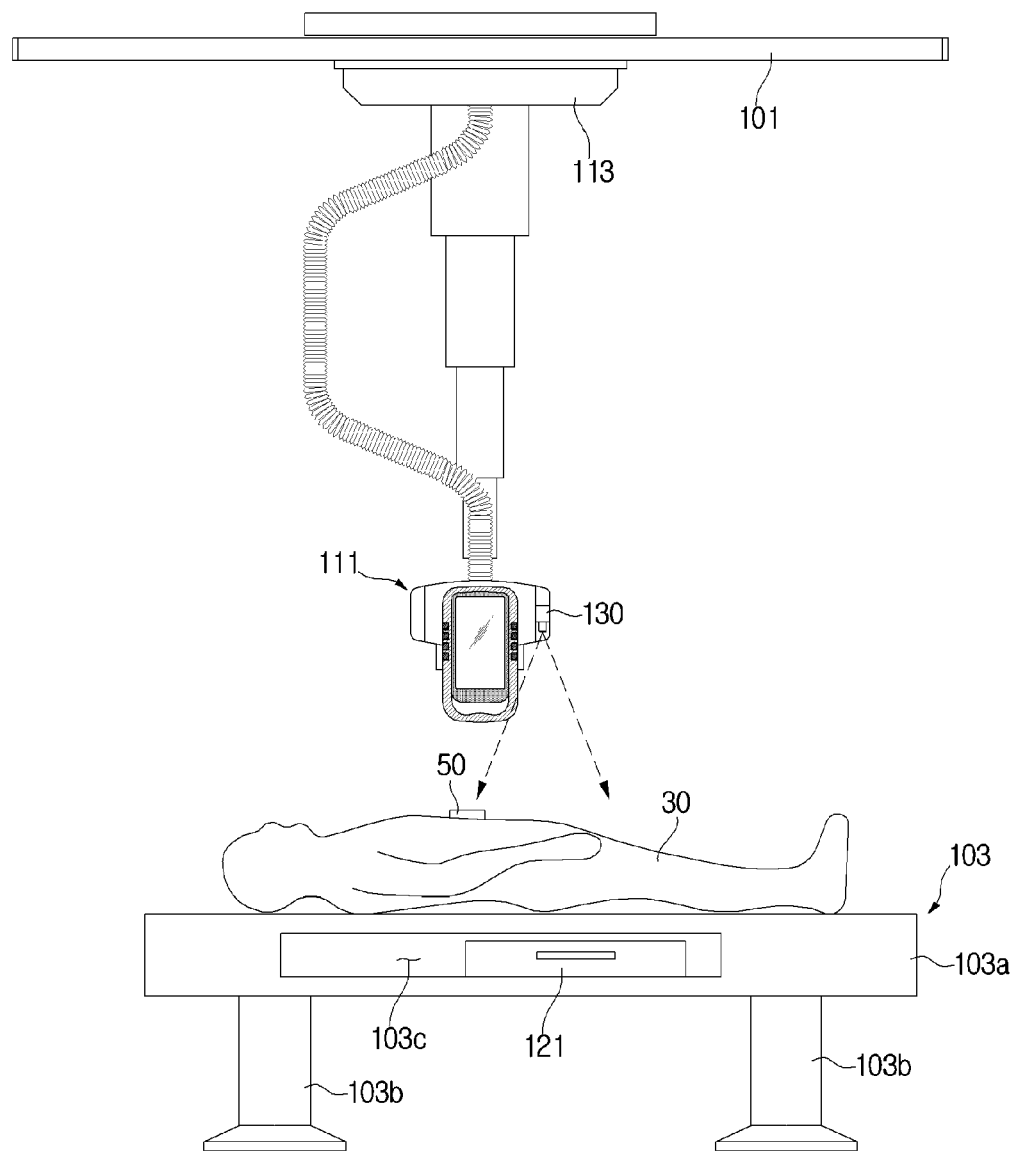
FIG. 8 is a diagram which illustrates an appearance of an X-ray imaging apparatus in a case in which a normal camera is used as an imaging unit instead of a wide-angle camera, according to an exemplary embodiment.
Figure 9:
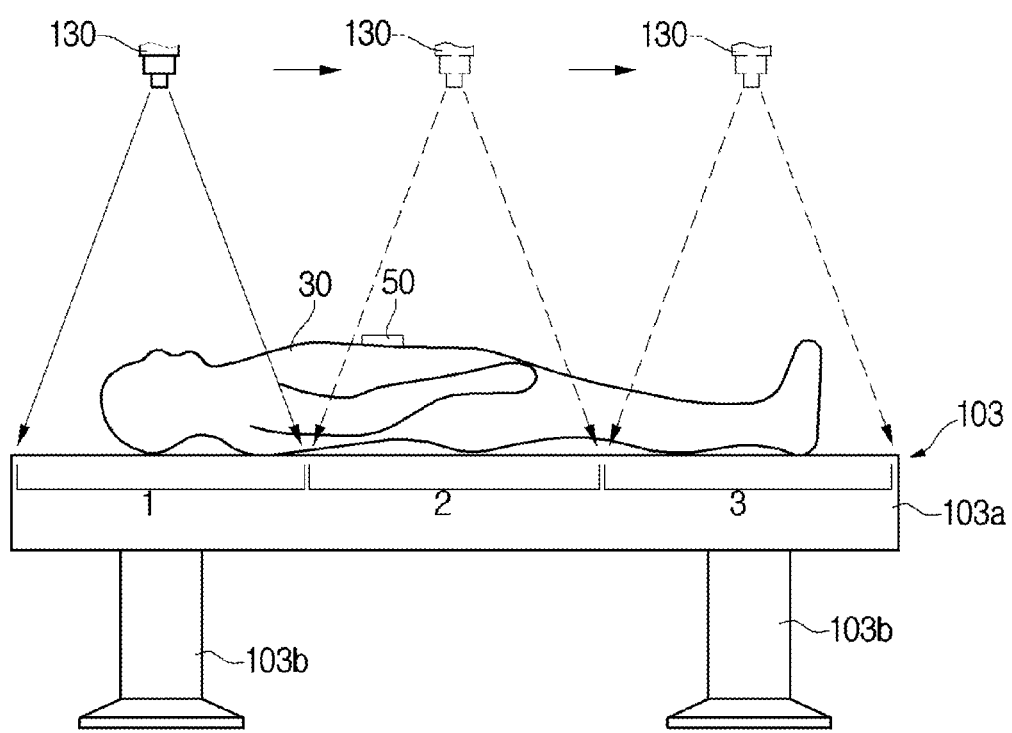
FIG. 9 is a diagram which illustrates a method for generating an image of a subject in a case of using a normal camera.

FIG. 8 is a diagram which illustrates an appearance of an X-ray imaging apparatus in a case in which a normal camera is used as an imaging unit instead of a wide-angle camera according to an exemplary embodiment, and FIG. 9 is a diagram which illustrates a method for generating an image of a subject in a case of using a normal camera.

Although the imaging unit 130 is implemented by a wide-angle camera which is usable for generating an image of the upper plate 103a of the patient table 103 in the above-described exemplary embodiment, the imaging unit 130 may be implemented by a normal camera having a normal lens mounted therein. If the imaging unit 130 is implemented by a normal camera, as shown in FIG. 8, a portion of the upper plate 103a of the patient table 103 or the subject 30 may be imaged in a single stage.

Accordingly, as shown in FIG. 9, while the imaging unit 130 is being moved, segmentation imaging of the upper plate 103a is performed. The number of times of imaging varies based on an angle of view and the length of the upper plate 103a and, for example, if the angle of view of the imaging unit 130 covers one third of the upper plate 103a, as shown in FIG. 9, the imaging unit 130 performs imaging three times while the imaging unit 130 is moved in the longitudinal direction of the upper plate 103a, i.e., the horizontal direction.

If the imaging unit 130 is mounted in the X-ray tube 111, the imaging unit 130 may be moved by moving the X-ray tube 111 and, if the imaging unit 130 is not mounted in the X-ray tube 111, the imaging unit may be moved by using a movable support.

Figure 10A:
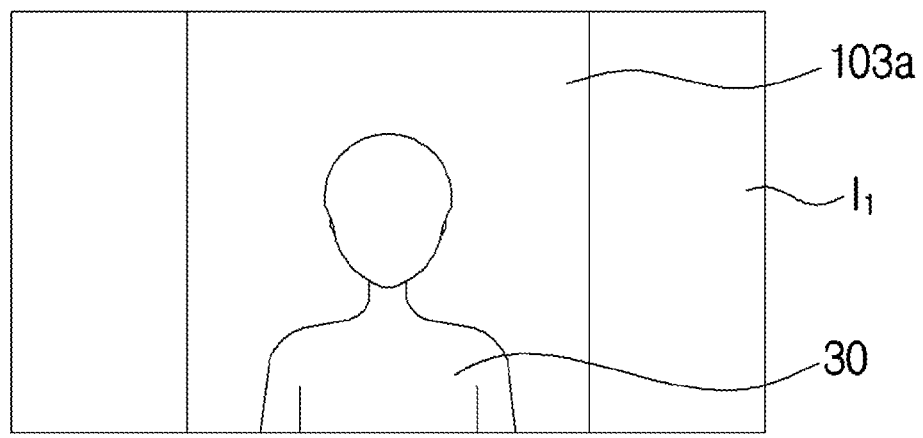
Figure 10B:
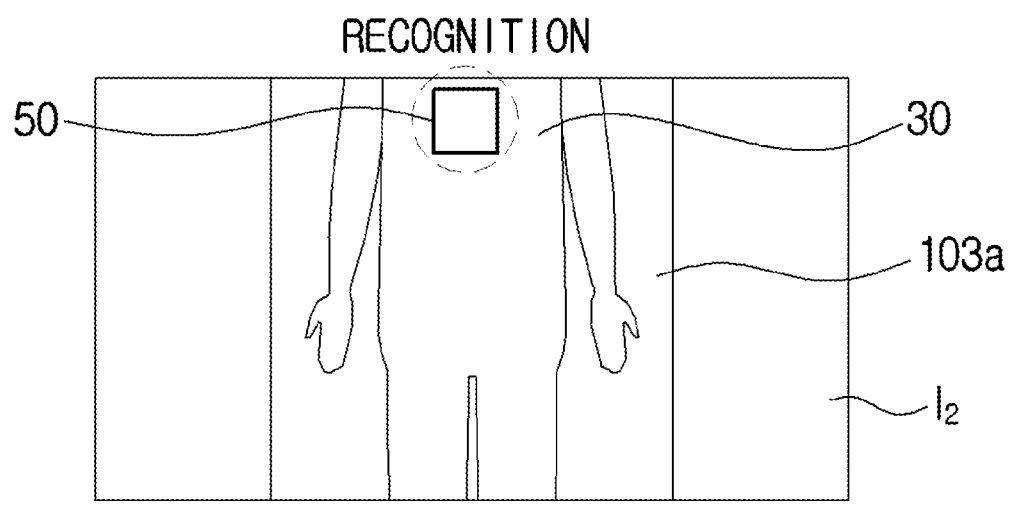
Figure 10C:
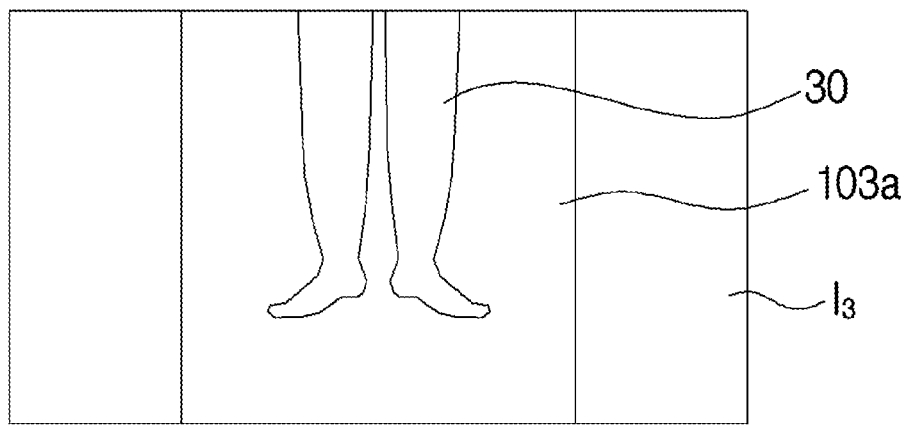

FIGS. 10A, 10B, and 10C are diagrams which illustrate a recognition of a marker 50 from an image of a subject, which image is formed by using the method shown in FIG. 9.

If imaging is performed by using the method shown in FIG. 9, a subject image $I_1$ of a region 1 of FIG. 9, a subject image $I_2$ of a region 2, and a subject image $I_3$ of a region 3 are acquired. If the subject images are transmitted to the marker recognizer 140, the marker recognizer 140 recognizes the marker 50 by using pre-stored information relating to a particular feature of the marker 50 with respect to the subject images $I_1$, $I_2$ and $I_3$ as shown in FIGS. 10A, 10B, and 10C.

Alternatively, the imaging unit 130 transmits the image of the subject which is generated during movement to the marker recognizer 140 in real time in order to recognize the marker in real time. With reference to FIGS. 9, 10A, and 10B, the imaging unit 130 images the region 1 and transmits the image to the marker recognizer 140, the marker recognizer 140 searches for a marker having the feature which corresponds to the pre-stored information in the subject image $I_1$, and the imaging unit 130 is moved to image the region 2 if the marker is not present in the subject image $I_1$. The subject image $I_2$ is transmitted to the marker recognizer 140 and the marker recognizer 140 recognizes the marker 50 having the feature which corresponds to the pre-stored information from the subject image $I_2$. Because the marker 50 is present in the subject image $I_2$, the imaging unit 130 is stopped, and the result of the recognition is transmitted to the position controller 150.

The position calculator 151 calculates the position of the marker 50 in the subject image $I_2$ and the control amount calculator 152 calculates a control amount for causing each of the X-ray tube 111 and the X-ray detector 121 to be moved to the respective positions which correspond to the marker 50. Position calculation and control amount calculation have been described above, and the control amount may be calculated in consideration of the relative position between the space of each subject image subjected to segmentation imaging and the imaging unit 130.

Figure 11:
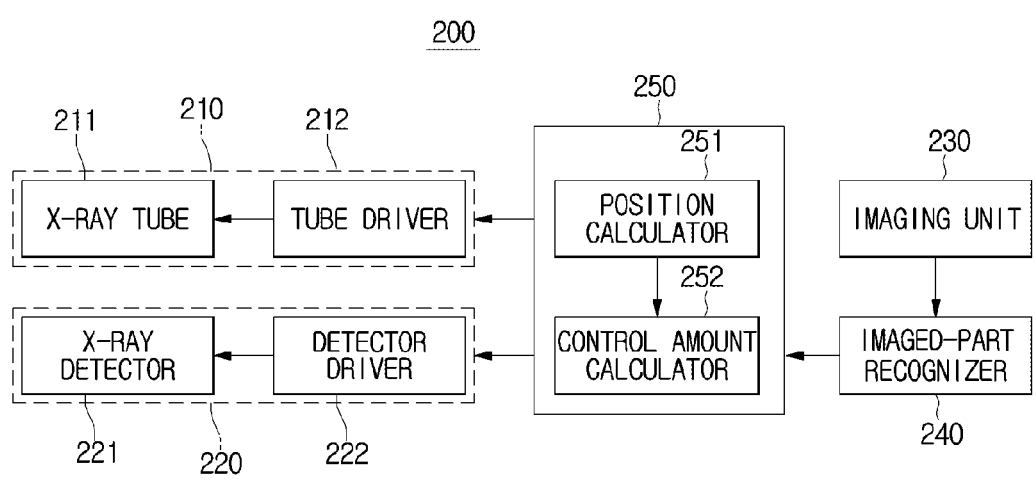
FIGS. 11 and 12 are block diagrams which illustrate an X-ray imaging apparatus which recognizes a part to be subjected to X-ray imaging, according to another exemplary embodiment.
Figure 12:
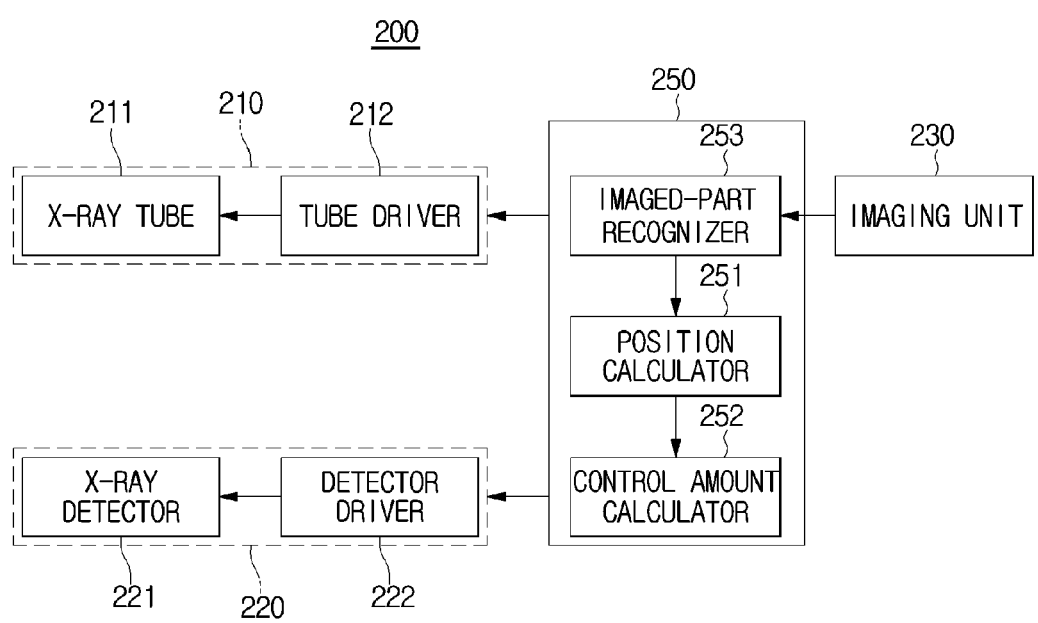
Figure 13:
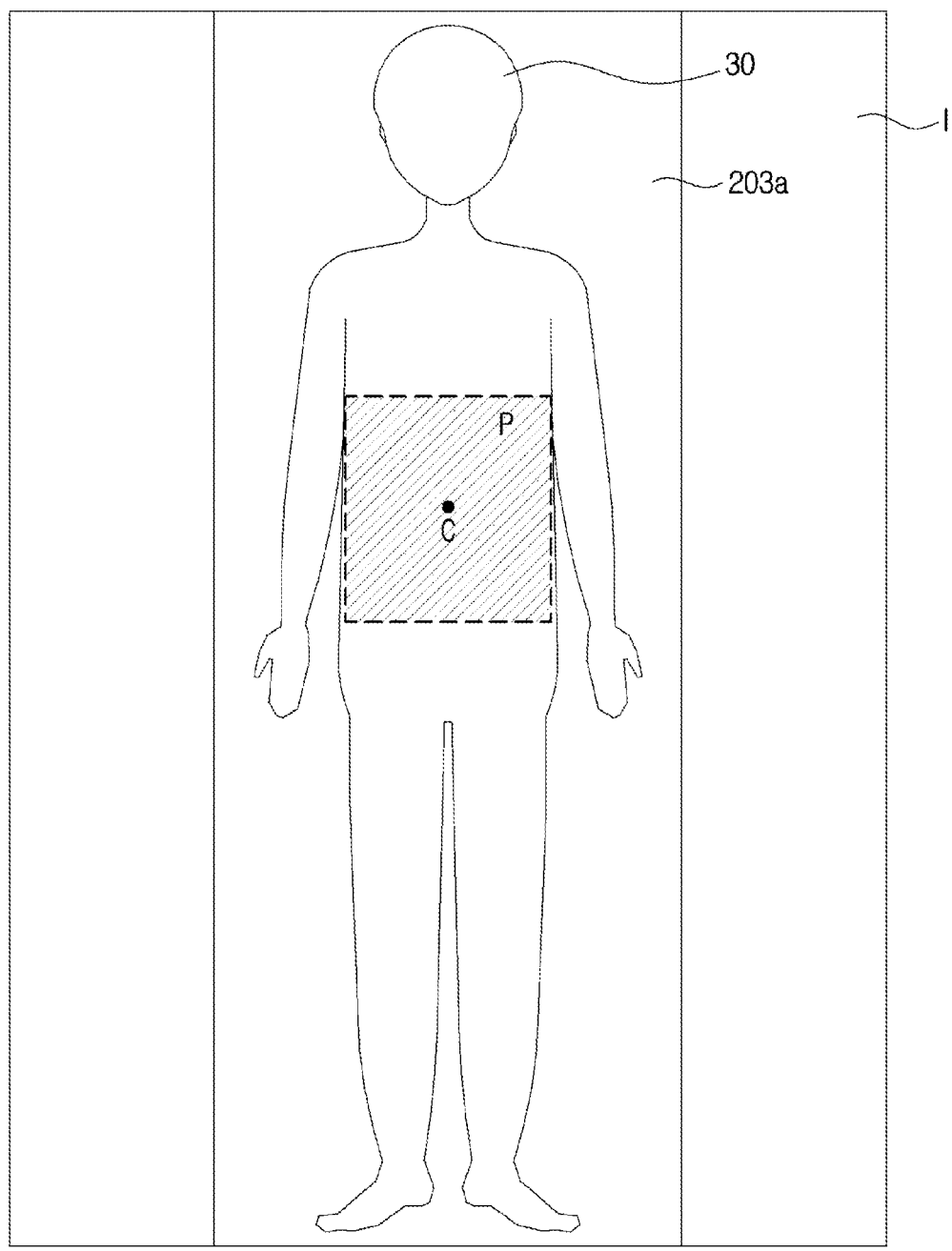
FIG. 13 is a diagram which illustrates a recognition of a part to be subjected to X-ray imaging from an image of a subject.

FIGS. 11 and 12 are block diagrams which illustrate an X-ray imaging apparatus which recognizes a part to be subjected to X-ray imaging, according to another exemplary embodiment, and FIG. 13 is a diagram which illustrates a recognition of a part to be subjected to X-ray imaging from an image of a subject.

Referring to FIG. 11, the X-ray imaging apparatus 200 according to another exemplary embodiment includes an X-ray tube unit 210 which generates and radiates X-rays toward a subject, an X-ray detection unit 220 which detects X-rays which propagate through the subject, an imaging unit 230 which generates an image of the subject, an imaged-part recognizer which analyzes the image of the subject which is generated by the imaging unit 230 and which recognizes a part to be subjected to X-ray imaging, and a position controller 250 which includes a position calculator 251 and a control amount calculator 252 and which matches the respective positions of each of an X-ray tube 211 and an X-ray detector 221 with the position of the part to be subjected to X-ray imaging.

Although the X-ray imaging apparatus 100 indirectly recognizes the part to be subjected X-ray imaging by using the marker as described above with respect to the exemplary embodiment illustrated in FIG. 2, the X-ray imaging apparatus according to the present exemplary embodiment directly recognizes the part to be subjected to X-ray imaging.

The X-ray tube unit 210, the X-ray detection unit 220 and the imaging unit 230 have been described above with respect to the above-described exemplary embodiment. Hereinafter, an operation of the imaged-part recognizer 240 and the position controller 250 will be described.

Referring also to FIG. 13, if the imaging unit 230 employs a wide-angle camera, generates an image of the subject in a state in which the subject 30 lies on the patient table 203a and transmits the image of the subject to the imaged-part recognizer 240, the imaged-part recognizer 240 finds and recognizes the part P to be subjected to X-ray imaging, as shown in FIG. 11. At this time, the imaged-part recognizer 240 may use at least one of various object recognition algorithms, pre-store information relating to a feature which indicates the part P to be subjected to X-ray imaging, and recognize a region having the feature to which the pre-sored information relates.

The feature which indicates the part P to be subjected to X-ray imaging may include an overall shape of the part to be subjected to X-ray imaging and a physical feature of the part to be subjected to X-ray imaging. For example, if the part to be subjected to X-ray imaging is an arm, a leg or a head, the feature which indicates the part P to be subjected to X-ray imaging may be the shape of the arm, the leg or the head, or the position of the arm, the leg or the head with respect to the subject 30. The imaged-part recognizer 240 recognizes a region having a feature to which the pre-stored information relates from the subject image, and the position calculator 251 calculates the position of the center of the recognized region.

The control amount calculator 252 calculates a control amount for causing each of the X-ray tube 211 and the X-ray detector 221 to be moved to a respective position which corresponds to the part P to be subjected to X-ray imaging. For calculation of the control amount, information relating to the relative position between the X-ray tube 211 and the subject image I and information relating to the relative position of the X-ray detector 221 and the subject image I may be pre-stored. In particular, the actual positions of the X-ray tube and the X-ray detector as expressed with respect to the coordinate system of the subject image I may be pre-stored.

The control amount calculator 252 may acquire the respective target positions of each of the X-ray tube 211 and the X-ray detector 221 based on the stored relative position information, and then calculate the control amount for causing each of the X-ray tube 211 and the X-ray detector 221 to be moved to the respective target positions. The target positions of the X-ray tube 211 and the X-ray detector 221, more particularly, the positions which respectively correspond to the part to be subjected to X-ray imaging, may be the positions where the center of the X-ray radiation region of the X-ray tube 211 and the center of the detection region of the X-ray detector 221 match the part to be subjected to X-ray imaging or the center of the part to be subjected to X-ray imaging in a two-dimensional space.

As an example, the control amount for causing each of the center of the X-ray radiation region of the X-ray tube 211 and the center of the detection region of the X-ray detector 221 to match with the center C of the part P to be subjected to X-ray imaging may be calculated.

However, the position calculator 251 may not calculate the position of the center of the part P to be subjected to X-ray imaging. More specifically, if the size of the part P to be subjected to X-ray imaging is equal to or greater than a predetermined size, a portion of the part to be subjected to X-ray imaging may not be imaged when the centers of the X-ray radiation region and the X-ray detection region do not match the center of the center of the part P to be subjected to X-ray imaging. Accordingly, although the position of any portion of the regions of the part P to be subjected to X-ray imaging may be calculated if the size of the part P to be subjected to X-ray imaging is less than the predetermined size, the position of the center of the part P to be subjected to X-ray imaging is calculated if the size of the part P to be subjected to X-ray imaging is equal to or greater than the predetermined size.

As another example, if the part P to be subjected to X-ray imaging is an abdomen, the imaged-part recognizer 240 may recognize a navel of the subject image I as a feature, the position calculator 251 may calculate the position of the navel, and the control amount calculator 252 may calculate a control amount for causing each of the X-ray tube 211 and the X-ray detector 221 to be moved to a respective position which corresponds to the navel and then transmit the calculated control amount to the tube driver 212 and the detector driver 222.

The imaged-part recognizer 240 and the controller 250 may include a memory in which a program capable of performing respective operations and data necessary for executing the program are stored and a processor configured to execute the stored program. The marker recognizer 240 and the controller 250 may use a separate processor or memory. Alternatively, as illustrated in FIG. 12, the imaged-part recognizer 253 may be included as a component of the controller 250. In this case, the position calculator 251, the control amount calculator 252 and the imaged-part recognizer 253, which are components of the controller 250, may also use a separate processor or memory, and share the processor and the memory.

Although the X-ray tube 11a and the X-ray detector 12a are fixed during X-ray imaging in the X-ray imaging apparatus 10 according to the above-described embodiment, the exemplary embodiment is not limited thereto. An X-ray imaging apparatus 20 according to another exemplary embodiment may be implemented by a computed tomography (CT) device in which an X-ray tube and an X-ray detector are mounted in a gantry and rotated.

Figure 14:
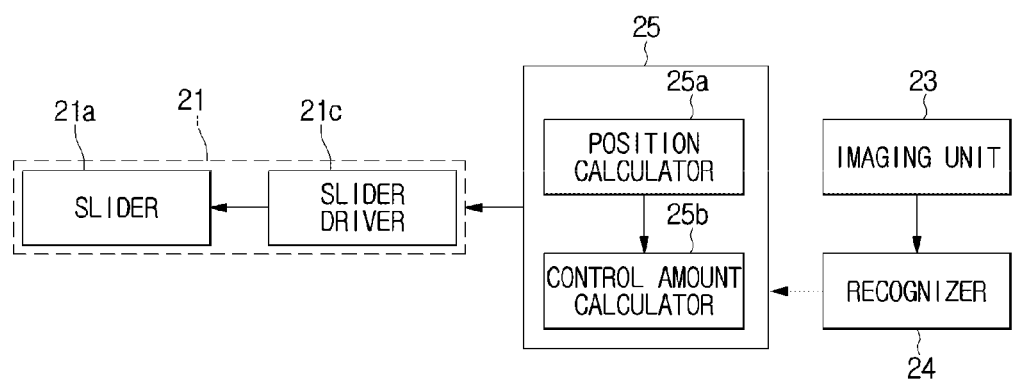
FIG. 14 is a block diagram which illustrates an X-ray imaging apparatus, according to another exemplary embodiment.

FIG. 14 is a block diagram which illustrates an X-ray imaging apparatus according to another exemplary embodiment.

Referring to FIG. 14, the X-ray imaging apparatus 20 according to another exemplary embodiment includes an imaging unit 23 which generates an image of a subject, a marker recognizer 24 which recognizes a marker in the image of the subject, a position controller 25 which determines a part to be subjected to X-ray imaging and controls the position of a slider 21a such that the marker is located between an X-ray tube and an X-ray detector, and a patient table 21 which is controlled by the position controller 25.

If the imaging unit 23 generates an image of the subject and transmits the image of the subject to the recognizer 24, the recognizer 24 recognizes the part to be subjected to X-ray imaging from the image of the subject. In recognition of the part to be subjected to X-ray imaging, the part to be subjected to X-ray imaging or a marker located at the part to be subjected to X-ray imaging may be recognized. If the recognizer 24 transmits the result of the recognition to the position controller 25, the position calculator 25a of the position controller 25 calculates the position of the recognized marker or the part to be subjected to X-ray imaging, and the control amount calculator 25b calculates a control amount for causing the marker or the part to be subjected to X-ray imaging to be positioned between the X-ray tube and the X-ray detector. The calculated control amount is transmitted to a slider driver 21c, which is implemented by a driving device, such as, for example, a motor.

Hereinafter, an exemplary embodiment of an X-ray imaging apparatus for recognizing a marker and an exemplary embodiment of an X-ray imaging apparatus for recognizing a part to be subjected to X-ray imaging will be described.

Figure 15:
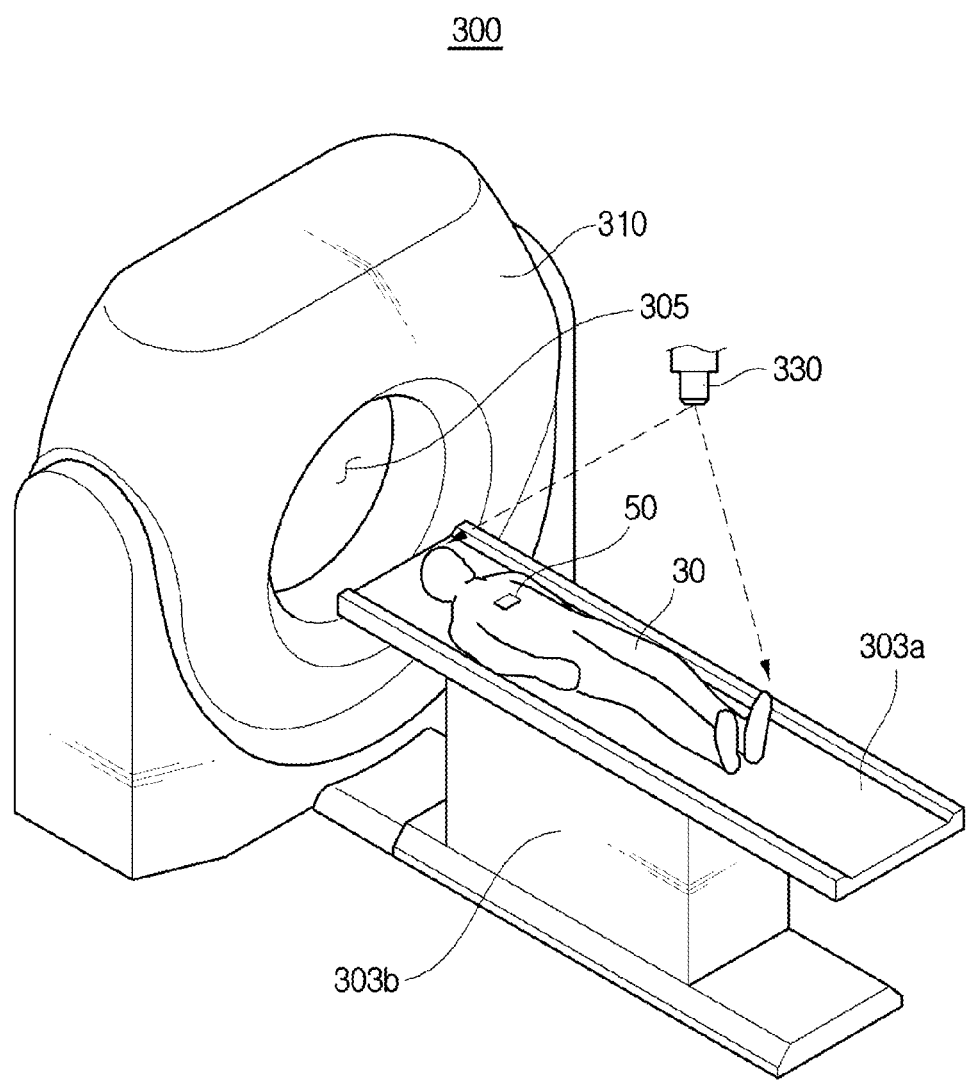
FIG. 15 is a diagram which illustrates an appearance of an X-ray imaging apparatus in a case of using a marker, according to another exemplary embodiment.
Figure 16:
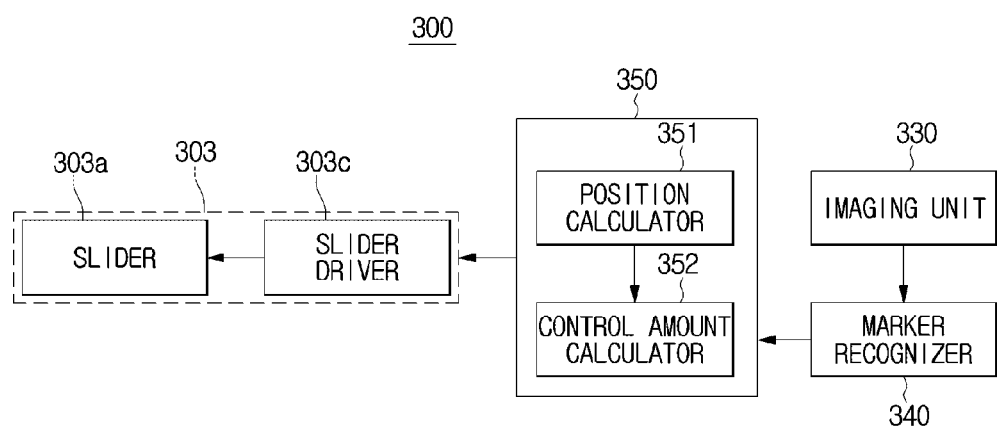
FIGS. 16 and 17 are block diagrams which illustrate an X-ray imaging apparatus in a case of using a marker, according to another exemplary embodiment.
Figure 17:
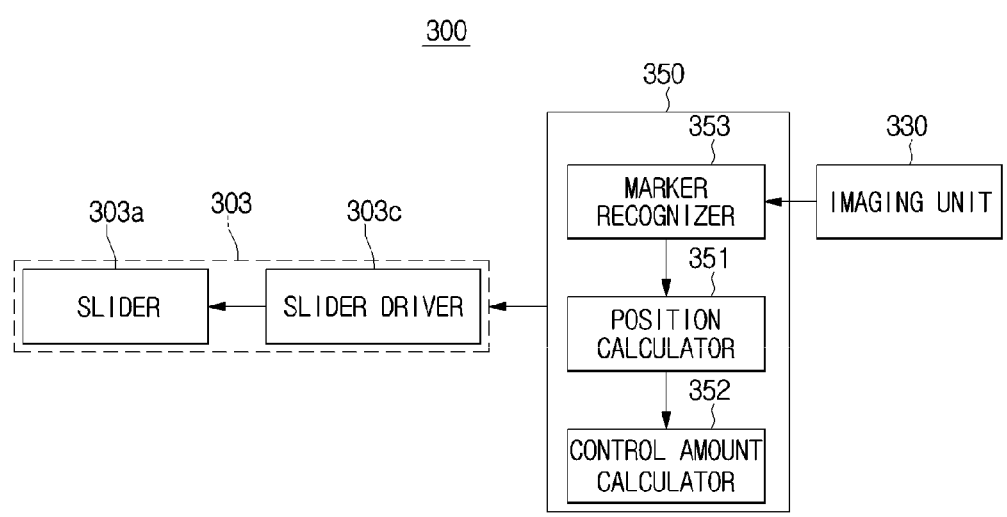

FIG. 15 is a diagram which illustrates an appearance an X-ray imaging apparatus according to another exemplary embodiment in a case of using a marker, and FIGS. 16 and 17 are block diagrams which illustrate an X-ray imaging apparatus according to another exemplary embodiment in a case of using a marker.

Referring to FIG. 15, an X-ray tube and an X-ray detector of the X-ray imaging apparatus 300 are mounted in a gantry of a housing 310 and are rotated. The patient table 303 includes a slider 303a supported by a support 303b, and the slider 303a is a bed on which a subject 30 lies and is movable into a bore 305. The X-ray imaging apparatus 300 moves the slider 303a into the bore 305 when the subject 30 lies on the slider 303a, and locates the part to be subjected to X-ray imaging between the X-ray tube and the X-ray detector.

Although a user may directly control the position of the slider 303a, the X-ray imaging apparatus 300 according to another exemplary embodiment automatically moves the slider 303a to a target position.

Referring to FIG. 16, the X-ray imaging apparatus 300 includes an imaging unit 330 which generates an image of a subject, a marker recognizer 340 which recognizes a marker from the image of the subject, a position controller 350 which calculates the position of the marker and controls the position of the slider 303a such that the position of the marker on the slider 303a is located between an X-ray tube and an X-ray detector, and a patient table 303.

Although the imaging unit 330 may be implemented similarly as described above with respect to the imaging units 130 and 230 of the X-ray imaging apparatus 100 and 200 according to the above-described exemplary embodiments, the imaging unit 330 may not be mounted in the X-ray tube but may be mounted on one of the ceiling of an inspecting room and a predetermined support connected to one side of the patient table 303 or the housing 310. The position of the imaging unit 330 is purely exemplary and is not limited, provided that the imaging unit may image the slider 303a or the subject 30 on the slider before the slider 303a is inserted into the bore 305.

The image of the subject which is generated by the imaging unit 330 is transmitted to the marker recognizer 340, and the marker recognizer 340 recognizes the marker 50 which has a particular feature which corresponds to pre-stored information from the image of the subject. Marker type and marker recognition have been described above.

The position controller 350 includes a position calculator 351 and a control amount calculator 352. The position calculator 351 calculates the position of the recognized marker 50, and the control amount calculator 352 calculates a control amount which causes the slider 303a to be moved such that the position of the marker 50 on the slider 303a is located between the X-ray tube and the X-ray detector.

More specifically, the position calculator 351 calculates the position of the marker 50 on the slider 303a. As described above with reference to FIG. 7A, if the position of the marker 50 appearing in the subject image I on the slider 303a is calculated by using two-dimensional coordinates, a determination as to which point of the slider 303a is located between the X-ray tube and the X-ray detector may be made by the position of the marker. For example, if the position of the marker 50 is expressed as (m, n), the position (m, n) of the slider 303a is located between the X-ray tube and the X-ray detector for X-ray imaging.

The control amount calculator 352 calculates a control amount for causing the slider 303a of the patient table to be moved such that the position of the marker 50 matches the position of the X-ray tube 311 or the X-ray detector 321. For calculation of the control amount, information relating to the relative position between the slider 303a and the X-ray tube 311 or the X-ray detector 321 may be pre-stored. The control amount for causing the position of the marker 50 on the slider 303a to be matched with one of the center of the radiation region of the X-ray tube and the center of the detection region of the X-ray detector is calculated based on the stored relative position information. The calculated control amount is transmitted to the slider driver 303c, and the slider driver 303c drives the slider 303a based on the transmitted control amount.

Matching the position of the marker 50 on the slider 303a with the center of the radiation region of the X-ray tube or the center of the detection region of the X-ray detector is equivalent to matching the position of the marker 50 on the slider 303a with the center of the radiation region of the X-ray tube or the center of the detection region of the X-ray detector in a two-dimensional space.

The marker recognizer 340 and the controller 350 may include a memory in which a program capable of performing respective operations and data necessary for executing the program are stored and a processor configured to execute the stored program. The marker recognizer 340 and the controller 350 may use a separate processor or memory. Alternatively, as illustrated in FIG. 17, the marker recognizer 353 may be included as a component of the controller 350. In this case, the position calculator 351, the control amount calculator 352 and the marker recognizer 353, which are components of the controller 350, may also use a separate processor or memory, and share the processor and the memory.

Unlike the X-ray imaging apparatus 100 and 200 according to the above-described exemplary embodiments, because the X-ray imaging apparatus 300 according to the present exemplary embodiment is mounted in the gantry in a state in which the X-ray tube faces the X-ray detector, the position of the slider 303a may match the position of one of the X-ray tube and the X-ray detector.

Figure 18:
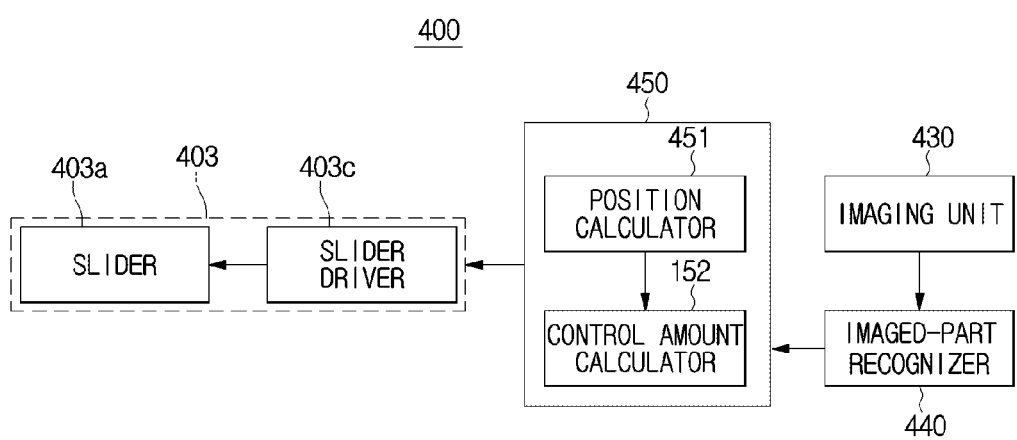
FIGS. 18 and 19 are block diagrams which illustrate an X-ray imaging apparatus which recognizes a part to be subjected to X-ray imaging, according to another exemplary embodiment.
Figure 19:
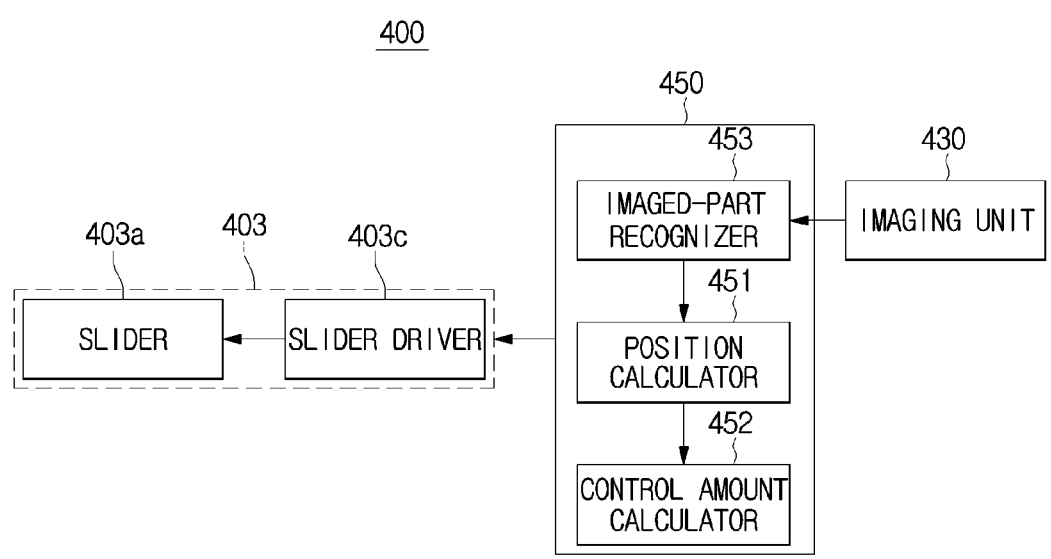

FIGS. 18 and 19 are block diagrams which illustrate an X-ray imaging apparatus which recognizes a part to be subjected to X-ray imaging, according to another exemplary embodiment. The appearance of the X-ray imaging apparatus 400 according to the present exemplary embodiment, the configuration and operation of the imaging unit 430 and the configuration and operation of the patient table 403 are equivalent to those of the above-described X-ray imaging apparatus 300.

An imaged-part recognizer 440 uses pre-stored information in order to recognize a part to be subjected to X-ray imaging from the image of the subject which is generated by the imaging unit 430. A description thereof is equivalent to the description of the exemplary embodiment illustrated in FIG. 14.

The position calculator 451 calculates the position of the recognized part to be subjected to X-ray imaging on the slider 303a. The position of the part to be subjected to X-ray imaging may be calculated as two-dimensional coordinates. The position of a portion other than the center of the part to be subjected to X-ray imaging may be calculated if the size of the part to be subjected to X-ray imaging is less than a predetermined size, and the position of the center of the part to be subjected to X-ray imaging is calculated if the size of the part to be subjected to X-ray imaging is equal to or greater than the predetermined size.

The control amount calculator 452 may pre-store information relating to the relative position between the slider 403a and the X-ray tube or the X-ray detector. A control amount for causing the position of the part to be subjected to X-ray imaging on the slider 403a to be matched with the center of the radiation region of the X-ray tube or the center of the detection region of the X-ray detector is calculated based on the stored relative position information. The calculated control amount is transmitted to the slider driver 403c, and the slider driver 403c drives the slider 403a based on the transmitted control amount.

The imaged-part recognizer 440 and the controller 450 may include a memory in which a program capable of performing respective operations and data necessary for executing the program are stored and a processor configured to execute the stored program. The imaged-part recognizer 440 and the controller 450 may use a separate processor or memory. Alternatively, as illustrated in FIG. 19, the imaged-part recognizer 453 may be included as a component the controller 450. In this case, the position calculator 451, the control amount calculator 452 and the imaged-part recognizer 453, which are components the controller 450, may also use a separate processor or memory, and share the processor and the memory.

Meanwhile, in the X-ray imaging apparatuses according to the above-described embodiments, the X-ray tube or the X-ray detector is movable, but is movable within a range in which the cartridge or the slider is movable. On the other hand, in a mobile X-ray imaging apparatus, a main body to which an X-ray tube is connected is freely movable, an arm on which an X-ray tube head is mounted provides multiple degrees of freedom, and a portable X-ray detector is implemented. Accordingly, the X-ray tube and the X-ray detector are freely movable. As degrees of freedom of the X-ray tube and the X-ray detector increase, complexity of orientation or position alignment thereof increases and more accurate control is required. According to another embodiment of the present invention, an orientation and a position of an X-ray tube of a mobile X-ray imaging apparatus may be aligned with an imaging target region. Detailed embodiments thereof will be described below.

Figure 20:
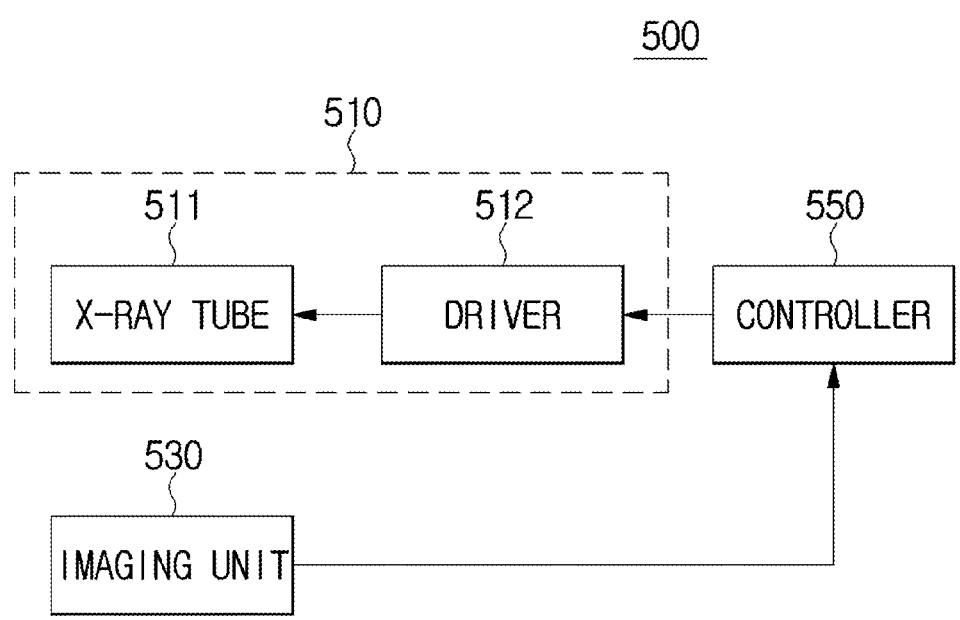
FIG. 20 is a control block diagram illustrating an X-ray imaging apparatus according to still another embodiment of the present invention.
Figure 21:
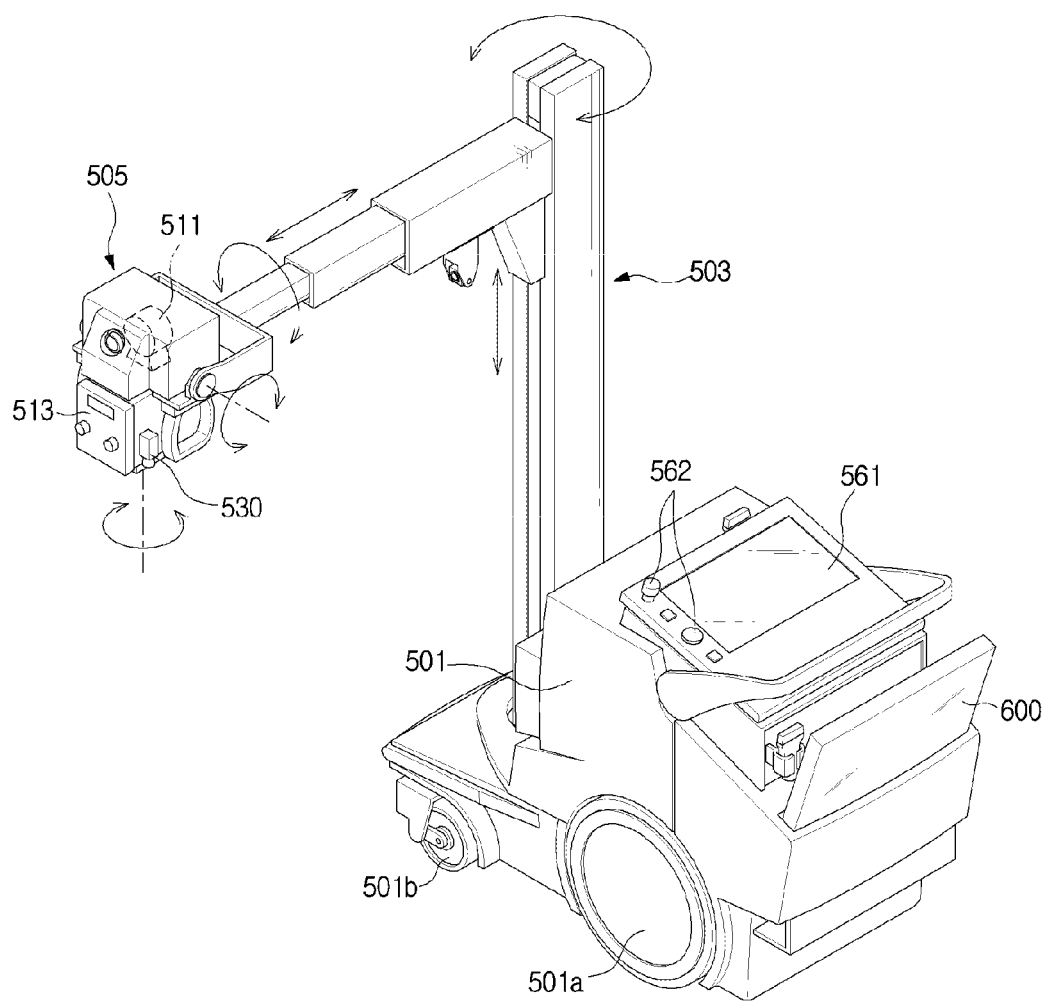
FIG. 21 is a diagram illustrating an exterior of an X-ray imaging apparatus according to still another embodiment of the present invention.

FIG. 20 is a control block diagram illustrating an X-ray imaging apparatus according to still another embodiment of the present invention. FIG. 21 is a diagram illustrating an exterior of an X-ray imaging apparatus according to still another embodiment of the present invention.

As illustrated in FIG. 20, an X-ray imaging apparatus 500 includes an X-ray tube unit 510 configured to generate X-rays and radiate the X-rays to the subject, an imaging unit 530 configured to image an image of the subject, and a controller 550 configured to recognize a marker positioned in an imaged part of the subject or the imaged part and align an orientation or a position of an X-ray tube 511 with the marker or the imaged part.

The X-ray tube unit 510 includes a driver 512 configured to provide power for moving the X-ray tube 511 and the X-ray tube 511. The driver 512 may include a plurality of motors, and may further include an inverter configured to supply converted power to the motor and a drive circuit configured to output a driving signal to the inverter. The motor converts power supplied from the inverter into mechanical energy to generate a rotational force, and the rotational force of the motor serves as power for moving the X-ray tube 511.

As illustrated in FIG. 21, the mobile X-ray imaging apparatus 500 may be implemented. Specifically, the X-ray tube 511 and a collimator 513 may constitute an X-ray tube head 505, and the X-ray tube head 505 may be supported by a tube arm 503 connected to a movable main body 501.

The collimator 513 is positioned in front of a window of the X-ray tube 511 and may regulate an X-ray radiation field. When the X-ray radiation field decreases, scattering X-rays may decrease. Therefore, based on information on a distance, a relative angle between the X-ray tube 511 and an X-ray detector module 600 and the like, an optimal X-ray radiation field may be determined.

Wheels 501a and 501b are mounted on the main body 501 and enable the X-ray imaging apparatus 500 to be easily moved. A display unit 561 configured to display a screen related to control of the X-ray imaging apparatus 500 and an input unit 562 configured to receive a control command from the user may be integrally provided.

The display unit 561 may be implemented by at least one of various display components such as a liquid crystal display (LCD), a light emitting diode (LED), an organic light emitting diode (OLED), a plasma display panel (PDP), and a cathode-ray tube (CRT). The input unit 562 may be implemented by at least one of input devices such as a keyboard, a mouse, a trackball, and a touch pad.

The X-ray detector module 600 may be implemented in a portable type separate from the X-ray imaging apparatus 500. However, for convenience of movement, a holder is provided in the main body 501 of the X-ray imaging apparatus 500 to accommodate the X-ray detector module 600 therein.

Similar to the above-described embodiment, the imaging unit 530 may be implemented by a camera that is a general imaging device such as a CCD camera and a CMOS camera. Also, the imaging unit 530 may image a still image or a video. The imaging unit 530 may image the subject in real time. The imaged image of the subject may be delivered to the controller 550 in real time or displayed on the display unit 561.

As an example, the imaging unit 530 may be mounted on the X-ray tube head 505, but as long as an initial relative position between the imaging unit 530 and the X-ray tube 511 is defined in advance, a position of the imaging unit 530 is not limited. However, the imaging unit 530 will be described in the following embodiment as being mounted on the collimator 513.

The X-ray tube 511 may move according to movement of the tube arm 503, and the tube arm 503 may include a plurality of subarms and be designed to provide a high degree of freedom. Hereinafter, control of a position and an orientation of the tube arm 503 will be described with reference to FIG. 18.

Figure 22:
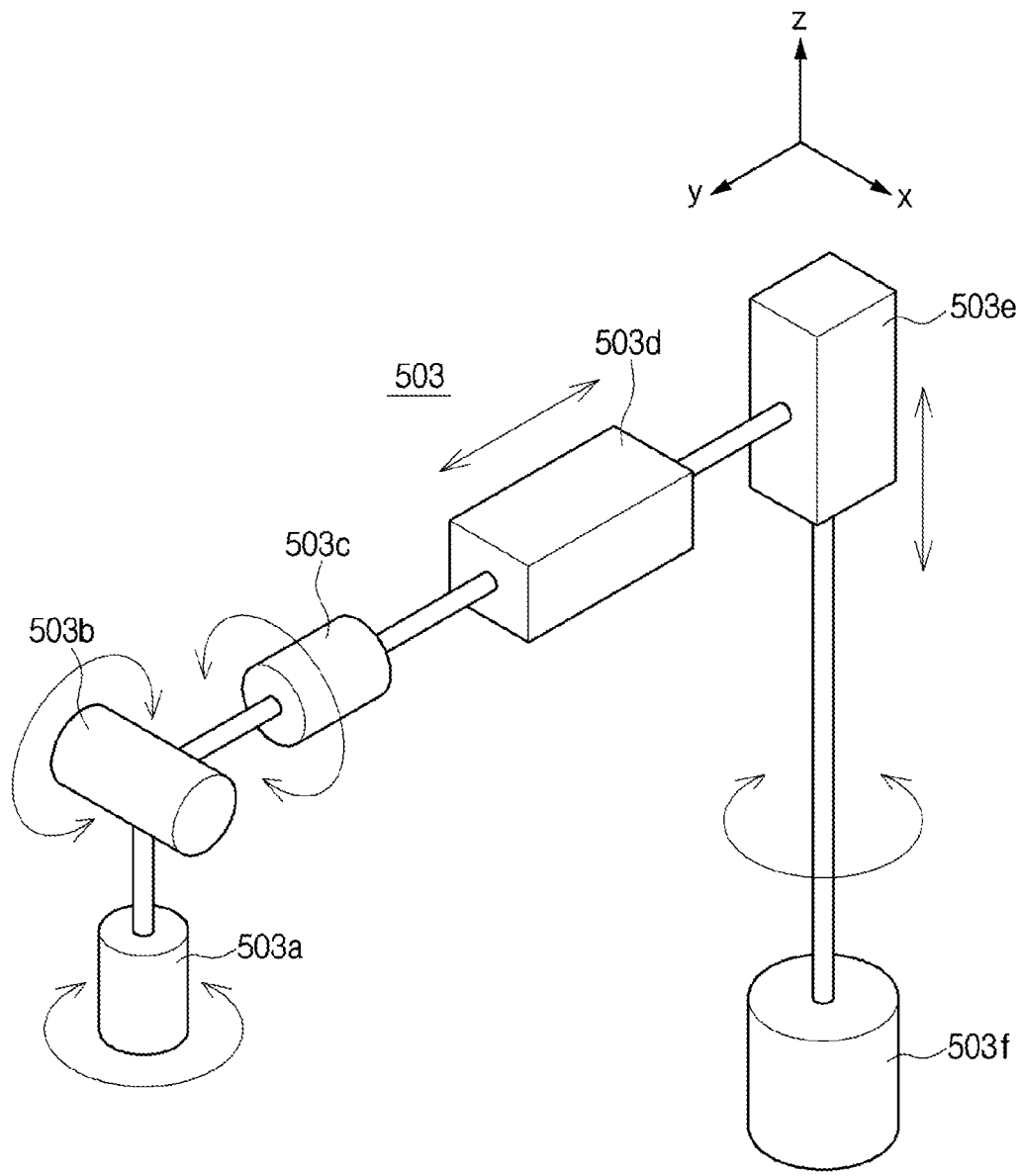
FIG. 22 is a diagram illustrating an example of a plurality of subarms constituting a tube arm.

FIG. 22 is a diagram illustrating an example of a plurality of subarms constituting a tube arm.

As exemplified in FIG. 22, the tube arm 503 may include six subarms. A 3D space in which the X-ray imaging apparatus 500 is positioned may be defined by an x axis, a y axis and a z axis. According to rotational movement or linear movement of each of the subarms, the X-ray tube 511 may perform rotational movement of yaw, pitch and roll, and linear movement in an x axis, y axis or z axis direction in a body coordinate system based on movement of the tube arm 503 or an absolute coordinate system. Meanwhile, a roll angle, a pitch angle and a yaw angle, which are relative angles based on the body coordinate system, may be converted into a roll angle, a pitch angle and a yaw angle, which are absolute angles based on the absolute coordinate system, respectively. In a general X-ray imaging apparatus, a reference of the absolute coordinates may be positioned at a fixed part of the X-ray imaging apparatus, and may be positioned at a part of the main body connected to the tube arm in the mobile X-ray imaging apparatus. Also, in both cases, a reference of the absolute coordinates may be positioned at a part of the X-ray detector. The embodiment of the X-ray imaging apparatus 500 may be based on either the body coordinate system or the absolute coordinate system. However, in the following embodiment, description will be provided based on the body coordinate system.

When the body coordinate system is used as the reference, a first subarm 503a is connected to the X-ray tube head 505 and is able to perform rotational movement (yaw movement) around a z axis, and a second subarm 503b connects the first subarm 503a and a third subarm 503c and is able to perform rotational movement (pitch movement) around an x axis. Also, the third subarm 503c connects the second subarm 503b and a fourth subarm 503d, and is able to perform rotational movement (roll movement) around a y axis, and the fourth subarm 503d connects the third subarm 503c and a fifth subarm 503e and is able to perform linear movement in a y axis direction. Also, a sixth subarm 503f is connected to the main body 501 and is able to perform rotational movement (yaw movement) in a z axis direction, and the fifth subarm 503e connects the sixth subarm 503f and the fourth subarm 503d and is able to perform linear movement in a z axis direction.

Meanwhile, according to yaw movement of the first subarm 503a, pitch movement of the second subarm 503b and roll movement of the third subarm 503c, an orientation of the X-ray tube 511 may be controlled. Here, the orientation of the X-ray tube 511 may refer to a direction of the X-ray tube 511, a direction of an X-ray beam radiated from the X-ray tube 511, or a relative angle between the X-ray tube 511 and the X-ray detector module 600. Also, according to linear movement in a y axis direction of the fourth subarm 503d, linear movement in a z axis direction of the fifth subarm 503e, and yaw movement of the sixth subarm 503f, a position of the X-ray tube 511 may be controlled.

Therefore, according to the tube arm 503 including six subarms, the X-ray tube 511 may be positioned at any point in the 3D space. In this case, a position of the X-ray tube 511 may be automatically controlled by the controller 550 and some control may be manually performed by the user's manipulation, and thus control may be performed semi-automatically. Specific examples of automatic control and semi-automatic control will be described below.

Figure 23:
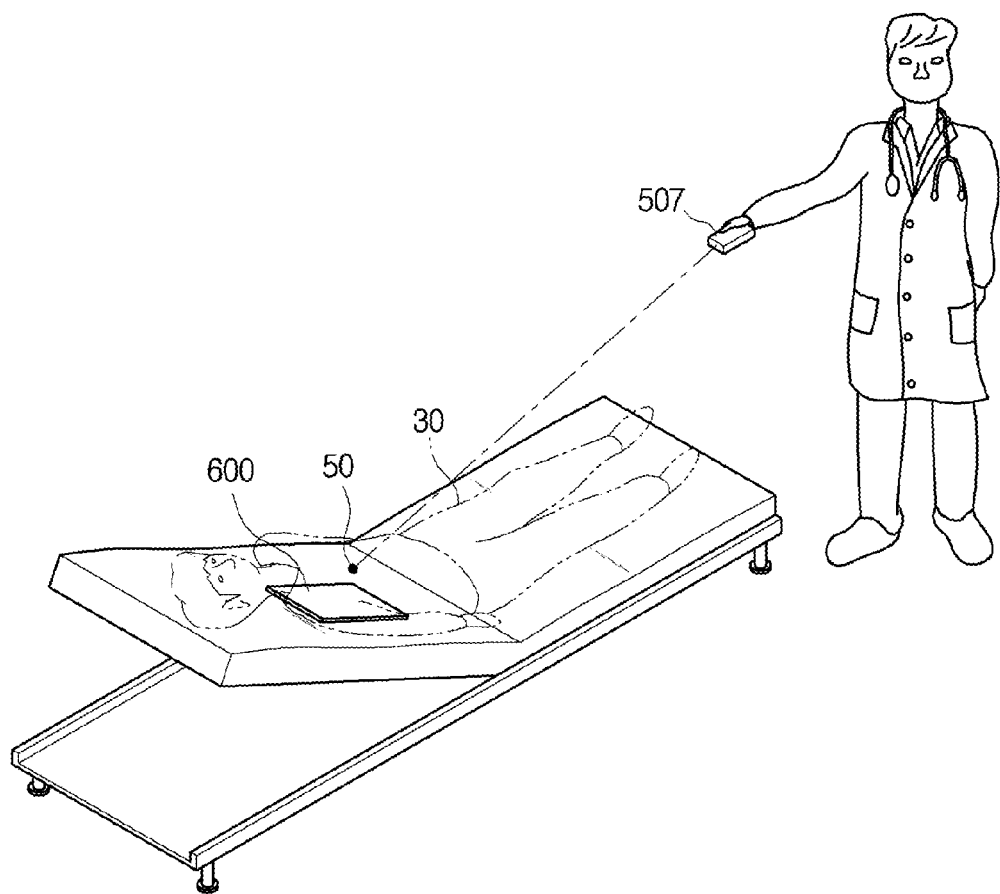
FIG. 23 is a diagram illustrating an example in which a marker is displayed on an imaged part of a subject.

FIG. 23 is a diagram illustrating an example in which a marker is displayed on an imaged part of a subject.

The position of the X-ray tube 511 may be controlled to a position corresponding to an imaged part of the subject, and the imaged part of the subject may be displayed by the marker, similar to the above-described embodiment. As exemplified in FIG. 23, the marker may be a spotlight radiated from a light source 507, and the light source 507 may be mounted on a hand switch configured to receive a start or end command of X-ray imaging from the user.

As illustrated in FIG. 23, when the portable X-ray detector module 600 is positioned in a back surface of the imaged part of the subject and the user displays the spotlight on the imaged part, the position and the orientation of the X-ray tube 511 may be aligned with the imaged part.

In the example of FIG. 23, the spotlight is used as the marker, but the embodiment of the X-ray imaging apparatus 500 is not limited thereto. It is needless to say that other markers used in the above-described embodiments may also be used in the embodiment of the X-ray imaging apparatus 500, and an embodiment in which the imaged part itself instead of the marker is recognized may also be applied to the X-ray imaging apparatus 500.

Figure 24B:
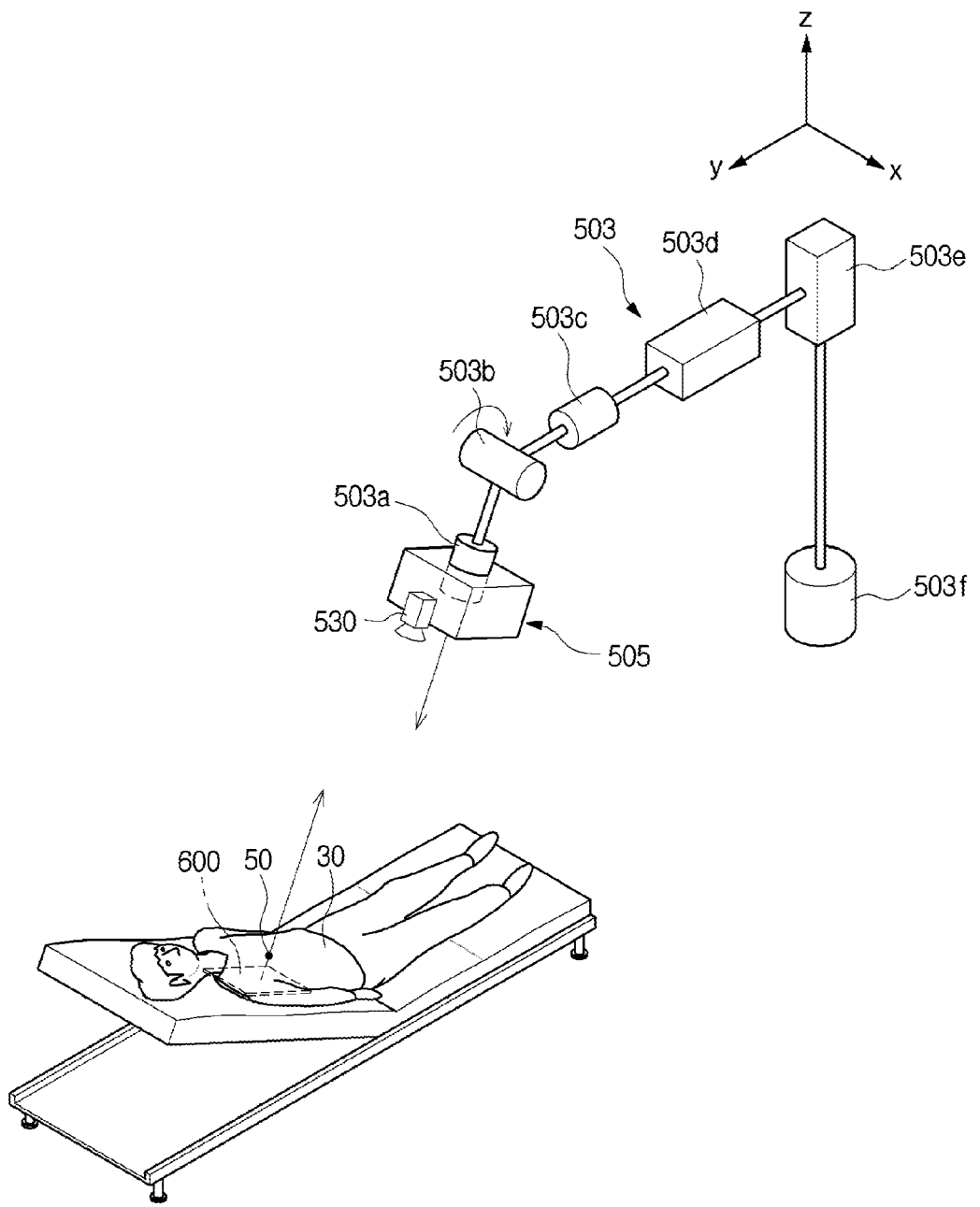
Figure 24C:
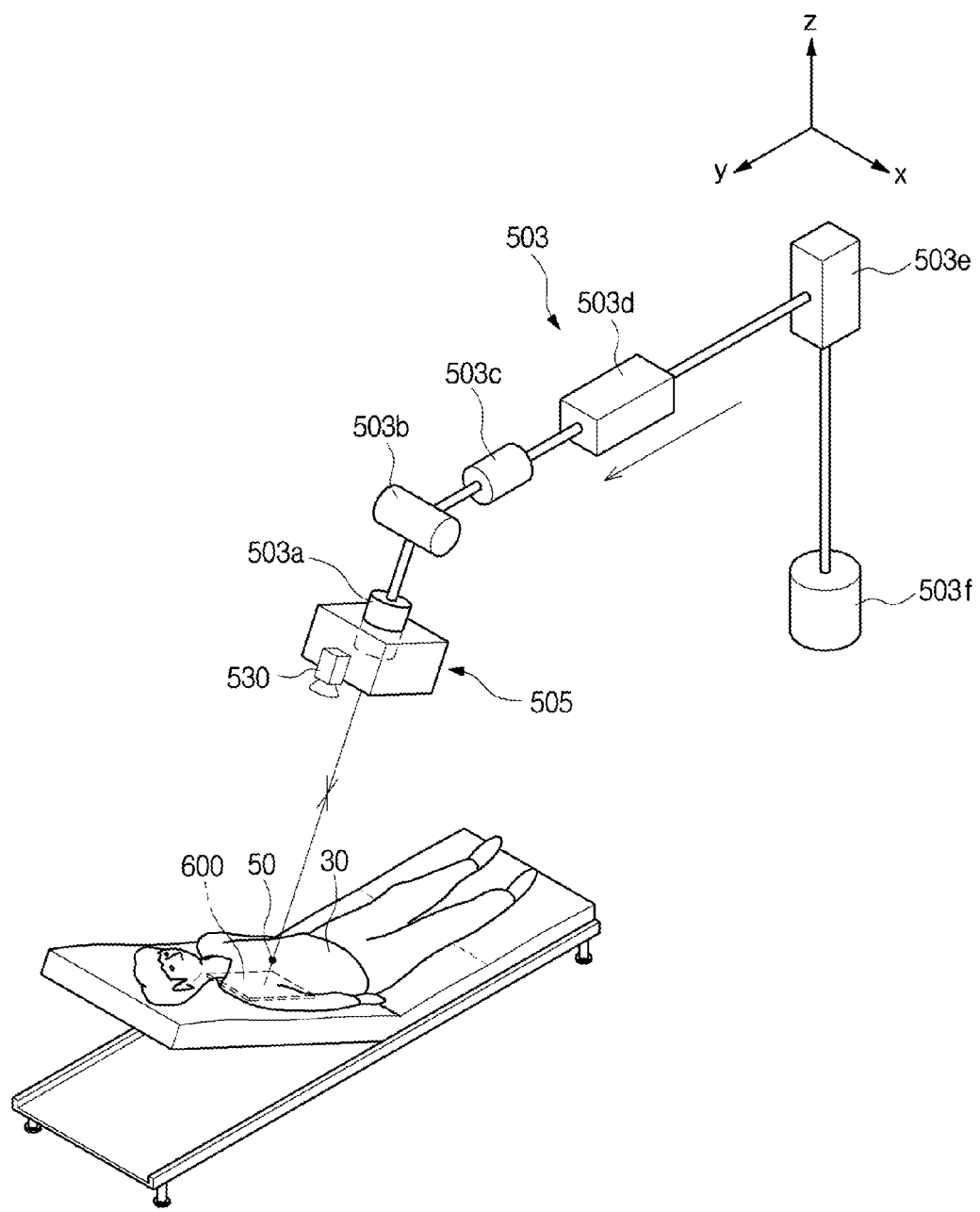

FIGS. 24A, 24B and 24C are diagrams schematically illustrating a process in which an orientation and a position of an X-ray tube are aligned.

As illustrated in FIGS. 24A, 24B and 24C, the first subarm 503a, the second subarm 503b and the third subarm 503c are rotationally moved so that the orientation of the X-ray tube 511 may be aligned with the imaged part or the X-ray detector module 600. For example, the X-ray detector module 600 and the X-ray tube 511 may be aligned in parallel to face each other.

Also, the fourth subarm 503d, the fifth subarm 503e and the sixth subarm 503f are linearly moved or rotationally moved so that the position of the X-ray tube 511 may be aligned with the imaged part. For example, the marker 50 may be aligned with a center of the X-ray tube 511.

In this case, the main body 501 is positioned adjacent to the subject, and the orientation and the position of the X-ray tube 511 may be appropriately aligned according to only the movement of the tube arm 503. The main body 501 may be manually moved by the user, and when a motor is mounted on the wheels 501a and 50b of the main body 501, may be automatically moved.

According to an example, the orientation of the X-ray tube 511 may be automatically aligned by the controller 550, and the position of the X-ray tube 511 may be manually aligned by the user. Hereinafter, details thereof will be described with reference to FIGS. 25 and 26.

Figure 25:
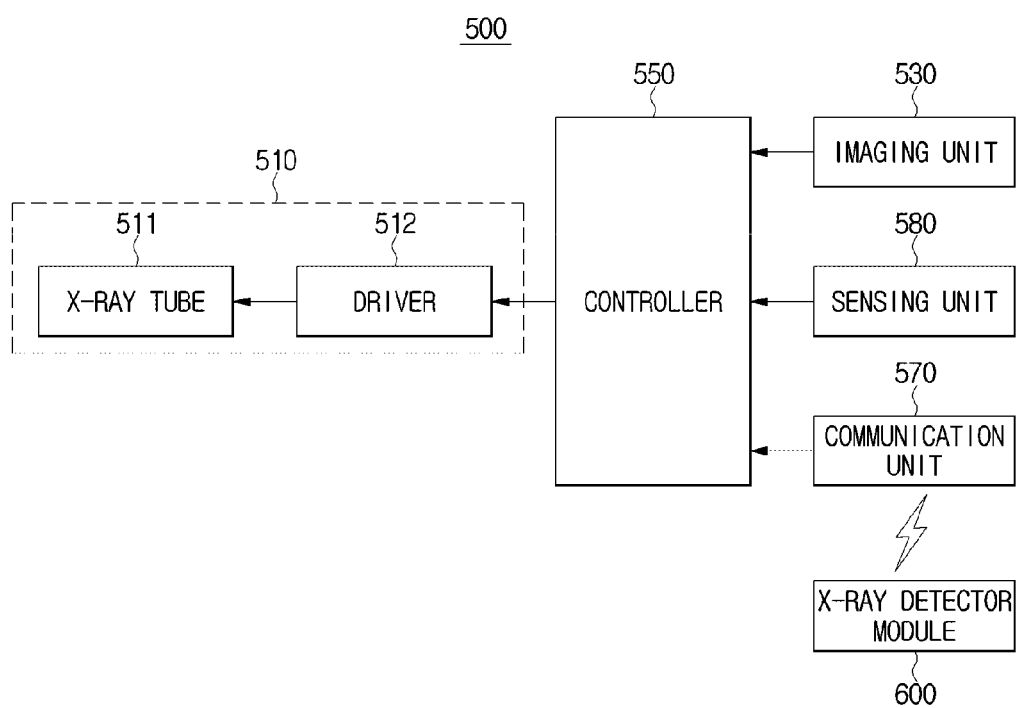
FIG. 25 is a control block diagram illustrating a communication unit and a sensing unit used for aligning an orientation of an X-ray tube.
Figure 26:
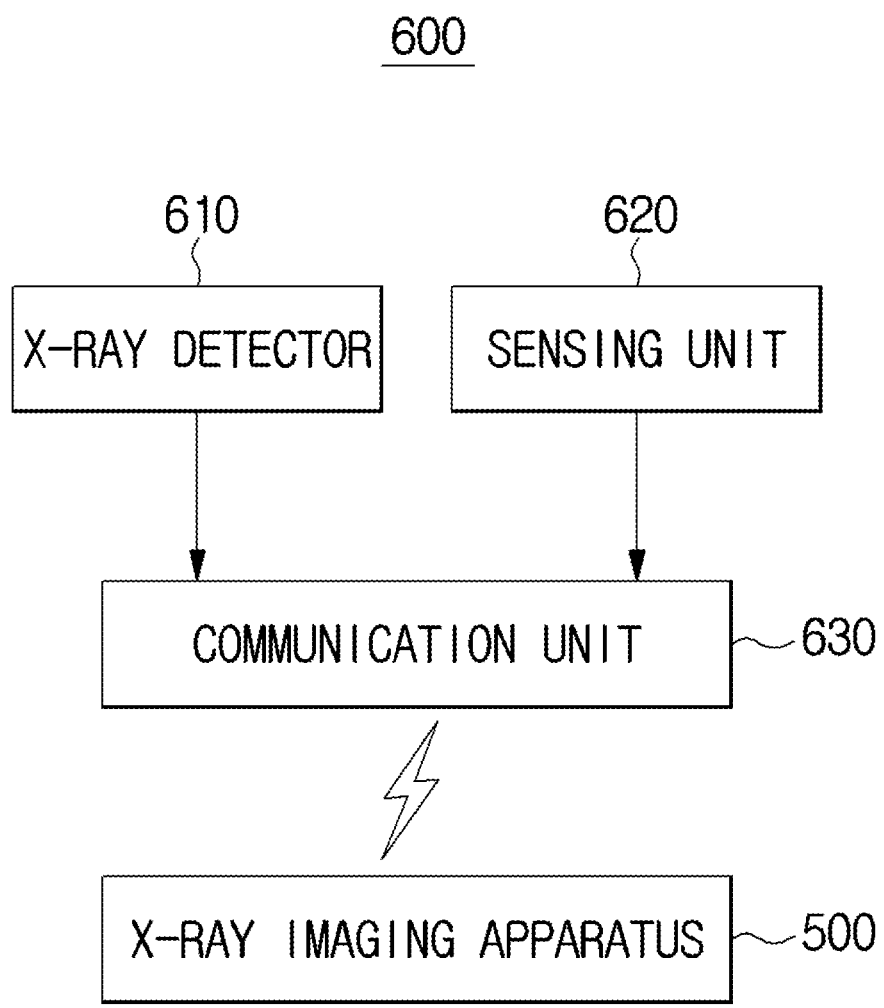
FIG. 26 is a control block diagram illustrating an X-ray detector module.

FIG. 25 is a control block diagram illustrating a communication unit and a sensing unit used for aligning an orientation of an X-ray tube. FIG. 26 is a control block diagram illustrating an X-ray detector module.

As illustrated in FIG. 25, the X-ray imaging apparatus 500 may further include a sensing unit 580 configured to detect the orientation of the X-ray tube 511 and a communication unit 570 configured to transmit and receive a signal to and from the X-ray detector module 600.

The sensing unit 580 may be directly mounted on the X-ray tube 511, mounted on the X-ray tube head 505 or the collimator 513, and detect an orientation of the X-ray tube head 505 or the collimator 513, and thus the orientation of the X-ray tube 511 may be indirectly detected. In the following embodiment, detecting the orientation of the X-ray tube 511 includes directly detecting and indirectly detecting the orientation of the X-ray tube 511.

The orientation of the X-ray tube 511 may be defined as an angular velocity of the X-ray tube 511 with respect to an x axis, a y axis and a z axis. The sensing unit 580 may include an angular velocity sensor configured to measure an angular velocity with respect to an x axis, a y axis and a z axis. The angular velocity sensor may be implemented by a gyro sensor.

Also, in order to measure the orientation more accurately, the sensing unit 580 may further include at least one of an accelerometer and a geomagnetic sensor. When the controller 550 calculates a control amount for aligning the orientation of the X-ray tube 511, a measured value of the angular velocity sensor and a measured value of the accelerometer or the geomagnetic sensor may be used together.

Meanwhile, an angular velocity with respect to each axis of the X-ray tube 511 may be controlled by the first subarm 503a, the second subarm 503b and the third subarm 503c. When power supplied to each of the subarms is known, the angular velocity with respect to each axis of the X-ray tube 511 may be calculated. Therefore, the sensing unit 580 may include an encoder configured to detect the number of revolutions of the motor, and the encoder may be mounted on the motor.

In some cases, the sensing unit 580 may include the angular velocity sensor, further include at least one of the accelerometer and the geomagnetic sensor, include the encoder, or may include a combination thereof. Also, a single-axis angle may be calculated using only the accelerometer. Therefore, as long as the angular velocity can be calculated, a configuration of the sensing unit 580 is not limited.

The communication unit 570 may include at least one component that enables communication with an external device via a communication network, and may include, for example, at least one of a short-range communication module, a wired communication module and a wireless communication module.

The short-range communication module refers to a module configured to perform short-range communication with a device positioned within a predetermined distance. Short-range communication technology that can be applied to the embodiment includes Wireless LAN, Wi-Fi, Bluetooth, Zigbee, Wi-Fi Direct (WED), Ultra wideband (UWB), Infrared Data Association (IrDA), Bluetooth Low Energy (BLE), Near Field Communication (NEC) and the like, but the present invention is not limited thereto.

The wired communication module refers to a module configured to perform communication using an electrical signal or an optical signal. Wired communication technology may include wired communication technology using a pair cable, a coaxial cable, an optical fiber cable or the like, but the present invention is not limited thereto. In addition to the above examples, wired communication technology apparent to those skilled in the art may be included.

The wireless communication module may include an antenna or a wireless communication chip configured to transmit and receive a radio signal to and from at least one of a base station, an external device, and a server via a mobile communication network, and for example, may be a wireless communication module configured to support IEEE 802.11x.

As will be described below, the communication unit 570 may receive information on the orientation of the X-ray detector module 600 from the X-ray detector module 600.

As illustrated in FIG. 26, the X-ray detector module 600 includes an X-ray detector 610 configured to detect X-rays and convert the X-rays into an electrical signal, a sensing unit 620 configured to detect an orientation of the X-ray detector module 600, and a communication unit 630 configured to transmit data detected by the sensing unit to the X-ray imaging apparatus 500.

Since description of the X-ray detector 610 is the same as the description of the X-ray detector 121 in the above-described embodiment, redundant description thereof will be omitted.

Similar to the sensing unit 580 configured to detect the orientation of the X-ray tube 511, the sensing unit 620 may include an angular velocity sensor configured to measure an angular velocity of the X-ray detector module 600 with respect to an x axis, a y axis and a z axis, and the angular velocity sensor may be implemented by a gyro sensor. Also, measuring, by the sensing unit 620, the orientation of the X-ray detector module 600 may refer to measuring an orientation of the X-ray detector 610.

Also, in order to measure the orientation more accurately, the sensing unit 620 may further include at least one of the accelerometer and the geomagnetic sensor.

The communication unit 630 may include at least one component that enables communication with an external device via a communication network, and may include, for example, at least one of a short-range communication module, a wired communication module and a wireless communication module. Description of each communication module is the same as the description of the communication unit 570.

The communication unit 630 transmits a measured value of the sensing unit 620 to the X-ray imaging apparatus 500, and the communication unit 570 of the X-ray imaging apparatus 500 receives the value. Also, the communication unit 630 may transmit the electrical signal obtained by converting X-rays detected by the X-ray detector 610, that is, projection data, to the X-ray imaging apparatus 500.

The controller 550 compares the orientation of the X-ray detector module 600 received from the communication unit 630 and a current orientation of the X-ray tube 511 measured by the sensing unit 580, and calculates a control amount for aligning the orientation of the X-ray tube 511. For example, the orientation of the X-ray tube 511 in which X-rays vertically radiated from the X-ray tube 511 can be vertically incident on an X-ray detector 521 may be defined as an orientation corresponding to the X-ray detector 610.

Figure 27:
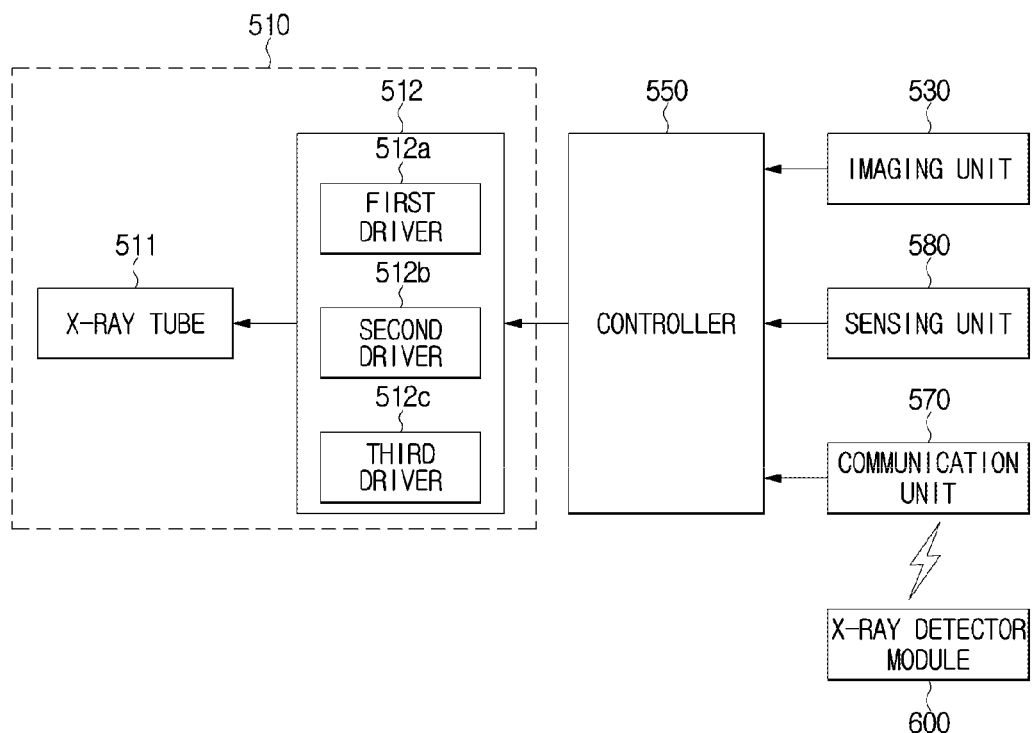
FIG. 27 is a control block diagram illustrating a configuration of a driver.
Figure 28:
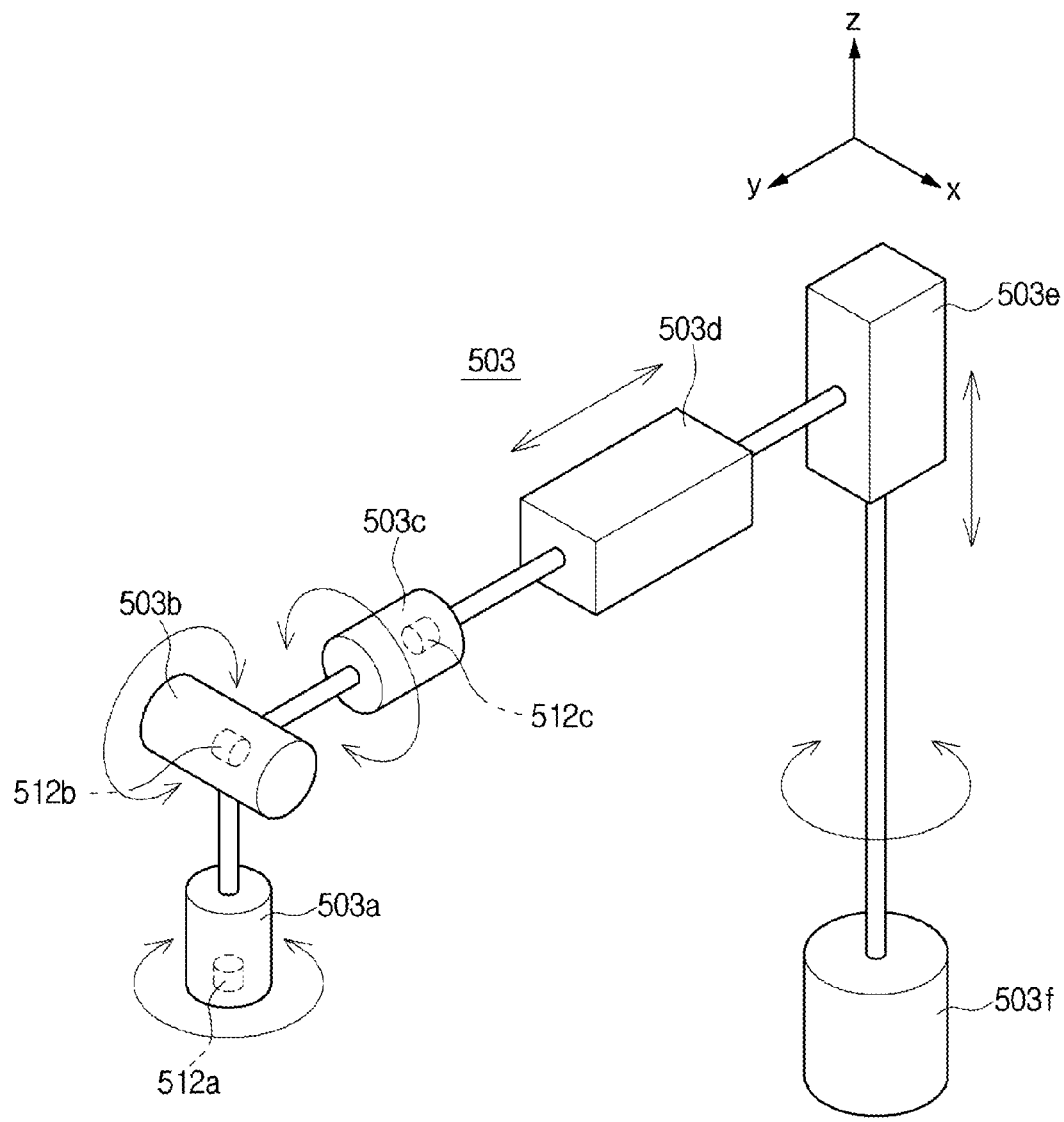
FIG. 28 is a diagram illustrating a position of a motor.

FIG. 27 is a control block diagram illustrating a configuration of a driver. FIG. 28 is a diagram illustrating a position of a motor.

In order to control the orientation of the X-ray tube 511, the first subarm 503a, the second subarm 503b and the third subarm 503c may be moved. In order to automatically move these arms, the motor may be provided in each of the arms.

As illustrated in FIGS. 27 and 28, the driver 512 may include a first driver 512a configured to provide power for rotational movement of the first subarm 503a, a second driver 512b configured to provide power for rotational movement of the second subarm 503b and a third driver 512c configured to provide power for rotational movement of the third subarm 503. Each of the drivers may include a motor, an inverter and a drive circuit, but this is only an example, and a configuration other than the motor may be changed.

Meanwhile, a specific position of the motor or the driver including the motor may be changed according to a method of delivering power to the subarm. In the embodiment of the X-ray imaging apparatus 500, a specific position of the motor or the driver is not limited.

The controller 550 may calculate a movement amount of the first subarm 503a, the second subarm 503b and the third subarm 503c based on the orientation of the X-ray detector module 600 and a current orientation of the X-ray tube 511, that is, a control amount necessary for moving these arms, generate a control signal corresponding to the calculated control amount, and deliver the signal to the first driver 512a, the second driver 512b and the third driver 512c. The drive circuit generates a driving signal corresponding to the control signal and outputs the signal to the inverter. The inverter may supply a drive voltage and a drive current to the motor according to the driving signal.

The first driver 512a, the second driver 512b and the third driver 512c generate power according to the calculated control amount, and move the first subarm 503a, the second subarm 503b and the third subarm 503c, respectively. According to movement of the first subarm 503a, the second subarm 503b and the third subarm 503c, the orientation of the X-ray tube 511 may be aligned with the X-ray detector module 600.

Meanwhile, the position alignment of the X-ray tube 511 may be manually performed by the user. According to the position alignment of the X-ray tube 511, a center of the X-ray tube 511 may be aligned with the imaged part.

Figure 29:
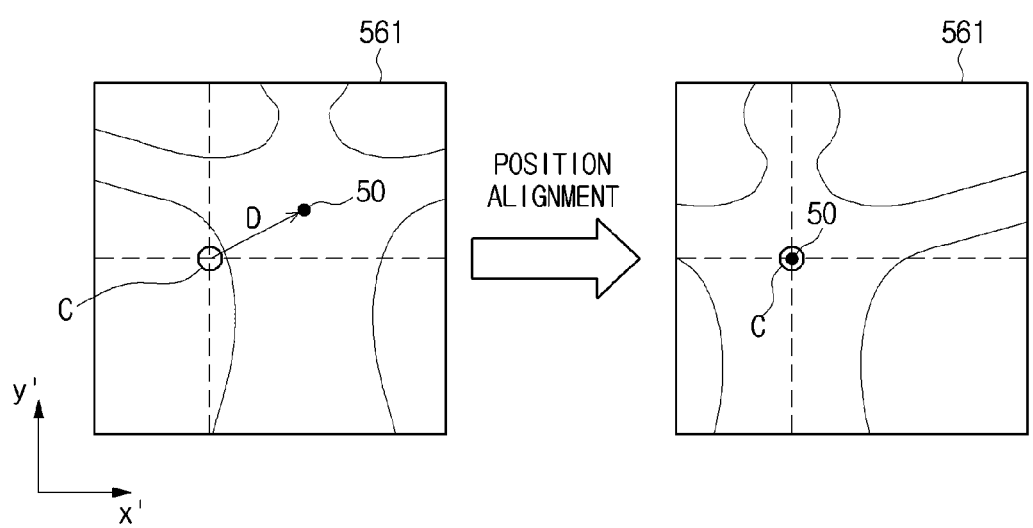
FIG. 29 is a diagram illustrating an exemplary image of an imaging unit displayed on a display unit.

FIG. 29 is a diagram illustrating an exemplary image of an imaging unit displayed on a display unit.

When the user manually aligns the position of the X-ray tube 511, as illustrated in FIG. 29, the user may refer to an image displayed on the display unit 561. The image displayed on the display unit 561 may be the subject image imaged by the imaging unit 530.

The display unit 561 may display the center C of the X-ray tube 511 on the subject image. When the displayed subject image is the same as the example of FIG. 29, the user may move the X-ray tube 511 according to a vector D in order to align the center C of the X-ray tube 511 with the marker. The vector D may be defined by an x' axis and a y' axis set based on the subject image.

The imaging unit 530 may image the subject image in real time, and the subject image imaged in real time may be displayed on the display unit 561. Therefore, the user may manipulate the fourth subarm 503d, the fifth subarm 503e and the sixth subarm 503f and align the position of the X-ray tube 511 while checking the display unit 561. In this case, the display unit 561 may be mounted on the X-ray tube head 505 such that the user may easily check the subject image while manipulating the tube arm 503.

Meanwhile, while the position alignment of the X-ray tube 511 is performed, the orientation alignment of the X-ray tube 511 may also be performed in real time. For this purpose, the sensing unit 580 may detect the orientation of the X-ray tube 511 in real time and deliver the result to the controller 550. The controller 550 calculates a control amount again based on the detected orientation of the X-ray tube 511, and transmits a control signal to the first driver 512a, the second driver 512b and the third driver 512c. The first driver 512a, the second driver 512b and the third driver 512c may generate power according to the calculated control amount, and move the first subarm 503a, the second subarm 503b and the third subarm 503c.

Also, while the position of the X-ray tube 511 is aligned, when the orientation of the X-ray detector module 600 is changed, the sensing unit 620 may detect the orientation of the X-ray detector module 600 and transmit the result to the X-ray imaging apparatus 500 through the communication unit 630. Therefore, even when the orientation of the X-ray tube 511 is changed in the process of aligning the position of the X-ray tube 511, the orientation may be re-aligned in real time.

As described above, when only the orientation alignment is automatically performed and the position alignment is manually performed, the number of motors and the number of related components accompanying therewith can be reduced, and costs can be reduced.

Also, when the orientation alignment is performed, at least one of the first driver, the second driver and the third driver may be manually driven. As the ratio of drives that are manually driven increases, a design can be simplified and costs can be reduced. However, for convenience of description, all of the first driver, the second driver and the third driver will be described in the following embodiment as being automatically driven.

Meanwhile, when the orientation alignment of the X-ray tube 511 and the position alignment are entirely or partially automatically performed, it is possible to reduce the user's workload and improve the user's convenience. That is, the position alignment can be automatically or semi-automatically performed. Hereinafter, details will be described with reference to the drawings.

Figure 30:
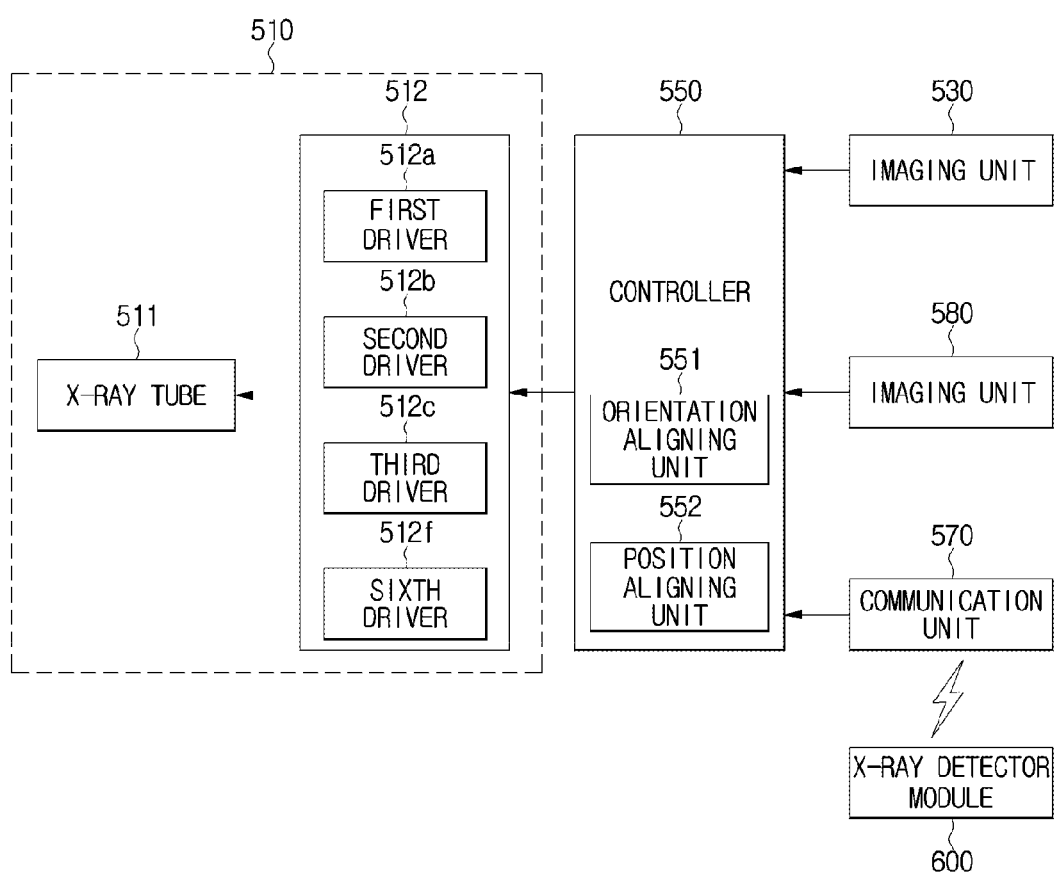
FIG. 30 is a control block diagram illustrating another exemplary X-ray imaging apparatus according to still another embodiment of the present invention.
Figure 31:
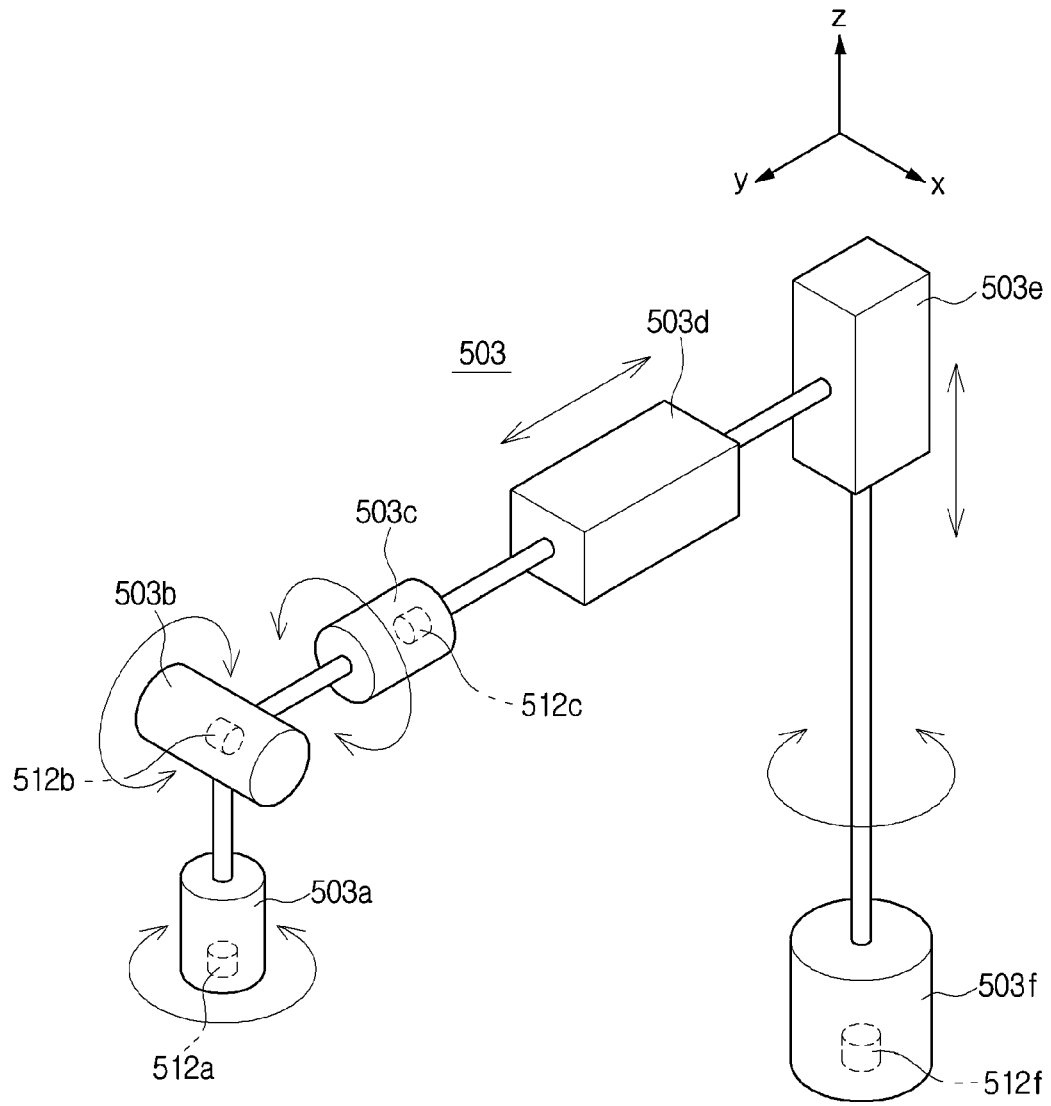
FIG. 31 is a diagram illustrating a position of a motor of the X-ray imaging apparatus according to the example of FIG. 30.

FIG. 30 is a control block diagram illustrating another exemplary X-ray imaging apparatus according to still another embodiment of the present invention. FIG. 31 is a diagram illustrating a position of a motor of the X-ray imaging apparatus according to the example of FIG. 30. According to this example, one of the fourth subarm 503d, the fifth subarm 503e and the sixth subarm 503f for the position alignment of the X-ray tube 511 can be automatically controlled. A case in which the sixth subarm 503f is automatically controlled will be exemplified.

As illustrated in FIGS. 30 and 31, the driver 512 may further include a sixth driver 512f in addition to the first driver 512a, the second driver 512b and the third driver 512c. The sixth driver 512f may be provided in the sixth subarm 503f in order to provide power for rotational movement of the sixth subarm 503f.

The controller 550 may include an orientation aligning unit 551 configured to align the orientation of the X-ray tube 511 and a position aligning unit 552 configured to align a position. As exemplified above, the orientation alignment of the X-ray tube 511 may be automatically performed by the orientation aligning unit 551 based on measurement of the orientation of the X-ray tube 511 and measurement of the orientation of the X-ray detector module 600. When the orientation alignment is completed, the position alignment of the X-ray tube 511 may be performed by the position aligning unit 552.

The controller 550 may include a memory in which a program configured to perform the above operations and operations to be described and data necessary for executing the program are stored and a processor configured to execute the stored program. The orientation aligning unit 551 and the position aligning unit 552 may use a separate memory or processor or share the memory or the processor.

The controller 550 may use the subject image imaged by the imaging unit 530 for position alignment of the X-ray tube 511. As described above, the marker 50 such as a spotlight is displayed on the imaged part of the subject 30, and the marker 50 is identifiable in the subject image. The controller 550 may apply a recognition algorithm, recognize the marker 50 from the subject image, and calculate a position of the recognized marker. The position of the marker can be calculated as coordinates in a 2D space.

The controller 550 may recognize a relative position between the X-ray tube 511 and the imaging unit 530 in advance. The position of the marker to be calculated may be a relative position with respect to the X-ray tube 511. The controller 550 may calculate a control amount for aligning the position of the X-ray tube 511 with the position of the marker 50. The position of the X-ray tube 511 corresponding to the marker 50 may be a position in which a center of the X-ray tube 511 is aligned with the marker 50.

As described above, the sixth subarm 503$f$ is involved in the position alignment of the X-ray tube 511 along with the fourth subarm 503$d$ and the fifth subarm 503$e$. Therefore, the control amount calculated by the controller 550 may relate to the sixth driver 512$f$ configured to provide power to the sixth subarm 503$f$, and a control signal including the calculated control amount may be transmitted to the sixth driver 512$f$.

Meanwhile, when the tube arm 503 is manipulated to align the orientation or the position of the X-ray tube 511, the X-ray imaging apparatus 500 may apply inverse kinematics and PD control or PID control. When inverse kinematics is applied to calculate power necessary for each of the arms constituting the tube arm 503 and necessary power is supplied using the motor, the PD control or the PID control may be applied.

The remaining fourth subarm 503$d$ and fifth subarm 503$e$ involved in the position alignment of the X-ray tube 511 may be manually controlled by the user. The subject image imaged by the imaging unit 530 may be displayed on the display unit 561, and the user may move the fourth subarm 503$d$ and the fifth subarm 503$e$ while checking the image displayed on the display unit 561.

As described above, while the position alignment is performed, the orientation alignment may be performed in real time. Also, manual alignment and automatic alignment may be simultaneously performed, or either thereof may be performed first and then the remaining alignment may be performed. Also, when automatic alignment is performed first and then manual alignment is performed, the position of the arm that has been automatically aligned may be changed while manual alignment is performed. Therefore, automatic alignment may be continuously performed in real time. This description may be applied to other examples to be described below.

Figure 32:
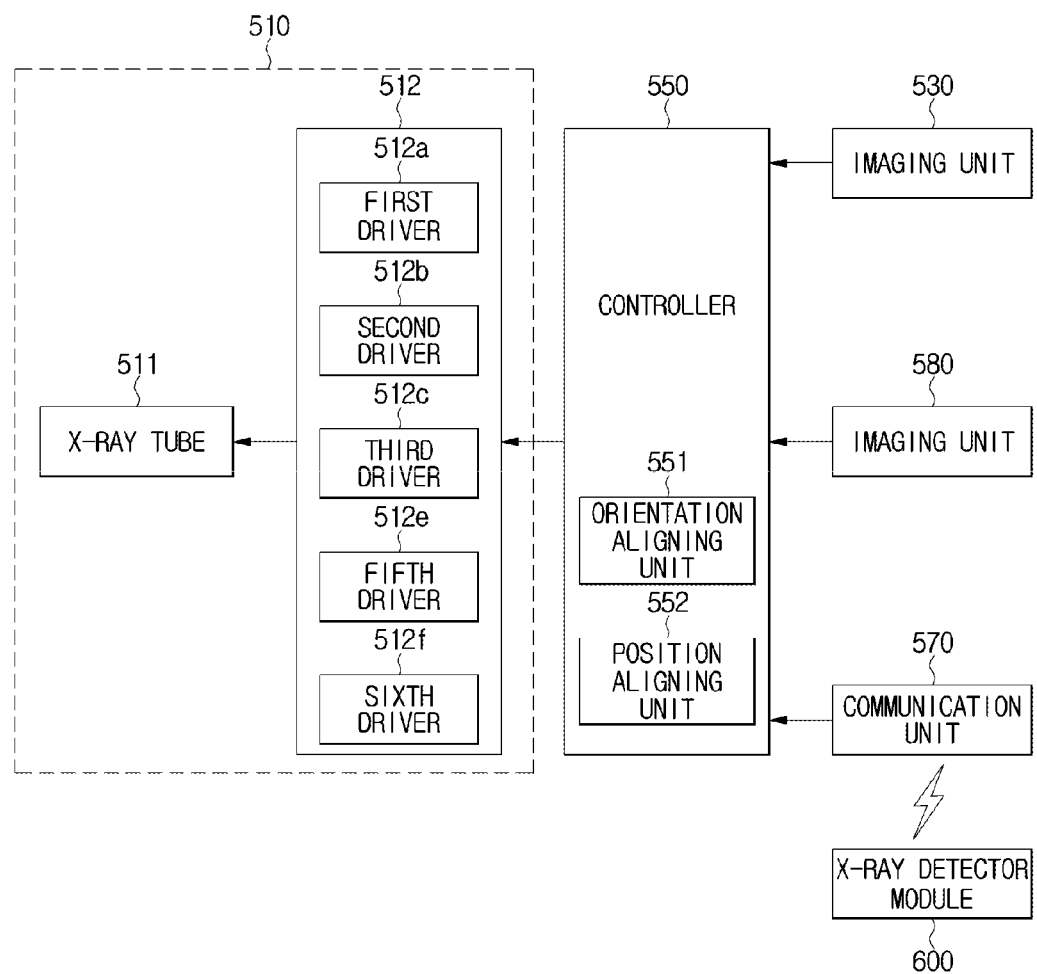
FIG. 32 is a control block diagram illustrating still another exemplary X-ray imaging apparatus according to another embodiment of the present invention.
Figure 33:
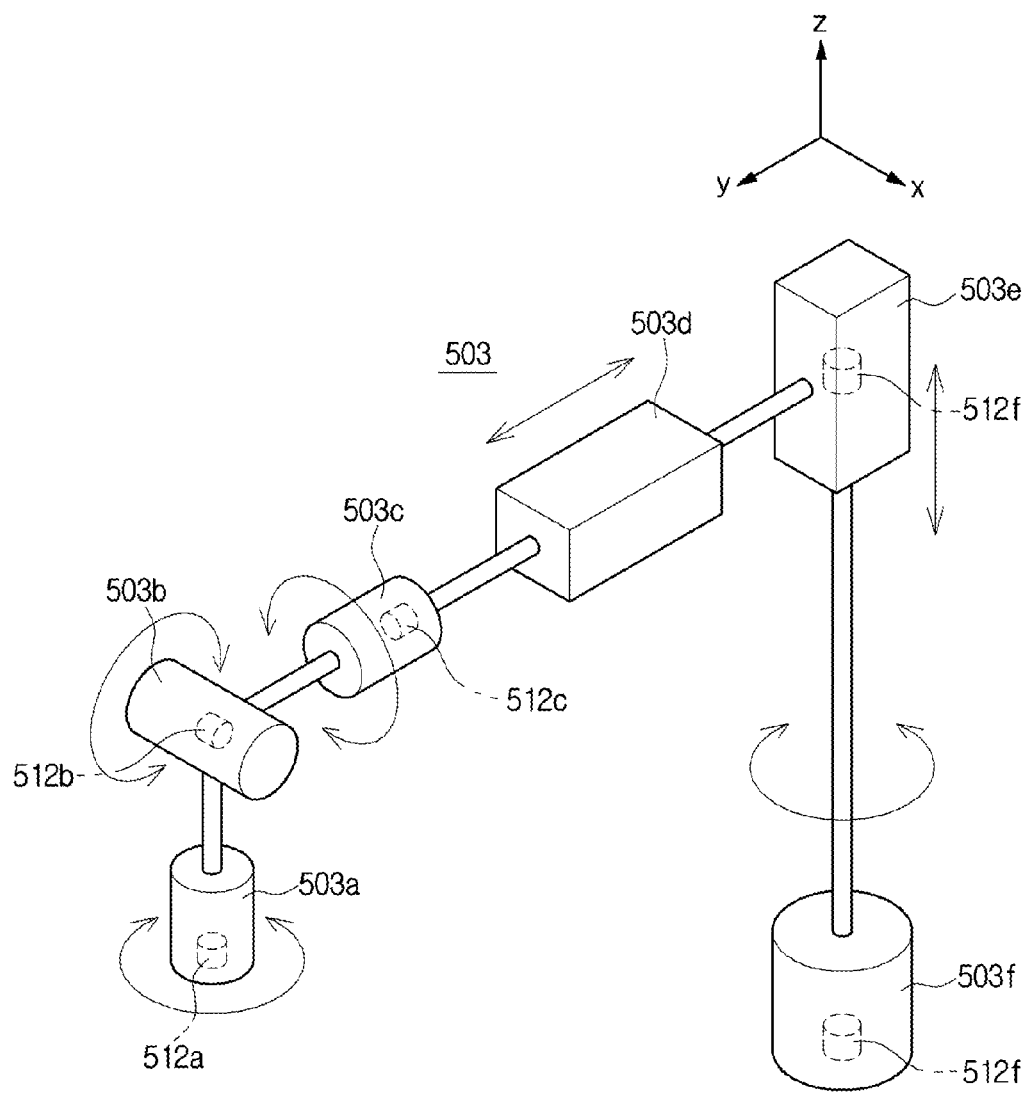
FIG. 33 is a diagram illustrating a position of a motor of the X-ray imaging apparatus according to the example of FIG. 32.

FIG. 32 is a control block diagram illustrating still another exemplary X-ray imaging apparatus according to another embodiment of the present invention. FIG. 33 is a diagram illustrating a position of a motor of the X-ray imaging apparatus according to the example of FIG. 32.

As illustrated in FIGS. 32 and 33, according to still another example of the X-ray imaging apparatus 500, the driver 512 may further include a fifth driver 512$e$ and the sixth driver 512$f$ in addition to the first driver 512$a$, the second driver 512$b$ and the third driver 512$c$. The fifth driver 512$e$ may be provided in the fifth subarm 503$e$ in order to provide power for linear movement of the fifth subarm 503$e$. The sixth driver 512$f$ may be provided in the sixth subarm 503$f$ in order to provide power for rotational movement of the sixth subarm 503$f$.

As exemplified above, the orientation of the X-ray tube 511 may be automatically aligned by the controller 550 based on measurement of the orientation of the X-ray tube 511 and measurement of the orientation of the X-ray detector module 600. When orientation alignment is completed, the position of the X-ray tube 511 may be aligned.

In order to align the position of the X-ray tube 511, the controller 550 may use the subject image imaged by the imaging unit 530. As described above, the marker 50 such as a spotlight is displayed on the imaged part of the subject 30, and the controller 550 may apply a recognition algorithm and recognize the marker 50 from the subject image. The controller 550 may calculate a position of the recognized marker and calculate a control amount for aligning the position of the X-ray tube 511 with the position of the marker 50.

The control amount calculated by the controller 550 may relate to the fifth driver 512$e$ configured to provide power to the fifth subarm 503$e$ and the sixth driver 512$f$ configured to provide power to the sixth subarm 503$f$. A control signal including the calculated control amount may be transmitted to each of the fifth driver 512$e$ and the sixth driver 512$f$.

The remaining fourth subarm 503$d$ involved in the position alignment of the X-ray tube 511 may be manually controlled by the user. The subject image imaged by the imaging unit 530 may be displayed on the display unit 561, and the user may move the fourth subarm 503$d$ while checking the image displayed on the display unit 561.

Figure 34:
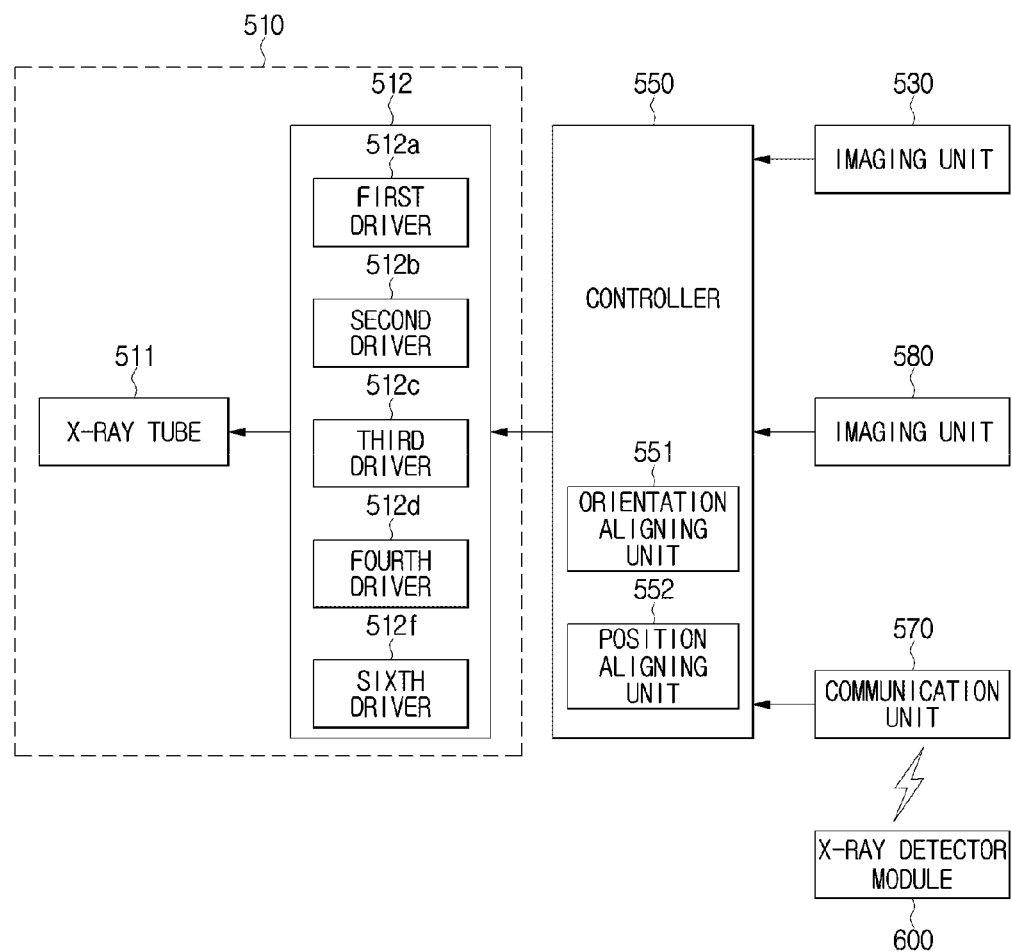
FIG. 34 is a control block diagram illustrating still another exemplary X-ray imaging apparatus according to another embodiment of the present invention.
Figure 35:
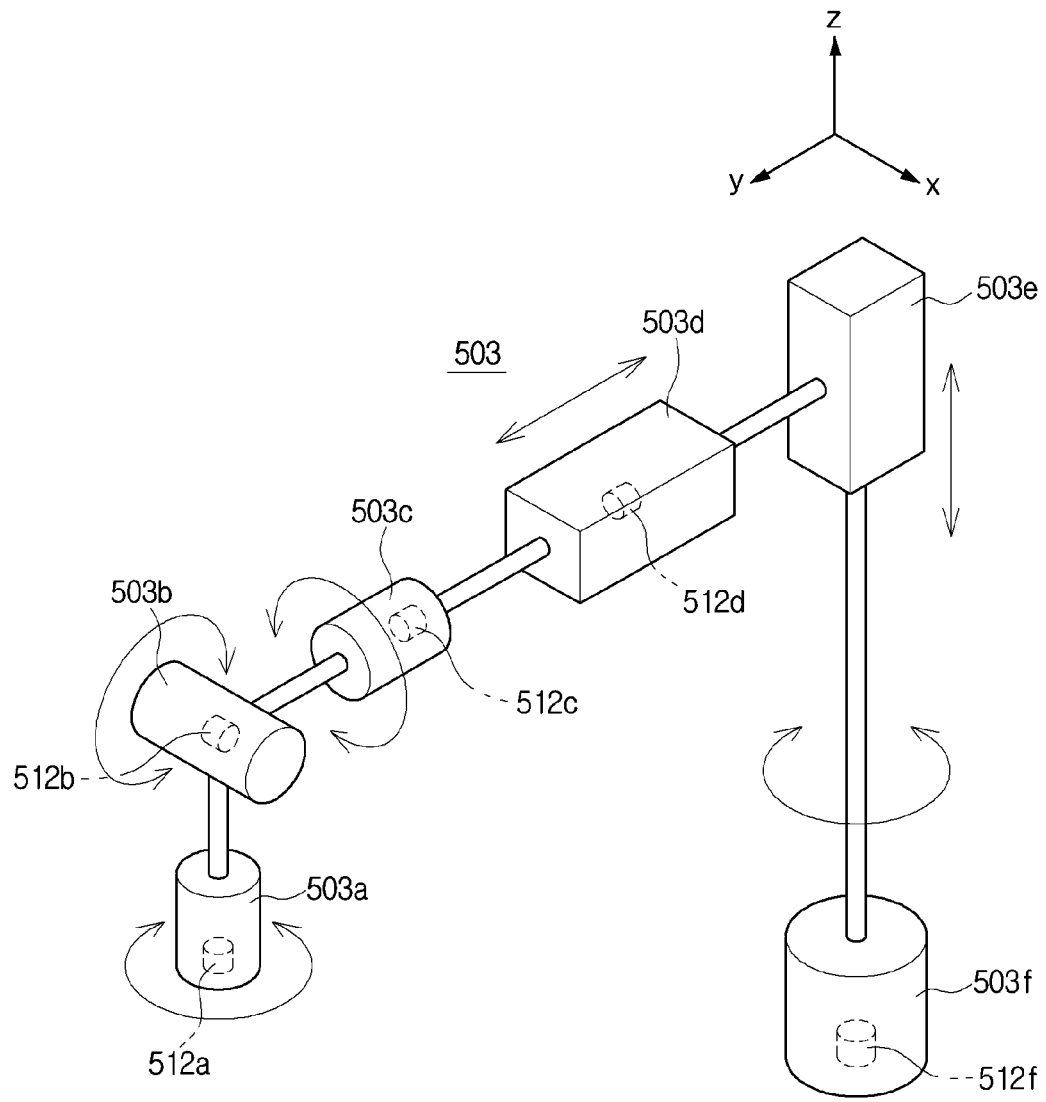
FIG. 35 is a diagram illustrating a position of a motor of the X-ray imaging apparatus according to the example of FIG. 34.

FIG. 34 is a control block diagram illustrating still another exemplary X-ray imaging apparatus according to another embodiment of the present invention. FIG. 35 is a diagram illustrating a position of a motor of the X-ray imaging apparatus according to the example of FIG. 34.

As illustrated in FIGS. 34 and 35, according to still another example of the X-ray imaging apparatus 500, the driver 512 may further include a fourth driver 512$d$ and the sixth driver 512$f$ in addition to the first driver 512$a$, the second driver 512$b$ and the third driver 512$c$. The fourth driver 512$d$ may be provided in the fourth subarm 503$d$ in order to provide power for linear movement of the fourth subarm 503$d$. The sixth driver 512$f$ may be provided in the sixth subarm 503$f$ in order to provide power for rotational movement of the sixth subarm 503$f$.

As exemplified above, the orientation of the X-ray tube 511 may be automatically aligned by the controller 550 based on measurement of the orientation of the X-ray tube 511 and measurement of the orientation of the X-ray detector module 600. When orientation alignment is completed, the position of the X-ray tube 511 may be aligned.

In order to align the position of the X-ray tube 511, the controller 550 may use the subject image imaged by the imaging unit 530. As described above, the marker 50 such as a spotlight is displayed on the imaged part of the subject 30, and the controller 550 may apply a recognition algorithm and recognize the marker 50 from the subject image. The controller 550 may calculate a position of the recognized marker and calculate a control amount for aligning the position of the X-ray tube 511 with the position of the marker 50.

The control amount calculated by the controller 550 may relate to the fourth driver 512d and the sixth driver 512f. A control signal including the calculated control amount may be transmitted to each of the fourth driver 512d and the sixth driver 512f.

The remaining fifth subarm 503e involved in the position alignment of the X-ray tube 511 may be manually controlled by the user. The subject image imaged by the imaging unit 530 may be displayed on the display unit 561, and the user may move the fifth subarm 503e while checking the image displayed on the display unit 561.

Figure 36:
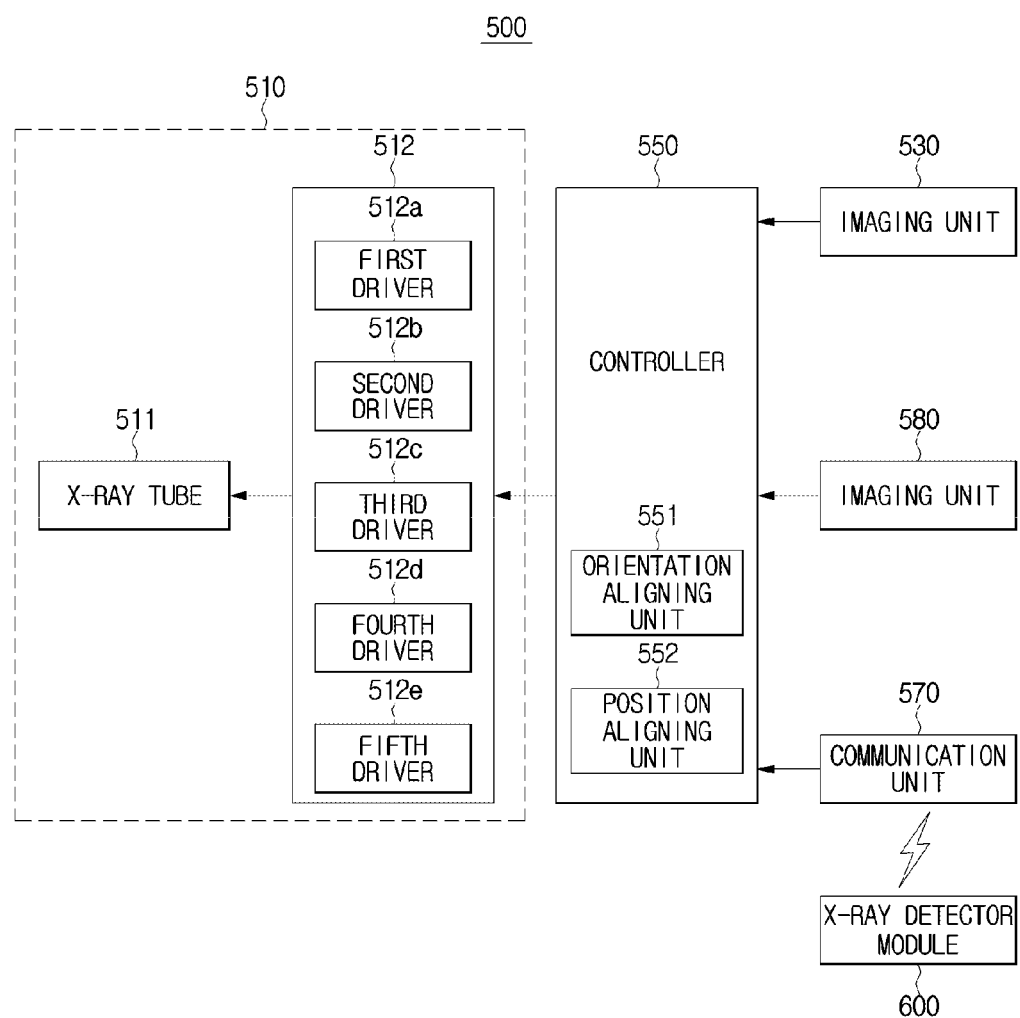
FIG. 36 is a control block diagram illustrating still another exemplary X-ray imaging apparatus according to another embodiment of the present invention.
Figure 37:
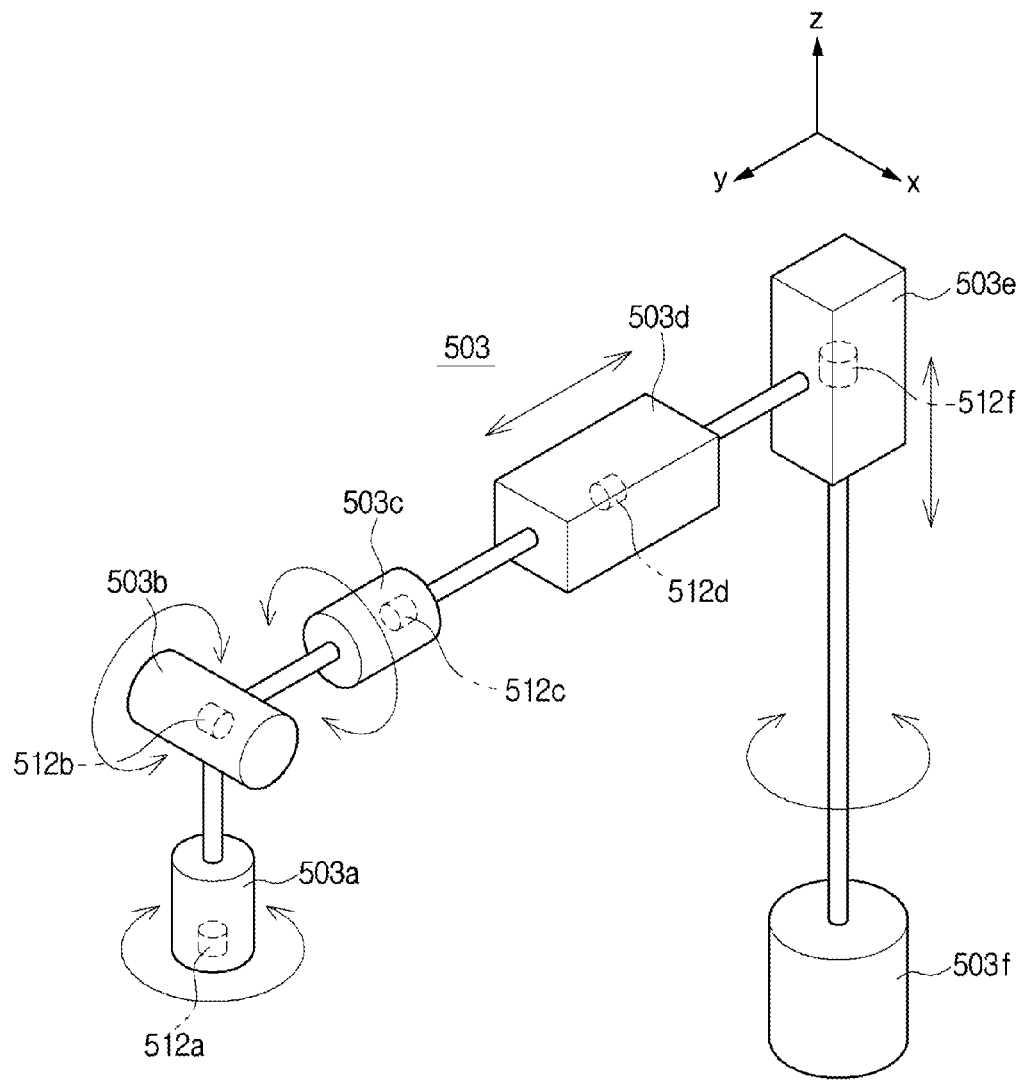
FIG. 37 is a diagram illustrating a position of a motor of the X-ray imaging apparatus according to the example of FIG. 36.

FIG. 36 is a control block diagram illustrating still another exemplary X-ray imaging apparatus according to another embodiment of the present invention. FIG. 37 is a diagram illustrating a position of a motor of the X-ray imaging apparatus according to the example of FIG. 36.

As illustrated in FIGS. 36 and 37, according to still another example of the X-ray imaging apparatus 500, the driver 512 may further include the fourth driver 512d and the fifth driver 512e in addition to the first driver 512a, the second driver 512b and the third driver 512c.

As exemplified above, the orientation of the X-ray tube 511 may be automatically aligned by the controller 550 based on measurement of the orientation of the X-ray tube 511 and measurement of the orientation of the X-ray detector module 600. When orientation alignment is completed, the position of the X-ray tube 511 may be aligned.

In order to align the position of the X-ray tube 511, the controller 550 may use the subject image imaged by the imaging unit 530. As described above, the marker 50 such as a spotlight is displayed on the imaged part of the subject 30, and the controller 550 may apply a recognition algorithm and recognize the marker 50 from the subject image. The controller 550 may calculate a position of the recognized marker and calculate a control amount for aligning the position of the X-ray tube 511 with the position of the marker 50.

The control amount calculated by the controller 550 may relate to the fourth driver 512d and the fifth driver 512e. A control signal including the calculated control amount may be transmitted to each of the fourth driver 512d and the fifth driver 512e.

The remaining sixth subarm 503f involved in the position alignment of the X-ray tube 511 may be manually controlled by the user. The subject image imaged by the imaging unit 530 may be displayed on the display unit 561, and the user may move the sixth subarm 503f while checking the image displayed on the display unit 561.

Figure 38:
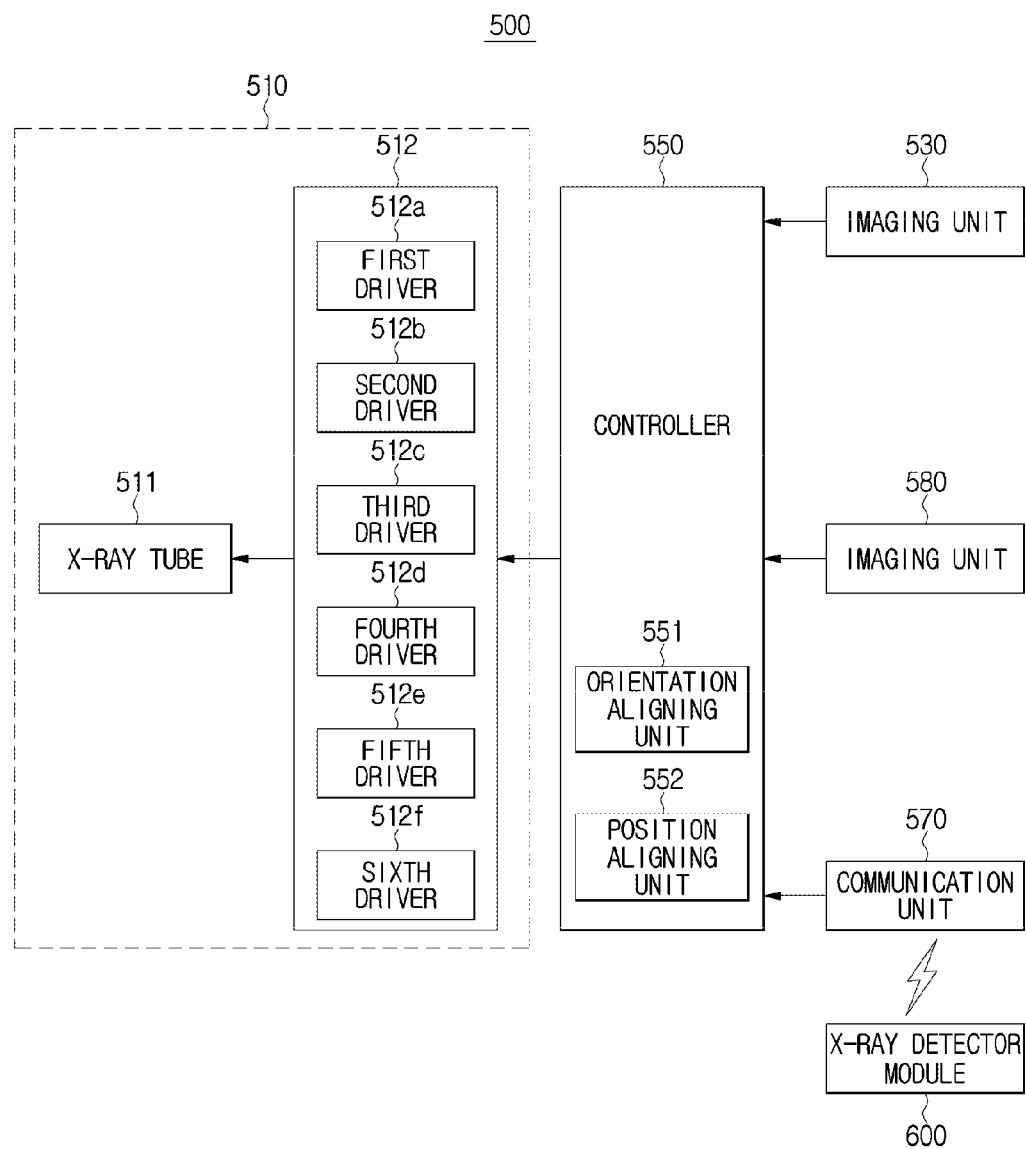
FIG. 38 is a control block diagram illustrating still another exemplary X-ray imaging apparatus according to another embodiment of the present invention.
Figure 39:
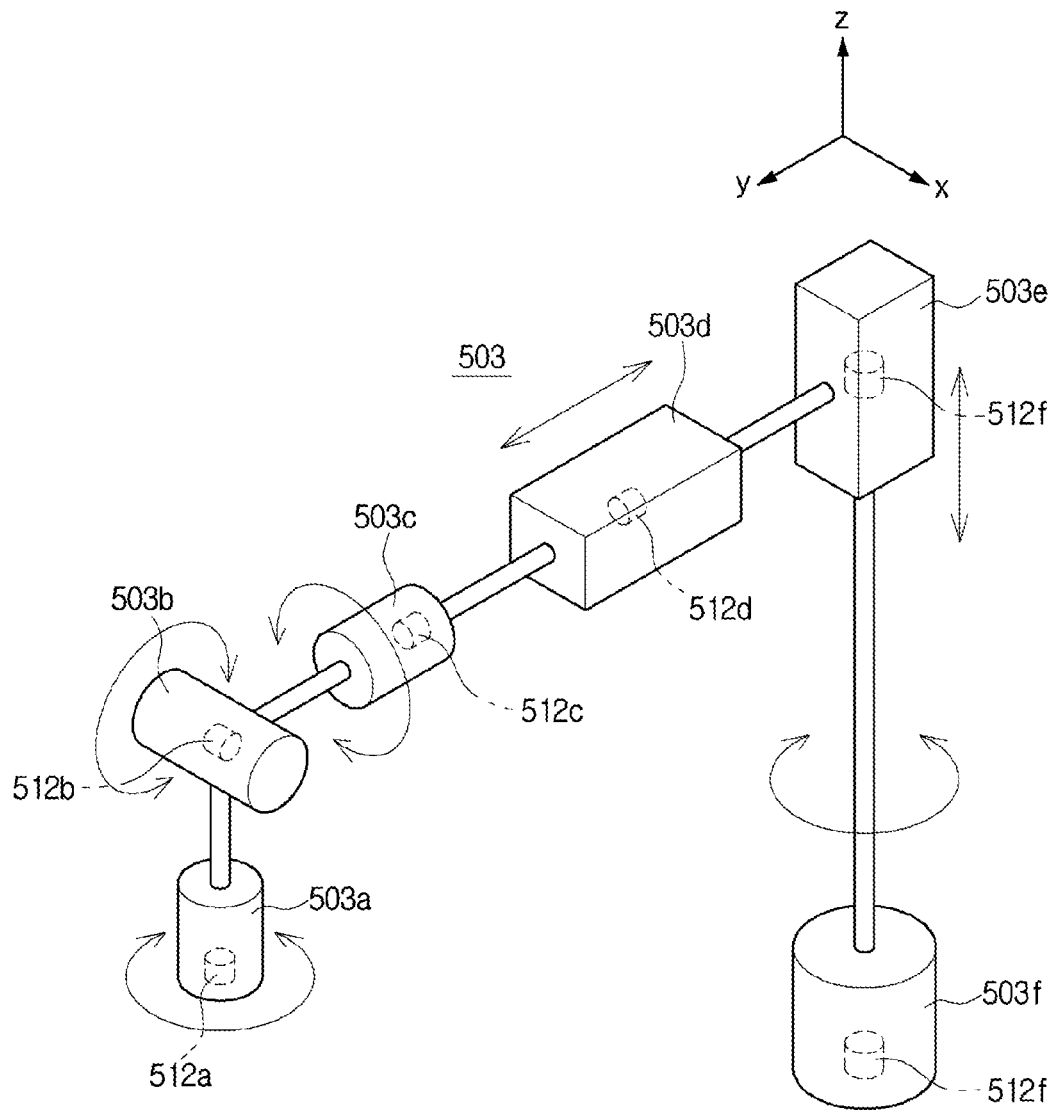
FIG. 39 is a diagram illustrating a position of a motor of the X-ray imaging apparatus according to the example of FIG. 38.

FIG. 38 is a control block diagram illustrating still another exemplary X-ray imaging apparatus according to another embodiment of the present invention. FIG. 39 is a diagram illustrating a position of a motor of the X-ray imaging apparatus according to the example of FIG. 38.

As illustrated in FIGS. 38 and 39, according to still another example of the X-ray imaging apparatus 500, the driver 512 may further include the fourth driver 512d, the fifth driver 512e and the sixth driver 512f in addition to the first driver 512a, the second driver 512b and the third driver 512c. That is, the position alignment of the X-ray tube 511 may also be completely automatically performed.

As exemplified above, the orientation of the X-ray tube 511 may be automatically aligned by the controller 550 based on measurement of the orientation of the X-ray tube 511 and measurement of the orientation of the X-ray detector module 600. When orientation alignment is completed, the position of the X-ray tube 511 may be aligned.

In order to align the position of the X-ray tube 511, the controller 550 may use the subject image imaged by the imaging unit 530. As described above, the marker 50 such as a spotlight is displayed on the imaged part of the subject 30, and the controller 550 may apply a recognition algorithm and recognize the marker 50 from the subject image. The controller 550 may calculate a position of the recognized marker and calculate a control amount for aligning the position of the X-ray tube 511 with the position of the marker 50.

The control amount calculated by the controller 550 may relate to the fourth driver 512d, the fifth driver 512e and the sixth driver 512f. A control signal including the calculated control amount may be transmitted to each of the fourth driver 512d, the fifth driver 512e and the sixth driver 512f.

As described above, when the orientation alignment and the position alignment are automatically performed, it is possible to increase accuracy of the position alignment and decrease the user's workload.

Hereinafter, a method for controlling an X-ray imaging apparatus according to an exemplary embodiment will be described.

Figure 40:
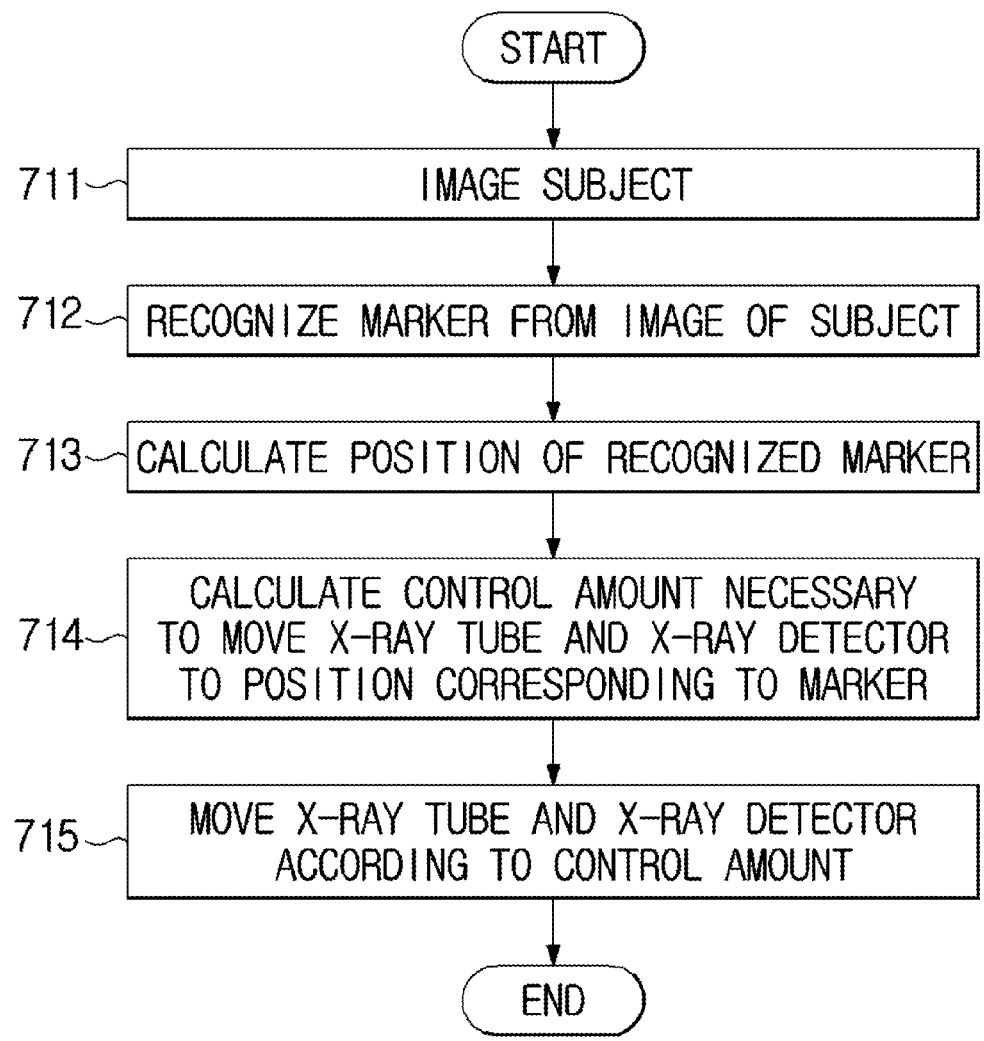
FIG. 40 is a flowchart which illustrates a method for controlling an X-ray imaging apparatus which corresponds to the exemplary embodiment illustrated in FIG. 2.

FIG. 40 is a flowchart which illustrates a method for controlling an X-ray imaging apparatus which corresponds to the exemplary embodiment illustrated in FIG. 2.

Referring to FIG. 40, in operation 711, the subject is imaged by using a camera before commencement of X-ray imaging. The subject is imaged in a state in which preparation for X-ray imaging is completed; in particular, in a state in which the subject is located between the X-ray tube and the X-ray detector, the user locates a marker on the part of the subject to be subjected to X-ray imaging. If the camera is a wide-angle camera which covers an entirety of the subject or the patient table, the subject may be imaged in a single stage and, if the camera is a normal camera which has a normal lens mounted therein, imaging of the subject may be performed in multiple stages.

In operation 712, the marker is recognized from the image of the subject. The marker may be recognized by using at least one of various object recognition algorithms. Information relating to a particular feature of the marker may be pre-stored, and the marker having the particular feature may be recognized from the image of the subject.

In operation 713, the position of the recognized marker is calculated. In one exemplary embodiment, the position of the marker may be calculated as coordinates (m, n) in a two-dimensional coordinate system. Calculation of the position of the marker may be completed before the X-ray tube and the X-ray detector are moved, or the position of the marker may be calculated during a predetermined period or in real time while the X-ray tube and the X-ray detector are being moved to target positions, thereby updating the result.

In operation 714, a control amount for causing each of the X-ray tube and the X-ray detector to be moved to respective positions which correspond to the marker is calculated. For this calculation, information relating to the relative position between the X-ray tube and the subject image and information relating to the relative position between the X-ray detector and the subject image may be pre-stored. In particular, the actual positions of the X-ray tube and the X-ray detector as expressed with respect to the coordinate system of the subject image may be pre-stored. The target positions of the X-ray tube and the X-ray detector may be acquired based on the stored relative position information, and the control amount for causing the X-ray tube and the X-ray detector to be moved to the respective target positions is calculated. The target positions of the X-ray tube and the X-ray detector, more particularly, the positions corresponding to the marker, may be positions where the center of the X-ray radiation region of the X-ray tube and the center of the detection region of the X-ray detector match the marker or the center of the marker in a two-dimensional space.

In operation 715, the X-ray tube and the X-ray detector are moved based on the calculated control amount, and X-ray imaging is performed.

Figure 41:
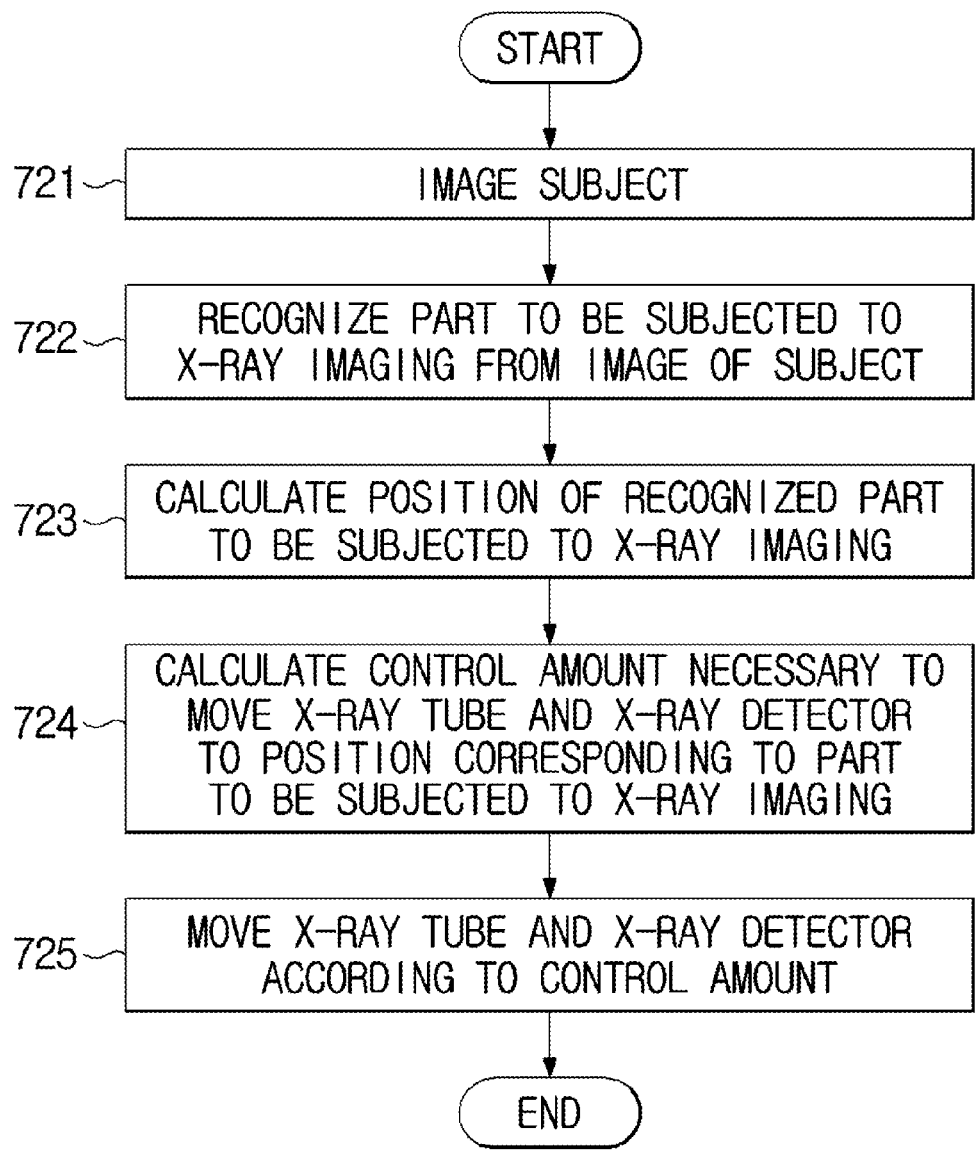
FIG. 41 is a flowchart which illustrates a method for controlling an X-ray imaging apparatus which corresponds to the exemplary embodiment illustrated in FIG. 11.

FIG. 41 is a flowchart which illustrates a method for controlling an X-ray imaging apparatus which corresponds to the exemplary embodiment illustrated in FIG. 11.

Referring to FIG. 41, in operation 721, a subject is imaged by using a camera before X-ray imaging. The subject is imaged in a state in which preparation for X-ray imaging is completed; in particular, in a state in which the subject is located between the X-ray tube and the X-ray detector. The subject may be imaged in a single stage if the camera is a wide-angle camera which is capable of covering an entirety of the subject or the patient table, and may be imaged in multiple stages if the camera is a normal camera which has a normal lens mounted therein.

In operation 722, a part to be subjected to X-ray imaging is recognized from the image of the subject. The part to be subjected to X-ray imaging may be recognized by using at least one of various object recognition algorithms, and information relating to at least one of particular features of the part to be subjected to X-ray imaging may be pre-stored, and the part to be subjected to X-ray imaging which has the particular features may be recognized from the image of the subject.

In operation 723, the position of the recognized part to be subjected to X-ray imaging is calculated. In an exemplary embodiment, the position of the part to be subjected to X-ray imaging may be calculated as coordinates (m, n) of a two-dimensional coordinate system. The position of the part to be subjected to X-ray imaging may be the position of the center of the part to be subjected to X-ray imaging. However, the position of the center of the part to be subjected to X-ray imaging is not necessarily calculated, and the position of an arbitrary portion of the part to be subjected to X-ray imaging may be calculated, based on the size of the part to be subjected to X-ray imaging.

In operation 724, a control amount for causing each of the X-ray tube and the X-ray detector to be moved to the respective positions which correspond to the part to be subjected to X-ray imaging is calculated. Information relating to the relative position between the X-ray tube and the subject image and information relating to the relative position between the X-ray detector and the subject image may be pre-stored. In particular, the actual positions of the X-ray tube and the X-ray detector as expressed with respect to the coordinate system of the subject image may be pre-stored. The target positions of the X-ray tube and the X-ray detector may be acquired based on the stored relative position information, and a control amount for causing the X-ray tube and the X-ray detector to be moved to the respective target positions is calculated. The target positions of the X-ray tube and the X-ray detector, more particularly, the positions corresponding to the part to be subjected to X-ray imaging, may be positions where each of the center of the X-ray radiation region of the X-ray tube and the center of the detection region of the X-ray detector respectively matches the part to be subjected to X-ray imaging or the center thereof in a two-dimensional space.

In operation 625, the X-ray tube and the X-ray detector are moved based on the calculated control amount, and X-ray imaging is performed.

Figure 42:
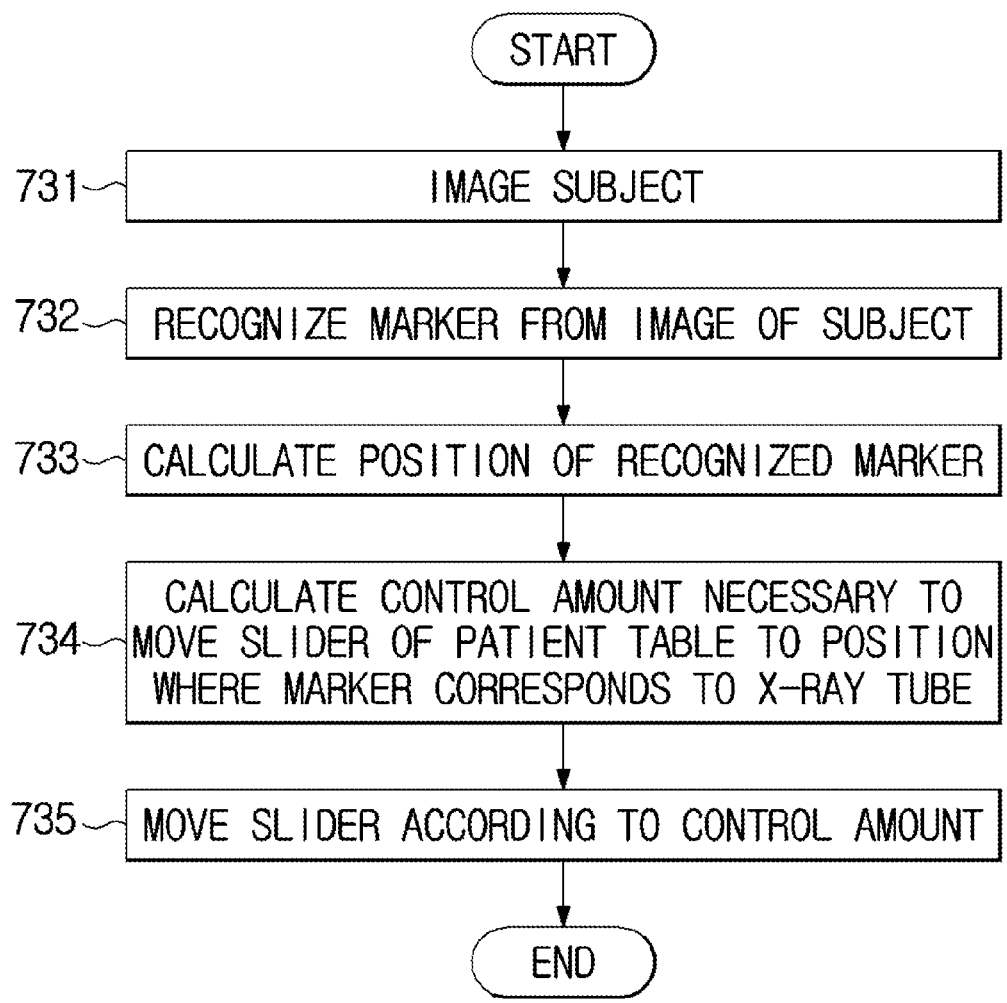
FIG. 42 is a flowchart which illustrates a method for controlling an X-ray imaging apparatus which corresponds to the exemplary embodiment illustrated in FIG. 16.

FIG. 42 is a flowchart which illustrates a method for controlling an X-ray imaging apparatus which corresponds to the exemplary embodiment illustrated in FIG. 16. The X-ray imaging apparatus applied to the present exemplary embodiment is a computed tomography (CT) device.

Referring to FIG. 42, in operation 731, a subject is imaged by using a camera before commencement of X-ray imaging. The subject is imaged in a state in which preparation for X-ray imaging is completed; in particular, in a state in which the subject is located on the slider of the patient table. A user locates a marker at a part to be subjected to X-ray imaging. The subject may be imaged in a single stage if the camera is a wide-angle camera which is capable of covering an entirety of the subject or the patient table, and may be imaged in multiple stages if the camera is a normal camera which has a normal lens mounted therein.

In operation 732, the marker is recognized from the image of the subject. The marker may be recognized by using at least one of various object recognition algorithms, and information relating to at least one of particular features of the marker may be pre-stored, and the marker which has the particular features may be recognized from the image of the subject.

In operation 733, the position of the recognized marker is calculated. More specifically, the position of the marker is calculated with respect to the slider of the patient table. If the position of the marker appearing in the subject image is calculated as two-dimensional coordinates on the slider, the position of the marker may indicate which point of the slider is located between the X-ray tube and the X-ray detector. For example, if the position of the marker is expressed as (m, n), the position (m, n) of the slider is located between the X-ray tube and the X-ray detector for X-ray imaging.

In operation 734, a control amount for causing the slider of the patient table to be moved to the position where the marker corresponds to the X-ray tube is calculated. Information relating to the relative position between the slider and the X-ray tube may be pre-stored. In particular, the actual position of the X-ray tube as expressed with respect to the coordinate system of the subject image may be pre-stored. A control amount for causing the position of the marker to correspond to the center of the radiation region of the X-ray tube on the slider is calculated based on the stored relative position information. Because the X-ray imaging apparatus according to the present exemplary embodiment is mounted in the gantry in a state in which the X-ray tube and the X-ray detector face each other, the position of the slider may correspond to any one of the X-ray tube and the X-ray detector.

In operation 735, the slider is moved based on the calculated control amount, and X-ray imaging is performed.

Figure 43:
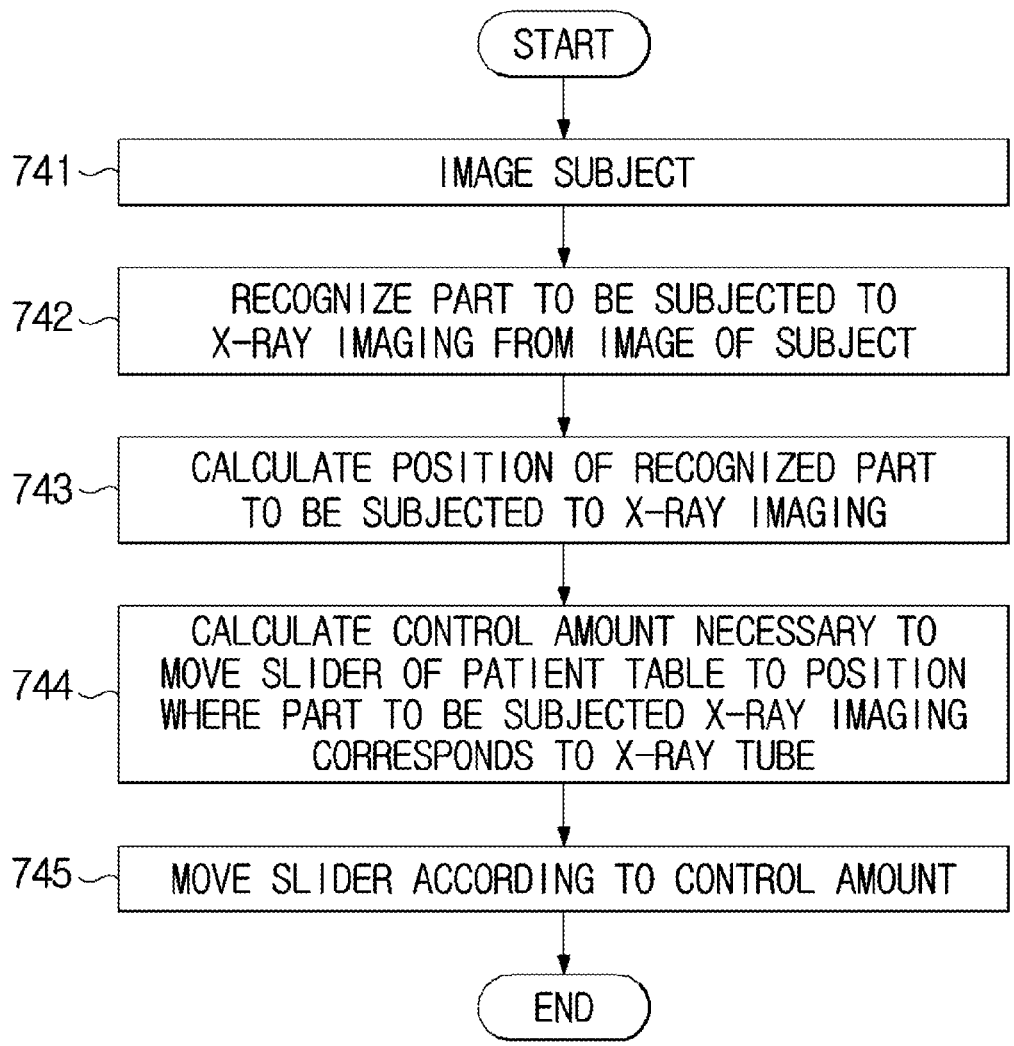
FIG. 43 is a flowchart which illustrates a method for controlling an X-ray imaging apparatus which corresponds to the exemplary embodiment illustrated in FIG. 18.

FIG. 43 is a flowchart which illustrates a method for controlling an X-ray imaging apparatus which corresponds to the exemplary embodiment illustrated in FIG. 18. The X-ray imaging apparatus applied to the present exemplary embodiment is a CT device.

Referring to FIG. 43, in operation 741, a subject is imaged by using a camera before commencement of X-ray imaging. The subject is imaged in a state in which preparation for X-ray imaging is completed; in particular, in a state in which the subject is located between the X-ray tube and the X-ray detector. The subject may be imaged in a single stage if the camera is a wide-angle camera which is capable of covering an entirety of the subject or the patient table, and may be imaged in multiple stages if the camera is a normal camera which has a normal lens mounted therein.

In operation 742, a part to be subjected to X-ray imaging is recognized from the image of the subject. The part to be subjected to X-ray imaging may be recognized by using at least one of various object recognition algorithms, and information relating to at least one of particular features of the part to be subjected to X-ray imaging may be pre-stored, and the part to be subjected to X-ray imaging which has the particular features may be recognized from the image of the subject.

In operation 743, the position of the recognized part to be subjected to X-ray imaging is calculated. In an exemplary embodiment, the position of the part to be subjected to X-ray imaging may be calculated on the slider. If the position of the part to be subjected to X-ray imaging may be calculated as two-dimensional coordinates, the position of the part to be subjected to X-ray imaging may indicate the center of the part to be subjected to X-ray imaging. However, the position of the center of the part to be subjected to X-ray imaging is not necessarily calculated, and the position of an arbitrary portion of the part to be subjected to X-ray imaging may be calculated based on the size of the part to be subjected to X-ray imaging.

In operation 744, a control amount for causing the slider of the patient table to be moved to a position where the part to be subjected to X-ray imaging corresponds to the X-ray tube is calculated. Information relating to the relative position between the slider and the X-ray tube may be pre-stored. A control amount for causing the position of the part to be subjected to X-ray imaging on the slider to correspond to the center of the radiation region of the X-ray tube is calculated based on the stored relative position information. Because the X-ray imaging apparatus according to the present exemplary embodiment is mounted in the gantry in a state in which the X-ray tube and the X-ray detector face each other, the position of the slider may correspond to any one of the X-ray tube and the X-ray detector.

In operation 745, the slider is moved based on the calculated control amount, and X-ray imaging is performed.

Figure 44:
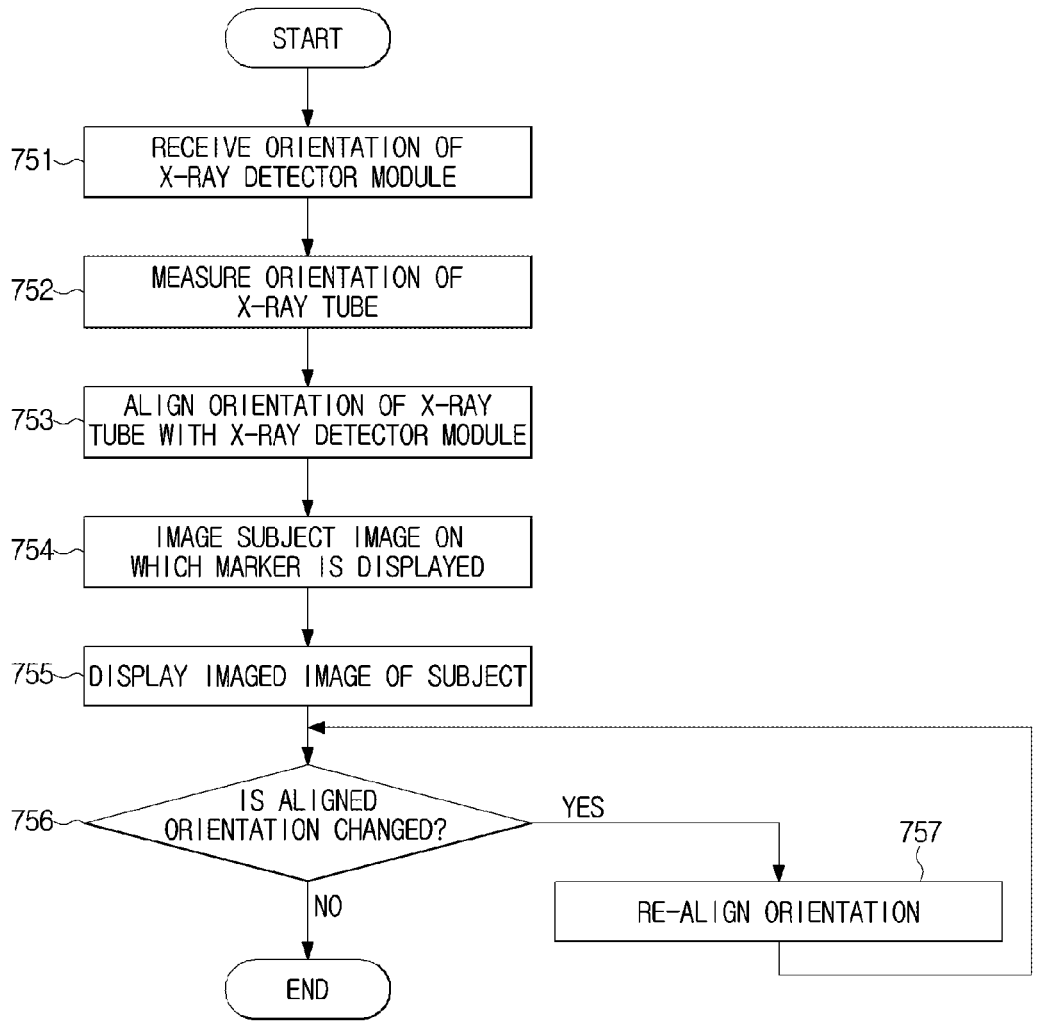
FIG. 44 is a flowchart illustrating a method of controlling an X-ray imaging apparatus that corresponds to the embodiment of FIG. 20.

FIG. 44 is a flowchart illustrating a method of controlling an X-ray imaging apparatus that corresponds to the embodiment of FIG. 20. The X-ray imaging apparatus applied to this embodiment is a mobile X-ray imaging apparatus.

As illustrated in FIG. 44, an orientation of the X-ray detector module is received (751). The X-ray detector module 600 may be implemented in a portable type separate from the X-ray imaging apparatus 500. A measured value of at least one of the angular velocity sensor, the accelerometer and the geomagnetic sensor of the X-ray detector module 600 may be transmitted to the communication unit 570 of the X-ray imaging apparatus 500 through the communication unit 630.

An orientation of the X-ray tube is measured (752). The sensing unit 580 mounted on the X-ray tube head 505 may measure the orientation of the X-ray tube 511. The sensing unit 580 may include the angular velocity sensor. In order to increase accuracy of orientation measurement, the accelerometer or the geomagnetic sensor may be further included.

The orientation of the X-ray tube is aligned with the X-ray detector module (753). The controller 550 may compare the orientation of the X-ray detector module 600 received from the communication unit 630 and a current orientation of the X-ray tube 511 measured by the sensing unit 580, and calculate a control amount for aligning the orientation of the X-ray tube 511. For example, the orientation of the X-ray tube 511 in which X-rays vertically radiated from the X-ray tube 511 can be vertically incident on an X-ray detector 521 may be defined as an orientation corresponding to the X-ray detector 610. A control signal including information on the calculated control amount may be transmitted to the first driver 512a, the second driver 512b and the third driver 512c. The first driver 512a, the second driver 512b and the third driver 512c may provide power to the first subarm 503a, the second subarm 503b and the third subarm 503c, respectively, to be aligned at a desired angle.

A subject image on which the marker is displayed is imaged (754). The imaged part of the subject may be displayed by the marker. As an example, the imaging unit 530 may be mounted on the X-ray tube head 505. The subject image may be imaged in real time. Also, imaging may have been performed before the orientation of the X-ray tube 511 is aligned.

The imaged image of the subject is displayed (755). The imaged image may be displayed on the display unit 561 in real time. For example, as exemplified in FIG. 29, the center C of the X-ray tube 511 may be also displayed and guide the user's manipulation. In order to align the position of the X-ray tube 511, the user may manipulate the fourth subarm 503d, the fifth subarm 503e and the sixth subarm 503f while checking the subject image displayed on the display unit 561.

Meanwhile, the orientation alignment of the X-ray tube 511 may be performed in real time. That is, even when the orientation is aligned in operation 753, the aligned orientation may be changed in the following process of aligning the position. Therefore, the controller 550 checks whether the aligned orientation is changed in real time while the position alignment of the X-ray tube 511 is performed (756). When the orientation is changed (Yes in 756), the orientation may be aligned again (757).

Figure 45:
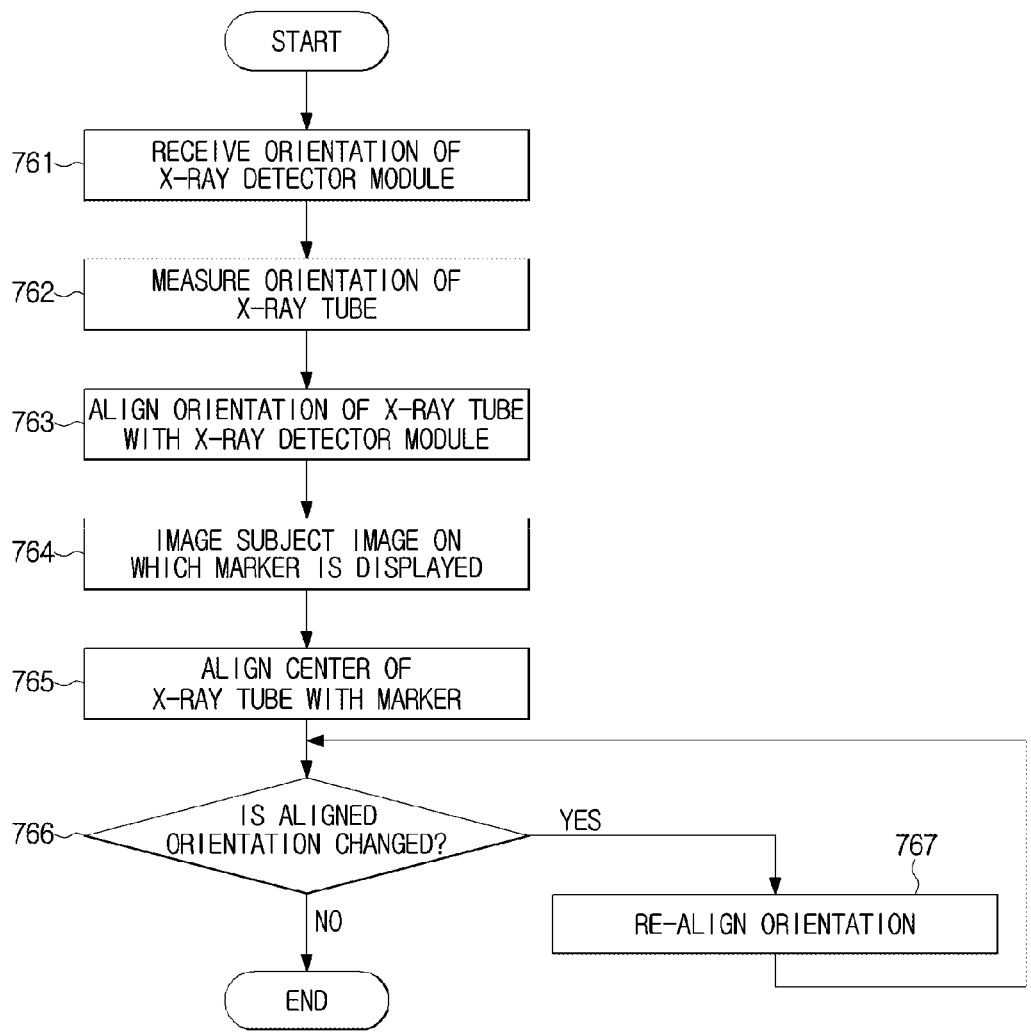
FIG. 45 is a flowchart illustrating a method of controlling an X-ray imaging apparatus in which position alignment is performed automatically or semi-automatically.

FIG. 45 is a flowchart illustrating a method of controlling an X-ray imaging apparatus in which position alignment is performed automatically or semi-automatically.

As illustrated in FIG. 45, the orientation of the X-ray detector module is received (761), and the orientation of the X-ray tube is measured (762).

The orientation of the X-ray tube is aligned with the X-ray detector module (763). The controller 550 may compare the orientation of the X-ray detector module 600 and a current orientation of the X-ray tube 511, and calculate a control amount for aligning the orientation of the X-ray tube 511. A control signal including information on the calculated control amount may be transmitted to the first driver 512a, the second driver 512b and the third driver 512c.

A subject image on which the marker is displayed is imaged (764). Imaging of the subject image may be performed in real time. Also, imaging may have been performed before the orientation of the X-ray tube 511 is aligned. Since descriptions of orientation alignment and imaging of the subject image are the same as those in FIG. 44, detailed descriptions thereof will not be provided in this example.

A position is aligned such that a center of the X-ray tube is aligned with the marker (765). The controller 550 may apply a recognition algorithm, recognize the marker 50 from the subject image, and calculate a position of the recognized marker. The controller 550 may calculate a control amount for aligning the position of the X-ray tube 511 with the position of the marker 50. The position of the X-ray tube 511 corresponding to the marker 50 may be a position in which a center of the X-ray tube 511 is aligned with the marker 50.

Some or all of the fourth subarm 503*d*, the fifth subarm 503*e* and the sixth subarm 503*f* involved in position alignment may be automatically controlled. When only some thereof are automatically controlled, the remaining arms may be manually controlled by the user. In this case, the subject image imaged in real time may be displayed on the display unit 561 and may guide the user's manipulation.

Also, similar to the above examples, the orientation alignment of the X-ray tube 511 may be performed in real time. That is, even when the orientation is aligned in operation 763, the aligned orientation may be changed in the following process of aligning the position. Therefore, the controller 550 checks whether the aligned orientation is changed in real time while the position alignment of the X-ray tube 511 is performed (766). When the orientation is changed (Yes in 766), the orientation may be aligned again (767).

According to exemplary embodiments, it is possible to recognize a marker located at a part to be subjected to X-ray imaging from an image of a subject which is generated by using a camera, and to control a respective movement of each of an X-ray tube and an X-ray detector to a respective position which corresponds to the recognized marker in order to prevent inconvenience, such as a direct movement of the X-ray tube and the X-ray detector, and to reduce an X-ray imaging time and the amount of X-rays to which a patient is exposed.

Although a few exemplary embodiments have been shown and described, it would be appreciated by those skilled in the art that changes may be made in these exemplary embodiments without departing from the principles and spirit of the present inventive concept, the scope of which is defined in the claims and their equivalents.

What is claimed is:

1. An X-ray imaging apparatus comprising:
   an X-ray tube which is configured to radiate X-rays toward a subject;
   an imaging unit which is configured to generate an image of the subject; and
   a position controller which is configured to recognize a part to be subjected to X-ray imaging from the generated image of the subject and performs control such that the X-ray tube is moved to a position corresponding to the part to be subjected to X-ray imaging,
   wherein the imaging unit comprises a wide-angle camera having an angle of view that encompasses an entirety of the subject such that the image of the subject is generated in a single stage.

2. The X-ray imaging apparatus according to claim 1, wherein:
   the position controller is further configured to recognize a marker from the generated image of the subject in order to recognize the part to be subjected to X-ray imaging of the subject, and
   the marker is located at the part to be subjected to X-ray imaging of the subject.

3. The X-ray imaging apparatus according to claim 2, wherein the position controller is further configured to control each of a center of an X-ray radiation region of the X-ray tube and a center of an X-ray detection region of an X-ray detector to match with a position of the marker.

4. The X-ray imaging apparatus according to claim 3, wherein the position controller is further configured to calculate the position of the marker, and to calculate a control amount for causing respective positions of each of the X-ray tube and the X-ray detector to respectively correspond to the calculated position of the marker based on a relative position between the generated image of the subject and at least one of the X-ray tube and the X-ray detector.

5. The X-ray imaging apparatus according to claim 2, wherein the position controller is further configured to recognize at least one of a shape, a color, a material and a size of the marker.

6. The X-ray imaging apparatus according to claim 2, wherein the marker comprises an object having a recognizable feature and comprises a user's hand having a specific shape.

7. The X-ray imaging apparatus according to claim 2, wherein the position controller is further configured to recognize an object having at least one of a shape, a color, material, and a size of the marker from the generated image of the subject.

8. The X-ray imaging apparatus according to claim 1, wherein:
   the imaging unit is mounted on the X-ray tube, and
   the position controller is further configured to update a position calculation result of the part to be subjected to X-ray imaging while the X-ray tube moves to the respective position which corresponds to the part to be subjected X-ray imaging.

9. The X-ray imaging apparatus according to claim 1, wherein the position controller is further configured to recognize a pre-stored feature of the part to be subjected to X-ray imaging from the generated image of the subject.

10. The X-ray imaging apparatus according to claim 1, further comprising
    an X-ray detecting unit configured to detect X-rays transmitted through the subject,
    wherein the position controller is further configured to perform control such that the X-ray detecting unit is moved to a position corresponding to the part to be subjected to X-ray imaging.

11. An X-ray imaging apparatus comprising:
    a gantry which comprises an X-ray tube which radiates X-rays toward a subject and an X-ray detector which detects X-rays which propagate through the subject;
    a slider which moves the subject to a bore of the gantry;
    an imaging unit which generates an image of the subject; and
    a position controller which is configured to recognize a part to be subjected to X-ray imaging from the generated image of the subject, and to control a movement of the slider such that a position of the part to be subjected to X-ray imaging corresponds to a respective position of at least one of the X-ray tube and the X-ray detector,
    wherein the imaging unit comprises a wide-angle camera having an angle of view that encompasses an entirety of the subject such that the image of the subject is generated in a single stage.

12. The X-ray imaging apparatus according to claim 11, wherein:
    the position controller is further configured to recognize a marker from the generated image of the subject in order to recognize the part to be subjected to X-ray imaging, and
    the marker is located at the part to be subjected to X-ray imaging.

13. The X-ray imaging apparatus according to claim 12, wherein the position controller is further configured to calculate a position of the marker, and to calculate a control amount for causing the slider to move based on a relative position between the generated image of the subject and at least one of the X-ray tube and the X-ray detector.

14. The X-ray imaging apparatus according to claim 11, wherein the position controller is further configured to recognize a pre-stored feature of the part to be subjected to X-ray imaging from the generated image of the subject.

15. A method for controlling an X-ray imaging apparatus which comprises an X-ray tube which radiates X-rays toward a subject and an X-ray detector which detects X-rays which propagate through the subject, the method comprising:
generating an image of the subject;
recognizing a part to be subjected to X-ray imaging from the generated image of the subject; and
controlling a respective movement of each of the X-ray tube and the X-ray detector to a respective position which corresponds to the part to be subjected to X-ray imaging,
wherein the image of the subject is generated by using a wide-angle camera having an angle of view that encompasses an entirety of the subject such that the image of the subject is generated in a single stage.

16. The method according to claim 15, wherein the recognizing of the part to be subjected to X-ray imaging comprises recognizing a marker from the generated image of the subject in order to recognize the part to be subjected to X-ray imaging of the subject.

17. The method according to claim 16, wherein the controlling of the respective movement of each of the X-ray tube and the X-ray detector to the position which corresponds to the part to be subjected to X-ray imaging comprises controlling each of a center of an X-ray radiation region of the X-ray tube and a center of an X-ray detection region of the X-ray detector to match with a position of the marker.

18. The method according to claim 16, wherein the controlling of the respective movement of each of the X-ray tube and the X-ray detector to the position which corresponds to the part to be subjected to X-ray imaging comprises calculating a position of the marker, and calculating a control amount for causing respective positions of each of the X-ray tube and the X-ray detector to respectively correspond to the calculated position of the marker based on a relative position between the generated image of the subject and at least one of the X-ray tube and the X-ray detector.

19. The method according to claim 16, further comprising pre-storing information relating to a feature which comprises information relating to at least one of a shape, a color, a material and a size of the marker.

20. The method according to claim 19, wherein the marker comprises an object having a recognizable feature and comprises a user's hand having a specific shape.

21. The method according to claim 19, wherein the recognizing of the part to be subjected to X-ray imaging of the subject comprises recognizing an object having the feature which comprises the information relating to at least one of the shape, the color, the material, and the size of the marker from the generated image of the subject.

22. The method according to claim 15, wherein:
an imaging unit is mounted in the X-ray tube, and
the calculating the position of the marker comprises updating a position calculation result of the part to be subjected to X-ray imaging while the X-ray tube moves to the respective position which corresponds to the part to be subjected X-ray imaging.

23. The method according to claim 15, further comprising pre-storing information relating to a feature of the part to be subjected to X-ray imaging,
wherein the recognizing the part to be subjected to X-ray imaging comprises recognizing the feature from the generated image of the subject.

24. A method for controlling an X-ray imaging apparatus which comprises a gantry which comprises an X-ray tube which radiates X-rays toward a subject and an X-ray detector which detects X-rays which propagate through the subject, the method comprising:
moving a slider, on which the subject is located, to a bore of the gantry;
generating an image of the subject;
recognizing a part to be subjected to X-ray imaging from the generated image of the subject; and
controlling a movement of the slider such that the part to be subjected to X-ray imaging corresponds to a respective position of at least one of the X-ray tube and the X-ray detector,
wherein the image of the subject is generated by using a wide-angle camera having an angle of view that encompasses an entirety of the subject such that the image of the subject is generated in a single stage.

25. The method according to claim 24, wherein the recognizing of the part to be subjected to X-ray imaging from the generated image of the object comprises recognizing a marker which is located at the part to be subjected to X-ray imaging from the generated image of the subject.

26. The method according to claim 25, wherein the controlling of the movement of the slider comprises pre-storing information relating to a relative position between the generated image of the subject and at least one of the X-ray tube and the X-ray detector and calculating a control amount for causing the slider to move based on the pre-stored information relating to the relative position.

27. The method according to claim 26, wherein the calculating of the control amount for causing the slider to move comprises calculating a control amount for causing the slider to move such that a position of the marker corresponds to at least one of the X-ray tube and the X-ray detector.

28. The method according to claim 26, wherein the recognizing of the part to be X-ray imaging of the object comprises pre-storing information relating to a feature of the part to be subjected to X-ray imaging and recognizing the feature from the generated image of the subject.

* * * * *